US009017960B2

(12) United States Patent
Liu et al.

(10) Patent No.: US 9,017,960 B2
(45) Date of Patent: Apr. 28, 2015

(54) CRYSTAL STRUCTURE OF AMINO TERMINAL PORTION OF INFLUENZA VIRUS POLYMERASE PA SUBUNIT AND USE THEREOF

(75) Inventors: Yingfang Liu, Beijing (CN); Zihe Rao, Beijing (CN)

(73) Assignee: Institute of Biophysics Chinese Academy of Sciences, Beijing (CN)

( * ) Notice: Subject to any disclaimer, the term of this patent is extended or adjusted under 35 U.S.C. 154(b) by 15 days.

(21) Appl. No.: 13/254,823

(22) PCT Filed: Feb. 3, 2010

(86) PCT No.: PCT/CN2010/070500
§ 371 (c)(1),
(2), (4) Date: Mar. 2, 2012

(87) PCT Pub. No.: WO2010/088857
PCT Pub. Date: Aug. 12, 2010

(65) Prior Publication Data
US 2013/0046076 A1    Feb. 21, 2013

(30) Foreign Application Priority Data

Feb. 4, 2009  (CN) .......................... 2009 1 0077937

(51) Int. Cl.
| | | |
|---|---|---|
| *C12Q 1/34* | (2006.01) | |
| *C07K 14/005* | (2006.01) | |
| *C12N 9/12* | (2006.01) | |

(Continued)

(52) U.S. Cl.
CPC ........... *C07K 14/005* (2013.01); *C07K 2299/00* (2013.01); *C12N 9/127* (2013.01); *C12N 2760/16122* (2013.01); *C12N 2760/16222* (2013.01); *C12N 2760/16322* (2013.01); *C40B 30/02* (2013.01); *G06F 19/16* (2013.01); *G06F 19/706* (2013.01)

(58) Field of Classification Search
None
See application file for complete search history.

(56) References Cited

U.S. PATENT DOCUMENTS

2005/0143402 A1 * 6/2005 Cheetham et al. ....... 514/266.21
2012/0108493 A1 * 5/2012 Bouvier et al. ................ 514/1.1

FOREIGN PATENT DOCUMENTS

WO    WO2008/039267    4/2008

OTHER PUBLICATIONS

Wiencek, J. M. Ann. Rev. Biomed. Eng. 1999, 1, 505-534).*

(Continued)

*Primary Examiner* — Nashaat Nashed

(57) ABSTRACT

Present invention discloses the three-dimensional crystal structure of the N-terminus polypeptide of influenza virus polymerase subunit (PA_N of SEQ ID NO:7). PA_N of SEQ ID NO: 1 is residues 1—50 to 150-300 of influenza virus polymerase subunit PA. In the three-dimensional structure, at least 40% of atoms show the same atomic coordinates, compared to that listed in Table 1. Namely, in the three-dimensional structure of influenza virus polymerase subunit PA_N of SEQ ID NO: 7, 40% of atomic coordinates on carbon skeleton of residues of influenza virus polymerase subunit PA_N of SEQ ID NO: 7, show less than or equal to 1.7 Å of average variance, compared to the atomic coordinates listed in Table 1. Present invention also discloses the expression, purification, crystallization methods, and three-dimensional crystal structure of 256 residues in the N-terminus of influenza virus polymerase subunit PA, and applications of the crystal structure of SEQ ID NO: 7 on drug screening and designing.

12 Claims, 4 Drawing Sheets
(4 of 4 Drawing Sheet(s) Filed in Color)

(51) Int. Cl.
    *C40B 30/02*     (2006.01)
    *G06F 19/16*     (2011.01)
    *G06F 19/00*     (2011.01)

(56) References Cited

OTHER PUBLICATIONS

Yuan et al. Crystal structure of avian influenza polymerase PAN reveals an endonuclease active site. Nature (published on line Feb. 4, 2009 and printed Apr. 2009) 458, 909-913.*

Dias et al. Nature (published on line Feb. 1, 2009 and printed Apr. 2009) 458, 914-918.*

Dias et al. Nature (published on line publication Feb. 1, 2009) Supplementary material 458, 914-918.*

Hara et al. J. Virology (2008) 80 (16) 7789-7798.*

Zhao, C. et al. "Nucleoside Monophosphate Complex Structures of the Endonuclease Domain . . . " Journel of Virology, Sep. 2009, p. 9024-9030, American Society for Microbiology.

Dias, A. et al. "The cap-snatching endonuclease of influenza virus polymerase resides in the PA subunit"; Nature 458, p. 914-918; Apr. 16, 2009; Abstract only.

* cited by examiner

SEQUENCE LISTING

```
<160> NUMBER OF SEQ ID NOS: 6

<210> SEQ ID NO 1
<211> LENGTH: 716
<212> TYPE: PRT
<213> ORGANISM: influenza virus type A strain, A/goose/Guangdong/1/96
<220> FEATURE:
<221> NAME/KEY: MISC_FEATURE
<223> OTHER INFORMATION: Polymerase subunit PA protein.

<400> SEQUENCE: 1
```

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
            35                  40                  45

Ser Asp Phe His Phe Ile Asp Glu Arg Gly Glu Ser Thr Ile Ile Glu
50                      55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
                100                 105                 110

Lys Glu Asn Arg Phe Ile Glu Ile Gly Val Thr Arg Arg Glu Val His
            115                 120                 125

Thr Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
                180                 185                 190

Gln Ser Glu Arg Gly Glu Glu Thr Ile Glu Glu Arg Phe Glu Ile Thr
            195                 200                 205

Gly Thr Met Cys Arg Leu Ala Asp Gln Ser Leu Pro Pro Asn Phe Ser
    210                 215                 220

Ser Leu Glu Lys Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asp
                260                 265                 270

Gly Pro Pro Cys Ser Gln Arg Ser Lys Phe Leu Leu Met Asp Ala Leu
            275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Leu
                325                 330                 335

Ala Trp Lys Gln Val Leu Ala Glu Leu Gln Asp Ile Glu Asn Glu Glu
                340                 345                 350

Lys Ile Pro Lys Thr Lys Asn Met Arg Lys Thr Ser Gln Leu Lys Trp
            355                 360                 365

Ala Leu Gly Glu Asn Met Ala Pro Glu Lys Val Asp Phe Glu Asp Cys
    370                 375                 380

Lys Asp Val Ser Asp Leu Arg Gln Tyr Asp Ser Asp Glu Pro Lys Pro
385                 390                 395                 400

Arg Ser Leu Ala Ser Trp Ile Gln Ser Glu Phe Asn Lys Ala Cys Glu
                405                 410                 415
```

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
            435                 440                 445

Glu Val Ser His Cys Arg Ala Thr Glu Tyr Ile Met Lys Gly Val Tyr
        450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
            530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
610                 615                 620

Pro Lys Gly Met Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
            675                 680                 685

Ala Ile Glu Glu Cys Leu Ile Asn Asp Pro Trp Val Leu Leu Asn Ala
            690                 695                 700

Ser Trp Phe Asn Ser Phe Leu Thr His Ala Leu Lys
705                 710                 715

<210> SEQ ID NO 2
<211> LENGTH: 757
<212> TYPE: PRT
<213> ORGANISM: influenza virus type A strain, A/goose/Guangdong/1/96
<220> FEATURE:
<221> NAME/KEY: MISC_FEATURE
<223> OTHER INFORMATION: polymerase subunit PB1 protein

<400> SEQUENCE: 2

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

```
Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
                 85                  90                  95

Lys Ser His Pro Gly Ile Phe Glu Asn Ser Cys Leu Glu Thr Met Glu
            100                 105                 110

Ile Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Gly Glu Met Glu Ile Ile Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480
```

-continued

```
Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys
        755

<210> SEQ ID NO 3
<211> LENGTH: 712
<212> TYPE: PRT
<213> ORGANISM: influenza  virus type B strain, B/Ann Arbor/1/1966
<220> FEATURE:
<221> NAME/KEY: MISC_FEATURE
<223> OTHER INFORMATION: Polymerase subunit PA protein.

<400> SEQUENCE: 3

Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
        35                  40                  45

Ser Asp Met Asn Phe Leu Asp Glu Glu Gly Lys Thr Tyr Thr Ala Leu
    50                  55                  60

Glu Gly Gln Gly Lys Glu Gln Asn Leu Arg Pro Gln Tyr Glu Val Ile
65                  70                  75                  80
```

-continued

```
Glu Gly Met Pro Arg Asn Ile Ala Trp Met Val Gln Arg Ser Leu Ala
            85                  90                  95

Gln Glu His Gly Ile Glu Thr Pro Arg Tyr Leu Ala Asp Leu Phe Asp
           100                 105                 110

Tyr Lys Thr Lys Arg Phe Ile Glu Val Gly Ile Thr Lys Gly Leu Ala
       115                 120                 125

Asp Asp Tyr Phe Trp Lys Lys Glu Lys Leu Gly Asn Ser Met Glu
130                 135                 140

Leu Met Ile Phe Ser Tyr Asn Gln Asp Tyr Ser Leu Ser Asn Glu His
145                 150                 155                 160

Ser Leu Asp Glu Glu Gly Lys Gly Arg Val Leu Ser Arg Leu Thr Glu
                165                 170                 175

Leu Gln Ala Glu Leu Ser Leu Lys Asn Leu Trp Gln Val Leu Ile Gly
            180                 185                 190

Glu Glu Asp Ile Glu Lys Gly Ile Asp Phe Lys Leu Gly Gln Thr Ile
        195                 200                 205

Ser Lys Leu Arg Asp Ile Ser Val Pro Ala Gly Phe Ser Asn Phe Glu
    210                 215                 220

Gly Met Arg Ser Tyr Ile Asp Asn Ile Asp Pro Lys Gly Ala Ile Glu
225                 230                 235                 240

Arg Asn Leu Ala Arg Met Ser Pro Leu Val Ser Val Thr Pro Lys Lys
                245                 250                 255

Leu Lys Trp Glu Asp Leu Arg Pro Ile Gly Pro His Ile Tyr Ser His
            260                 265                 270

Glu Leu Pro Glu Val Pro Tyr Asn Ala Phe Leu Leu Met Ser Asp Glu
        275                 280                 285

Leu Gly Leu Ala Asn Met Thr Glu Gly Lys Ser Lys Lys Pro Lys Thr
    290                 295                 300

Leu Ala Lys Glu Cys Leu Glu Lys Tyr Ser Thr Leu Arg Asp Gln Thr
305                 310                 315                 320

Asp Pro Ile Leu Ile Met Lys Ser Glu Lys Ala Asn Glu Asn Phe Leu
                325                 330                 335

Trp Lys Leu Trp Arg Asp Cys Val Asn Thr Ile Ser Asn Glu Glu Thr
            340                 345                 350

Ser Asn Glu Leu Gln Lys Thr Asn Tyr Ala Lys Trp Ala Thr Gly Asp
        355                 360                 365

Gly Leu Thr Tyr Gln Lys Ile Met Lys Glu Val Ala Ile Asp Asp Glu
    370                 375                 380

Thr Met Tyr Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Val Ala Pro Val Glu
            420                 425                 430

His Val Gly Ser Glu Arg Arg Lys Tyr Phe Val Asn Glu Ile Asn Tyr
        435                 440                 445

Cys Lys Ala Ser Thr Val Met Met Lys Tyr Val Leu Phe His Thr Ser
    450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Ile Leu
                485                 490                 495
```

-continued

Tyr Gly Leu Ala Val Lys Gly Gln Ser His Leu Arg Gly Asp Thr Asp
                500                 505                 510

Val Val Thr Val Val Thr Phe Glu Phe Ser Ser Thr Asp Pro Arg Val
            515                 520                 525

Asp Ser Gly Lys Trp Pro Lys Tyr Thr Val Phe Arg Ile Gly Ser Leu
        530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Asp Gln Glu Ser
            580                 585                 590

Ser Ile Gln Gly Tyr Asp Met Thr Lys Ala Cys Phe Lys Gly Asp Arg
        595                 600                 605

Val Asn Ser Pro Lys Thr Phe Ser Ile Gly Thr Gln Glu Gly Lys Leu
610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Ile Gln Ala Leu Lys Asp Arg Lys
            660                 665                 670

Gly Pro Trp Val Phe Asp Leu Glu Gly Met Tyr Ser Gly Ile Glu Glu
        675                 680                 685

Cys Ile Ser Asn Asn Pro Trp Val Ile Gln Ser Ala Tyr Trp Phe Asn
690                 695                 700

Glu Trp Leu Gly Phe Glu Lys Glu
705                 710

<210> SEQ ID NO 4
<211> LENGTH: 700
<212> TYPE: PRT
<213> ORGANISM: influenza virus type C strain, C/JJ/1950
<220> FEATURE:
<221> NAME/KEY: MISC_FEATURE
<223> OTHER INFORMATION: Polymerase subunit PA protein.
<220> FEATURE:
<221> NAME/KEY: misc_feature
<222> LOCATION: (230)..(237)
<223> OTHER INFORMATION: Xaa can be any naturally occurring amino acid

<400> SEQUENCE: 4

Met Ser Lys Thr Phe Ala Glu Ile Ala Glu Thr Phe Leu Glu Pro Glu
1               5                   10                  15

Ala Val Arg Ile Ala Lys Glu Ala Val Glu Glu Tyr Gly Asp His Glu
                20                  25                  30

Arg Lys Ile Ile Gln Ile Gly Ile His Phe Gln Val Cys Cys Met Phe
            35                  40                  45

Cys Asp Glu Tyr Leu Ser Thr Asn Gly Ser Asp Arg Phe Val Leu Ile
        50                  55                  60

Glu Gly Arg Lys Arg Gly Thr Ala Val Ser Leu Gln Asn Glu Leu Cys
65                  70                  75                  80

Lys Ser Tyr Asp Leu Glu Pro Leu Pro Phe Leu Cys Asp Ile Phe Asp
                85                  90                  95

Arg Glu Glu Lys Gln Phe Val Gly Ile Gly Ile Thr Arg Lys Ala Asp
            100                 105                 110

```
Asp Ser Tyr Phe Gln Ser Lys Phe Gly Lys Leu Gly Asn Ser Cys Lys
        115                 120                 125

Ile Phe Val Phe Ser Tyr Asp Gly Arg Leu Asp Lys Asn Cys Glu Gly
    130                 135                 140

Pro Met Glu Glu Gln Lys Leu Arg Ile Phe Ser Phe Leu Ala Thr Ala
145                 150                 155                 160

Ala Asp Phe Leu Arg Lys Glu Asn Met Phe Asn Glu Ile Phe Leu Pro
                165                 170                 175

Asp Asn Glu Glu Thr Ile Ile Glu Met Lys Lys Gly Lys Thr Phe Leu
            180                 185                 190

Lys Leu Arg Asp Glu Ser Val Pro Leu Pro Phe Gln Thr Tyr Glu Gln
        195                 200                 205

Met Lys Asp Tyr Cys Glu Lys Phe Lys Gly Asn Pro Arg Glu Leu Ala
    210                 215                 220

Ser Lys Val Ser Gln Xaa Xaa Xaa Xaa Xaa Xaa Xaa Ile Lys His
225                 230                 235                 240

Tyr Glu Gln Asn Lys Phe Arg Gln Ile Arg Leu Pro Lys Gly Pro Met
                245                 250                 255

Ala Pro Tyr Thr His Lys Phe Leu Met Glu Glu Ala Trp Met Phe Thr
            260                 265                 270

Lys Ile Ser Asp Pro Glu Arg Ser Arg Ala Gly Glu Ile Leu Ile Asp
        275                 280                 285

Phe Phe Lys Lys Gly Asn Leu Ser Ala Ile Arg Pro Lys Asp Lys Pro
    290                 295                 300

Leu Gln Gly Lys Tyr Pro Ile His Tyr Lys Asn Leu Trp Asn Gln Ile
305                 310                 315                 320

Lys Ala Ala Ile Ala Asp Arg Thr Met Val Ile Ser Glu Asn Asp His
                325                 330                 335

Ser Glu Phe Leu Gly Gly Ile Gly Arg Ala Ser Lys Lys Ile Pro Glu
            340                 345                 350

Val Ser Leu Thr Gln Asp Val Ile Thr Thr Glu Gly Leu Lys Gln Ser
        355                 360                 365

Glu Asn Lys Leu Pro Glu Pro Arg Ser Phe Pro Lys Trp Phe Asn Ala
    370                 375                 380

Glu Trp Met Trp Ala Ile Lys Asp Ser Asp Leu Thr Gly Trp Val Pro
385                 390                 395                 400

Met Ala Glu Tyr Pro Pro Ala Asp Asn Glu Leu Glu Asp Tyr Ala Glu
                405                 410                 415

His Leu Asn Lys Thr Met Glu Gly Val Leu Gln Gly Thr Asn Cys Ala
            420                 425                 430

Arg Glu Met Gly Lys Cys Ile Leu Thr Val Gly Ala Leu Met Thr Glu
        435                 440                 445

Cys Arg Leu Phe Pro Gly Lys Ile Lys Val Val Pro Ile Tyr Ala Arg
    450                 455                 460

Ser Lys Glu Arg Lys Ser Met Gln Glu Gly Leu Pro Val Pro Ser Glu
465                 470                 475                 480

Met Asp Cys Leu Phe Gly Ile Cys Val Lys Ser Lys Ser His Leu Asn
                485                 490                 495

Lys Asp Asp Gly Met Tyr Thr Ile Ile Thr Phe Glu Phe Ser Ile Arg
            500                 505                 510

Glu Pro Asn Leu Glu Lys His Gln Lys Tyr Thr Val Phe Glu Ala Gly
        515                 520                 525
```

His Thr Thr Val Arg Met Lys Lys Gly Glu Ser Val Ile Gly Arg Glu
            530                 535                 540

Val Pro Leu Tyr Leu Tyr Cys Arg Thr Thr Ala Leu Ser Lys Ile Lys
545                 550                 555                 560

Asn Asp Trp Leu Ser Lys Ala Arg Arg Cys Phe Ile Thr Thr Met Asp
                565                 570                 575

Thr Val Glu Thr Ile Cys Leu Arg Glu Ser Ala Lys Ala Glu Glu Asn
            580                 585                 590

Leu Val Glu Lys Thr Leu Asn Glu Lys Gln Met Trp Ile Gly Lys Lys
            595                 600                 605

Asn Gly Glu Leu Ile Ala Gln Pro Leu Arg Glu Ala Leu Arg Val Gln
610                 615                 620

Leu Val Gln Gln Phe Tyr Phe Cys Ile Tyr Asn Asp Ser Gln Leu Glu
625                 630                 635                 640

Gly Phe Cys Asn Glu Gln Lys Lys Ile Leu Met Ala Leu Glu Gly Asp
                645                 650                 655

Lys Lys Asn Lys Ser Ser Phe Gly Phe Asn Pro Glu Gly Leu Leu Glu
                660                 665                 670

Lys Ile Glu Glu Cys Leu Ile Asn Asn Pro Met Cys Leu Phe Met Ala
            675                 680                 685

Gln Arg Leu Asn Glu Leu Val Ile Glu Ala Ser Lys
690                 695                 700

<210> SEQ ID NO 5
<211> LENGTH: 261
<212> TYPE: PRT
<213> ORGANISM: Artificial Sequence
<220> FEATURE:
<223> OTHER INFORMATION: Sequence of the protein used for
      crystallization.

<400> SEQUENCE: 5

Gly Pro Leu Gly Ser Met Glu Asp Phe Val Arg Gln Cys Phe Asn Pro
1               5                   10                  15

Met Ile Val Glu Leu Ala Glu Lys Ala Met Lys Glu Tyr Gly Glu Asp
            20                  25                  30

Pro Lys Ile Glu Thr Asn Lys Phe Ala Ala Ile Cys Thr His Leu Glu
        35                  40                  45

Val Cys Phe Met Tyr Ser Asp Phe His Phe Ile Asp Glu Arg Gly Glu
    50                  55                  60

Ser Thr Ile Ile Glu Ser Gly Asp Pro Asn Ala Leu Leu Lys His Arg
65                  70                  75                  80

Phe Glu Ile Ile Glu Gly Arg Asp Arg Thr Met Ala Trp Thr Val Val
                85                  90                  95

Asn Ser Ile Cys Asn Thr Thr Gly Val Glu Lys Pro Lys Phe Leu Pro
            100                 105                 110

Asp Leu Tyr Asp Tyr Lys Glu Asn Arg Phe Ile Glu Ile Gly Val Thr
        115                 120                 125

Arg Arg Glu Val His Thr Tyr Tyr Leu Glu Lys Ala Asn Lys Ile Lys
    130                 135                 140

Ser Glu Lys Thr His Ile His Ile Phe Ser Phe Thr Gly Glu Glu Met
145                 150                 155                 160

Ala Thr Lys Ala Asp Tyr Thr Leu Asp Glu Glu Ser Arg Ala Arg Ile
                165                 170                 175

Lys Thr Arg Leu Phe Thr Ile Arg Gln Glu Met Ala Ser Arg Gly Leu
            180                 185                 190

```
Trp Asp Ser Phe Arg Gln Ser Glu Arg Gly Glu Glu Thr Ile Glu Glu
        195                 200                 205

Arg Phe Glu Ile Thr Gly Thr Met Cys Arg Leu Ala Asp Gln Ser Leu
    210                 215                 220

Pro Pro Asn Phe Ser Ser Leu Glu Lys Phe Arg Ala Tyr Val Asp Gly
225                 230                 235                 240

Phe Glu Pro Asn Gly Cys Ile Glu Gly Lys Leu Ser Gln Met Ser Lys
                245                 250                 255

Glu Val Asn Ala Arg
            260

<210> SEQ ID NO 6
<211> LENGTH: 716
<212> TYPE: PRT
<213> ORGANISM: influenza virus type A strain, A/Brevig Mission/1/1918
<220> FEATURE:
<221> NAME/KEY: MISC_FEATURE
<223> OTHER INFORMATION: Polymerase subunit PA protein.

<400> SEQUENCE: 6

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asp
            260                 265                 270
```

```
Gly Pro Pro Cys Ser Gln Arg Ser Lys Phe Leu Leu Met Asp Ala Leu
            275                 280                 285

Lys Leu Ser Ile Glu Asp Pro Ser His Glu Gly Glu Gly Ile Pro Leu
290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ala Trp Lys Gln Val Leu Ala Glu Leu Gln Asp Ile Glu Asn Glu Glu
            340                 345                 350

Lys Ile Pro Lys Thr Lys Asn Met Lys Thr Ser Gln Leu Lys Trp
            355                 360                 365

Ala Leu Gly Glu Asn Met Ala Pro Glu Lys Val Asp Phe Asp Asp Cys
370                 375                 380

Lys Asp Val Ser Asp Leu Lys Gln Tyr Asp Ser Asp Glu Pro Glu Leu
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Val
                420                 425                 430

Ala Pro Ile Glu His Ile Ala Ser Met Arg Arg Asn Tyr Phe Thr Ala
            435                 440                 445

Glu Val Ser His Cys Arg Ala Thr Glu Tyr Ile Met Lys Gly Val Tyr
            450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
            675                 680                 685
```

-continued

```
Ala Ile Glu Glu Cys Leu Ile Asn Asp Pro Trp Val Leu Leu Asn Ala
    690             695             700
Ser Trp Phe Asn Ser Phe Leu Thr His Ala Leu Arg
705             710             715
```

CRYSTAL STRUCTURE OF AMINO TERMINAL PORTION OF INFLUENZA VIRUS POLYMERASE PA SUBUNIT AND USE THEREOF

Field of the invention

The present invention describes the expression, purification, virus crystallization methods, and a three-dimensional crystal structure of residues 1-256 in the N-terminus polypeptide of influenza virus polymerase subunit PA (PA_N of SEQ ID NO: 7), and application of said structure on drug screening and designing.

BACKGROUND OF THE INVENTION

In recent years, highly pathogenic avian influenza A virus strains with H5N1 subtype have become entrenched in poultry worldwide and pose a growing threat to human health. Because of continuous variation of this virus, developing anew anti-influenza drug has become an urgent and major task for all countries. Demonstration of three-dimensional structures of the proteins which are related to the influenza virus has important scientific significance for understanding the viral replication, and is highly valuable for the development of anti-influenza viral drugs.

The RNA genome of the influenza virus contains 8 RNA segments which encode 11 virus-specific proteins. Influenza virus RNA-dependent RNA polymerase is a heterotrimeric complex (PA, PB1 and PB2) harboring several enzymatic activities for catalyzing both viral RNA replication and transcription, and acts to maintain virus life cycle. In particular, the high conservation and low mutation ratio of subunits PA, PB1 and PB2, enabled it as a viable target to design the anti-influenza drugs.

In recent years, it has been known that PB1 (SEQ ID NO: 2) subunit alone can catalyze viral RNA replication and transcription; PB2 subunit binds the 5' cap of host pre-mRNAs, which are subsequently cleaved by the viral endonuclease, hitherto thought to reside in the PB2 or PB1 (SEQ ID NO: 2) subunits.

Compared to the other two subunits, the mechanism of the PA subunit remained elusive. PA is an important protein in the polymerase heterotrimer and may be required for replication and transcription of viral RNA (vRNA) and endonuclease cleavage of the cap RNA primer. It reportedly induces proteolysis of the viral and host proteins and may also be involved in virus assembly. However, the molecular mechanism of PA remains unclear. Hereby, investigation of the PA structure is significantly important to study the whole RNA polymerase complex.

Analysis of protein structures is a very useful tool to understand protein function. Especially important to the study of the function of the complex is exploration of the whole complex. However, due to various difficulties, the structure of this protein complex has not been resolved.

In Chinese patents No. CN 200810100840.X and CN 200810083994.2 submitted on Feb. 22 and May 2 in 2008, present inventors disclosed three dimensional crystal structure of influenza A virus PA (PAC, residues 257-716 of SEQ ID NO: 1) in complex with the PA-binding region of PB1 (PB1N, residues 1-25 of SEQ ID NO: 2). Present inventors published the structure of avian H5N1 influenza A virus PA (PAC, residues 257-716 of SEQ ID NO: 1) in complex with the PA-binding region of PB1 (PB1N, residues 1-25 of SEQ ID NO:2) (He X et al. Nature, August 2008, 454(7208): 1123-6).

In order to obtain a completely three-dimensional crystal structure of the polymerase complex which consists of PA, PB1, and PB2 subunits, present inventors have conducted the following research.

SUMMARY OF THE INVENTION

Here inventors extended their previous study, and revealed the three-dimensional structure of the remaining region of PA (PA_N of SEQ ID NO: 7) by X-ray crystallography.

First, in this invention, the inventors disclose the three-dimensional structure of P_N of SEQ ID NO: 7 from an influenza virus RNA polymerase. PA_N of SEQ ID NO: 1 is residues 1~50 to 150-300 of influenza virus polymerase subunit PA of SEQ ID NO: 1. In the three-dimensional structure, at least 40% of atoms showed the same atomic coordinates, compared to that listed in Table 1. In other words, in the three-dimensional structure of influenza virus polymerase subunit PA_N of SEQ ID NO: 7 40% of atomic coordinates on the carbon skeleton of the amino acids of influenza virus polymerase subunit PA_N of SEQ ID NO: 7, showed less than or equal to 1.7 Å of average variance, compared to the atomic coordinates listed in Table 1.

Preferably, influenza viruses used in present invention were from influenza virus type A, B and C. And optimized influenza viruses were from influenza virus type A strain A/goose/Guangdong/1/96 (SEQ ID NO:1), and strain A/Brevig Mission/1/1918 (SEQ ID NO:8), type B: strain B/Ann Arbor/1/1966 (SEQ ID NO:3), and type C: strain C/JJ/1950 (SEQ ID NO:4).

Preferably, the parental crystal had a P1 space group, and cell parameters: a=51.1 Å, b=151.0 Å, c=59.8 Å, α=96.6°, β=96.8°, γ=109.5°. The selenomethionine labeled crystal had a P6(4)22 space group, and cell parameters: α=b=73.8 Å, c=123.4 Å, α=β=90°, γ=120°.

Preferably, PA_N of SEQ ID NO: 7 structure has an α/β architecture with seven α-helices, α-helix 1: residues 2-9; α-helix 2: residues 11-22; α-helix 3: residues 32-48; α-helix 4: residues 84-92; α-helix 5: residues 127-138; α-helix 6: residues165-184; α-helix 7: residues 187-191, and five β-sheets, β-sheet 1: residues 76-78; β-sheet 2; residues 109-111; β-sheet 3: residues 116-123; β-sheet 4: residues 144-149 and β-sheet 5: residues 154-157. Five parallel β-sheets formed a twisted plane surrounded by seven α-helices. Amino acids residues in influenza virus type A or B shown here, and corresponding residues in influenza virus type C were listed in FIG. 1.

Preferably, in the center of the three-dimensional structure of PA_N of SEQ ID NO: 7 from influenza virus type A RNA polymerase, there was a binding metal ion, which probably was magnesium, manganese, zinc, cuprum, cobalt or iron. And this metal is directly coordinated by the following ligands: three water molecules, acidic residues Glu80 and/or Asp108, and at least one acidic residue among residues His41, Glu119, Leu106 and Pro107. All six amino acids involved in coordinating this metal among influenza virus type A or B, and corresponding residues in influenza virus C, were shown in FIG. 1. More optimally, the metal ion mentioned above was identified as magnesium.

Preferably, in the three-dimensional structure of P_N of SEQ ID NO: 7 from influenza virus type A RNA polymerase, where motif residues $P_{107}D_{108}X(11)E_{119}X(15)K_{134}$, were similar to motif residues (P)DX$_N$(D/E)XK among the endonuclease. Amino acid residues among influenza virus type A or B and corresponding residues in influenza virus C were shown in FIG. 1, respectively.

Preferably, when T157、E153、E154、K158、D160、E165、E166、R168、R170 and Lys172 were located at the residues between β-sheet4 and α-helix7. These amino acid residues among influenza virus type A or B and corresponding residues in influenza virus C were shown in FIG. 1, respectively.

Preferably, in a three-dimensional structure of PA_N of SEQ ID NO: 7 from influenza virus type A RNA polymerase, where at least two or three residues among Arg179、Asp189、Arg192、Gln193 and Glu126 formed an adjacent region, which participated in the interaction of proteins or nucleotides. These residues among influenza virus type A or B and corresponding residues in influenza virus C were shown in FIG. 1, respectively.

Preferably, in a three-dimensional structure of PA_N of SEQ ID NO: 7 from influenza virus type A RNA polymerase, α-helix 1 and α-helix 2 formed a hairpin structure. Among residues Glu2、Asp3、Arg6、Gln10、Glu15、Glu18、Lys19、Lys22、Asp27 and Lys29, some of them formed a charged adjacent surface. These residues among influenza virus type A or B and corresponding residues in influenza virus C were shown in FIG. 1, respectively.

Second, present invention discloses that in the three-dimensional structure of PA_N of SEQ ID NO: 7 from influenza virus type A RNA polymerase, among residues Glu80、Asp108、His41、Glu119、Leu106 and Pro107, at least two, or at least three residues, at optimized conditions, can form a group and bind to peptides, proteins, inorganic or organic substances, antibodies or immune conjugates. Influenza viruses used in the present invention were chosen from influenza virus type A, B and C. And influenza viruses optimized were from influenza virus type A: strain A/goose/Guangdong/1/96 (SEQ ID NO:1), and strain A/Brevig Mission/1/1918 (SEQ ID NO:8), type B: strain B/Ann Arbor/1/1966 (SEQ ID NO:3), and type C: strain C/JJ/1950 (SEQ ID NO:4). Residues of influenza virus A or B and corresponding residues of influenza virus C were shown in FIG. 1, respectively. In the crystal structure, among residues Glu80、Asp108、His41、Glu119、Leu106 and Pro107, at least two residues, or at-least three residues, at optimized conditions, can bind to peptides, proteins, antibodies or immune conjugates. And the atomic coordinates on carbon skeleton of these two or three or more residues showed less than or equal to 1.7 Å of average variance, compared to the atomic coordinates listed in Table 1.

Third, present invention discloses that in the three-dimensional structure of P_N of SEQ ID NO: 7 from influenza virus type A RNA polymerase, among the residues Glu2、Asp3、Arg6、Gln10、Glu15、Glu18、Lys19、Lys22、Asp27 and Lys29, at least two, or at least three residues at optimized conditions, can form a group and bind to peptides, proteins, inorganic or organic substances, antibodies or immune conjugates. The residues of influenza virus type A or B and corresponding residues of influenza virus C were shown in FIG. 1, respectively. In the crystal structure, among the residues Glu2、Asp3、Arg6、Gln10、Glu15、Glu18、Lys19、Lys22、Asp27 and Lys29, at least two residues, or at least three residues at optimized conditions, can bind to peptides, proteins, antibodies or immune conjugates. And the atomic coordinates on carbon skeleton of these two or three or more residues showed less than or equal to 1.7 Å of average variance, compared to the atomic coordinates listed in Table 1.

Fourth, present invention discloses that in the three-dimensional structure of PA_N of SEQ ID NO: 7 from influenza virus type A RNA polymerase, among the resides Arg179、Asp189、Arg192、Gln193 and Glu126, at least two, or at least three residues at optimized conditions, can form a group and bind to the peptides, proteins, inorganic or organic substances, antibodies or immune conjugates. The residues of influenza virus type A or B and corresponding residues of influenza virus C were shown respectively in FIG. 1. In the crystal structure, among the residues Arg179、Asp189、Arg192、Gln193 and Glu126, at least two residues, or at least three residues at optimized conditions, can bind to peptides, proteins, antibodies or immune conjugates. And the atomic coordinates on carbon skeleton of these two or three or more residues showed less than or equal to 1.7 Å of average variance, compared to the atomic coordinates listed in Table 1.

Fifth, present invention discloses that in the three-dimensional structure of PA_N of SEQ ID NO: 7 from influenza virus type A RNA polymerase, among the resides T157、E153、E154、K158、D160、E165、E166、R168、R170 and Lys172, at least two, or at least three residues at optimized conditions, can form a group and bind to the peptides, proteins, inorganic or organic substances, antibodies or immune conjugates. The residues of influenza virus type A or B and corresponding residues of influenza virus C were shown in FIG. 1, respectively, In the crystal structure, among the residues T157、E153、E154、K158、D160、E165、E166、R168、R170 and Lys172, at least two of them, or at least three of them at optimized conditions, can bind to peptides, proteins, antibodies or immune conjugates. And the atomic coordinates on carbon skeleton of these two or three or more residues showed less than or equal to 1.7 Å of average variance, compared to the atomic coordinates listed in Table 1.

Sixth, present invention discloses the peptides, proteins, inorganic or organic substances, antibodies, immune conjugates, and, preferably, vehicles or excipients, which can bind to at least two, or at least three residues of PA_N SEQ ID NO: 7 of influenza virus type A RNA polymerase at optimized conditions.

Seventh, present invention discloses the application of above complex on the development of anti-influenza viral drugs.

Eighth, present invention discloses application of the three-dimensional structure of PA_N of SEQ ID NO: 7 from influenza virus type A RNA polymerase on designing and screening the peptides, proteins, antibodies or immune conjugates to develop the anti-influenza viral drugs.

The following were included in above applications: based on protein dimensional structure coordinates, using computer simulation to design the peptides, proteins, inorganic or organic compounds, antibodies or immune conjugates which bound to a specific site of influenza virus type A RNA polymerase;

Based on protein dimensional structure coordinates, using computer simulation to screen the peptides, proteins, inorganic or organic compounds, antibodies or immune conjugates which bound to a specific site of influenza virus type A RNA polymerase;

Integrate any peptides, proteins, inorganic or organic compounds, antibodies or immune conjugates which were designed or screened, based on protein three-dimensional structural coordinates, into any subtype of influenza virus RNA polymerase which contained a more than 50% similar sequence as influenza virus type A RNA polymerase described above, and analyze the integration.

Integrate any peptides, proteins, inorganic or organic compounds, antibodies or immune conjugates which were designed or screened, based on protein three-dimensional structural coordinates, into any subtype of influenza virus RNA polymerase which contained a more than 50% similar sequence as PA_N of SEQ LD NO: 7 of influenza virus type A RNA polymerase, crystallize peptides, proteins, inorganic or organic compounds, antibodies or immune conjugates, and analyze the integration of peptides or compounds with proteins through analyzing the three-dimensional structure obtained by the crystal diffraction method.

Candidate any peptides, proteins, inorganic or organic compounds, antibodies or immune conjugates as potential compounds which have at least 50% similar sequence as PA_N of SEQ ID NO: 7 of influenza virus type A RNA polymerase.

Ninth, present invention discloses that in the three-dimensional structure of three subunits PA, PB1 and PB2, or complex of PA, PB1 and PB2 from any subtype of influenza virus RNA polymerases, one of the proteins or regions, contains at least a 40% similar sequence as PA_N of SEQ ID NO: 7 of influenza virus type A RNA polymerase.

Tenth, present invention discloses that in the three-dimensional structure of three subunits PA, PB1 and PB2, or the complex of PA, PB1 and PB2 from any subtype of influenza virus RNA polymerases, at least 40% of atomic coordinates on the carbon skeleton showed less than or equal to 1.7 ∈ of average variance, compared to the atomic coordinates of PA_N of SEQ ID NO: 7 of influenza virus type A RNA polymerase.

Eleventh, present invention discloses that one peptide or small molecule had an interaction with any of the amino acids on PA_N of SEQ ID NO: 7 of influenza virus type A RNA polymerase.

Twelfth, present invention discloses the application of the three-dimensional structure of PA_N of SEQ ID NO: 7 of influenza virus type A RNA polymerase on drug screening and drug designing.

Thirteenth, present invention discloses the methods for screening peptides, proteins, inorganic or organic compounds, antibodies or immune conjugates which can bind to protein, based on the three-dimensional structure of PA_N of SEQ ID NO: 7 from influenza virus type A RNA polymerase. These included the methods to acquire a crystal containing PA_N of SEQ ID NO: 7 region, or methods to acquire the three- dimensional protein structure of the crystal containing PA_N of SEQ ID NO: 7 region. All three-dimensional protein structures above were defined as having less than or equal to 1.7 Å of average variance of atomic coordinates on carbon skeleton, compared to 40% of PA_N of SEQ ID NO: 7 from influenza virus type A RNA polymerase.

Fourteenth, present invention discloses the methods for screening peptides, proteins, inorganic or organic compounds, antibodies or immune conjugates which can bind to protein, based on the three-dimensional structure of PA_N of SEQ ID NO: 7 from influenza virus type A RNA polymerase. These include the application of a three dimensional protein structure which contains at least three same residues from the three-dimensional structure of PA_N of SEQ ID NO: 7 from influenza virus type A RNA polymerase, or from the peptides which can bind to peptides, proteins, inorganic or organic compounds, antibodies or immune conjugates above, and equal to 1.7 Å of average variance of atomic coordinates on carbon skeleton, on the screening peptides, proteins, inorganic or organic compounds, antibodies or immune conjugates.

BRIEF DESCRIPTION OF THE DRAWINGS

The patent or application file contains at least one drawing executed in color. Copies of this patent or patent application publication with color drawing(s) will be provided by the Office upon request and payment of necessary fee.

DETAILED DESCRIPTION OF THE INVENTION

Figure 1:
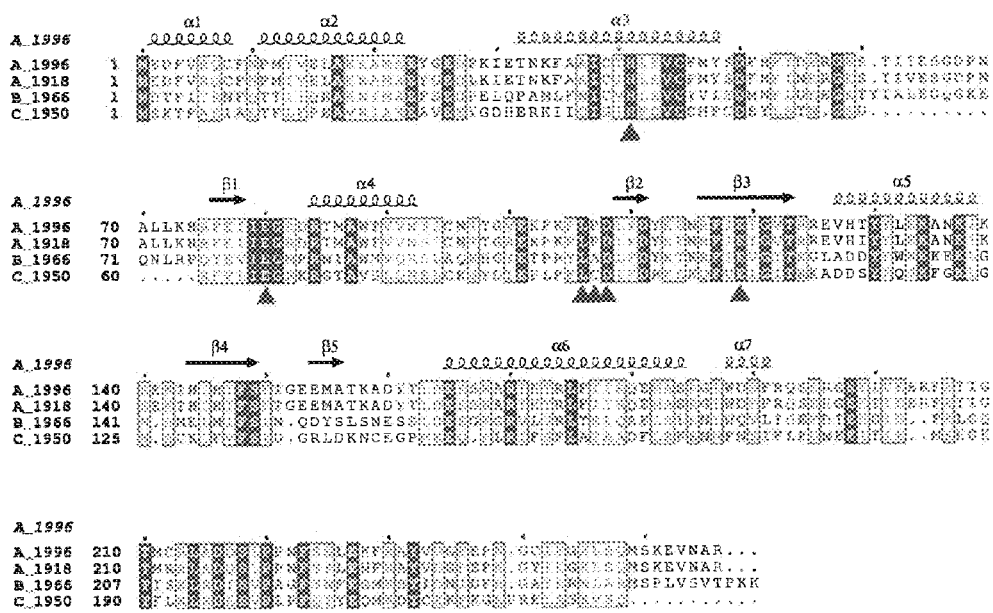
FIG. 1. Comparison of sequence of PA_N from three influenza viruses. A_1996: N-terminal sequences residues 1-257 of PA_N of SEQ ID NO: 1 from influenza virus type A strain, A/goose/Guangdong/1/96 of SEQ ID NO: 1; A_1918: N-terminal sequences residues 1-257 of PA_N from influenza virus type A strain, A/Brevig Mission/1/1918 of SEQ ID NO:8, which was a widely-circulating outbreak that caused the death of millions of people in Europe in 1918; B_1966: N-terminal sequences residues 1-257 of PA_N of SEQ ID NO: 3 from influenza virus type B strain B/Ann Arbor/1/1966; C_1950: N-terminal sequences residues 1-229 of PA_N of SEQ ID NO: 4 from influenza virus type C strain C/JJ/1950. Results showed highly conserved amino acid residues on N-terminal sequences of PA_N of SEQ ID NO: 1 from influenza virus. ". . . " indicates the gene depletion in corresponding sites. In manual and claim, locus of specific amino acid was presented in the case A_1996. A_1966 and A_OURS in FIG. 4 were the same N-terminal sequences of PA_N of SEQ ID NO: 1 from influenza virus type A strain A/goose/Guangdong/1/96. A_OURS in FIG. 4 was C-terminal sequences of PA_N from influenza virus type A strain A/goose/Guangdong/1/96.

Here inventors revealed the three-dimensional structure of the remaining region of PA (PA_N of SEQ ID NO: 7) by X-ray crystallography at a 2.2 Å resolution.

In the first embodiment, present invention discloses the three-dimensional structure of N-terminal region of PA (PA_N of SEQ ID NO:1) from one of influenza virus RNA polymerase. PA_N of SEQ ID NO: 1 is the residues 1~50 to 150~300 of influenza virus polymerase subunit PA. In the three-dimensional structure, at least 40% of atoms showed the same atomic coordinates, compared to that listed in Table 1. In other words, in the three-dimensional structure of influenza virus polymerase subunit PA_N of SEQ ID NO: 7, 40% of atomic coordinates on carbon skeleton of the amino acids of influenza virus polymerase subunit PA_N of SEQ ID NO: 7, showed less than or equal to 1.7 Å of average variance, compared to the atomic coordinates listed in Table 1.

In an optimal embodiment, influenza viruses used in this invention were from influenza virus type A, B and C. And optimized influenza viruses were from influenza virus type A: strain A/goose/Guangdong/1/96 of SEQ ID NO:1, and strain A/Brevig Mission/1/1918 of SEQ ID NO:8, type B: strain B/Ann Arbor/1/1966 of SEQ ID NO:3, and type C: strain C/JJ/1950 of SEQ ID NO:4.

In another optimal embodiment, the parental crystal had a P1 space group, and cell parameters: a=51.1 Å, b=151.0 Å, c=59.8 Å, α=96.6°, β=96.8°, γ=109.5°. The selenomethionine labeled crystal had a P6(4)22 space group, and cell parameters: α=b=73.8 Å, c=123.4 Å, α=β=90°, γ=120°.

In an optimal embodiment, PA_N of SEQ ID NO:7, structure has an α/β architecture with seven α-helices, α-helix 1: residues 2-9; α-helix 2: residues 11-22; α-helix 3: residues 32-48; α-helix 4: residues 84-92; α-helix 5: residues 127-138; α-helix 6: residues165-184; α-helix7: residues 187-191, and five β-sheets, β-sheet 1: residues 76-78; β-sheet 2: residues 109-111; β-sheet 3: residues 116-123; β-sheet 4: residues 144-149 and β-sheet 5: residues 154-157. Five parallel β-sheets formed a twisted plane surrounded by seven α-helices. Amino acids residues in influenza virus type A or B shown here, and the corresponding residues in influenza virus type C were listed in FIG. 1.

In another optimal embodiment, in the center of the three-dimensional structure of PA_N of SEQ m NO: 7 from influenza virus type A RNA polymerase, there was a binding metal ion, which was probably one of the following: magnesium, manganese, zinc, cuprum, cobalt or iron. And this metal is directly coordinated by the following ligands: three water molecules, the acidic residues Glu80 and/or Asp108, and at least one acidic residue among the residues His41, Glu119, Leu106 and Pro107. All six amino acids involved in coordinating this metal among influenza virus type A or B and corresponding residues in influenza virus C were shown in FIG. 1. More preferably, the metal mentioned above was identified as magnesium.

In an optimal embodiment, in a three-dimensional structure of PA_N of SEQ ID NO: 7 from influenza virus type A RNA polymerase, there was motif residues $P_{107}D_{108}X(11)E_{119}X(15)K_{134}$, which were similar to motif residues $(P)DX_N(D/E)XK$ among the endonuclease. These residues in influenza virus type A or B and corresponding residues in influenza virus C were shown in FIG. 1, respectively.

In another optimal embodiment, T157、E153、E154、K158、D160、E165、E166、R168、R170 and Lys172 were located at the residues between β-sheet4 and α-helix7. These amino acid residues among influenza virus type A or B and corresponding residues in influenza virus C were shown in FIG. 1, respectively.

In an optimal embodiment, at least two or three residues among Arg179、Asp189、Arg192、Gln193 and Glu126 formed an adjacent region, which participated in the interaction of proteins or nucleotides, in the three-dimensional structure of PA_N of SEQ ID NO: 7 from influenza virus type A RNA polymerase. These residues among influenza virus type A or B and corresponding residues in influenza virus C were shown in FIG. 1, respectively.

In another optimal embodiment, α-helix 1 and α-helix 2 formed a hairpin structure in the three-dimensional structure of PA _N SEQ ID NO: 7 from influenza virus type A RNA polymerase. Among the amino acid residues Glu2、Asp3、Arg6、Glu10、Glu15、Glu18、Lys19、Lys22、Asp27 and Lys29, some of them formed a charged adjacent surface. These amino acid residues among influenza virus type A or B and corresponding residues in influenza virus C were shown in FIG. 1, respectively.

In the second embodiment, present invention discloses that in the three-dimensional structure of PA_N of SEQ ID NO: 7 from influenza virus type A RNA polymerase, among the resides Glu80、Asp108、His41、Glu119、Leu106 and Pro107, at least two, or at least three residues at optimized condition can form a group and bind to the peptides, proteins, inorganic or organic substances, antibodies or immune conjugates. Influenza viruses used in this invention were chosen from influenza virus type A, B and C. And influenza viruses optimized were from influenza virus type A: strain A/goose/Guangdong/1/96 (SEQ ID NO:1), and strain A/Brevig Mission/1/1918 (SEQ ID NO:8), type B: strain B/Ann Arbor/1/1966 (SEQ ID NO:3), and type C: strain C/JJ/1950 (SEQ ID NO:4). The residues in influenza virus type A or B and corresponding residues in influenza virus C were shown respectively in FIG. 1. In the crystal structure, among the residues Glu80、Asp108、His41、Glu119、Leu106 and Pro107, at least two residues, or at least three of them at optimized conditions can bind to peptides, proteins, antibodies or immune conjugates. And the atomic coordinates on carbon skeleton of these two or three or more residues showed less than or equal to 1.7 Å of average variance, compared to the atomic coordinates listed in Table 1.

In the third embodiment, present invention discloses that in the three-dimensional structure of PA_N of SEQ ID NO: 7 from influenza virus type A RNA polymerase, among the resides Glu2、Asp3、Arg6、Gln10、Glu15、Glu18、Lys19、Lys22、Asp27and Lys29, at least two, or at least three residues at optimized conditions can form a group and bind to the peptides, proteins, inorganic or organic substances, antibodies or immune conjugates. The amino acid residues among influenza virus type B or C and the corresponding residues in influenza virus C were shown in FIG. 1, respectively. In the crystal structure, among the residues Glu2、Asp3、Arg6、Gln10、Glu15、Glu18、Lys19、Lys22、Asp27and Lys29, at least two residues, or at least three residues at optimized conditions, can bind to peptides, proteins, antibodies or immune conjugates. The atomic coordinates on carbon skeleton of these two or three or more residues showed less than or equal to 1.7 Å of average variance, compared to the atomic coordinates listed in Table 1.

In the fourth embodiment, present invention discloses that in the three-dimensional structure of PA_N of SEQ ID NO: 7 from influenza virus type A RNA. polymerase, among the resides Arg179、Asp189、Arg192、Gln193 and Glu126, at least two, or at least three residues at optimized conditions can form a group and bind to the peptides, proteins, inorganic or organic substances, antibodies or immune conjugates. The residues in influenza virus type A or B and corresponding residues in influenza virus C were shown in FIG. 1, respectively. In the crystal structure, among residues Arg179、Asp189、Arg192、Gln193 and Glu126, at least two residues, or at least three residues at optimized conditions, can bind peptides, proteins, antibodies or immune conjugates. And the atomic coordinates on carbon skeleton of these two or three or more residues showed less than or equal to 1.7 Å of average variance, compared to the atomic coordinates listed in Table 1.

In the fifth embodiment, present invention discloses that in the three-dimensional structure of PA_N of SEQ ID NO: 7 from influenza virus type A RNA polymerase, among the resides T157、E153、E154、K158、D160、E165、E166、R168、R170 and Lys172, at least two, or at least three residues at optimized conditions can form a group and bind to peptides, proteins, inorganic or organic substances, antibodies or immune conjugates. The residues in influenza virus type A or B and corresponding residues in influenza virus C were shown in FIG. 1, respectively. In the crystal structure, among residues T157、E153、E154、K158、D160、E165、E166、R168、R170 and Lys172, at least two residues, or at least three residues at optimized conditions, can bind to peptides, proteins, antibodies or immune conjugates. And the atomic coordinates on carbon skeleton of these two or three or more residues showed less than or equal to 1.7 Å of average variance, compared to the atomic coordinates listed in Table 1.

In the sixth embodiment, present invention discloses the peptides, proteins, inorganic or organic substances, antibodies, immune conjugates, and preferably vehicles or excipients, which can bind to at least two residues, or at least three residues of PA_N of SEQ ID NO: 7 of influenza virus type A RNA polymerase at optimized conditions.

In the seventh embodiment, present invention discloses the application of the above complex on the development of anti-influenza viral drugs.

In the eighth embodiment, present invention discloses the application of the three-dimensional structure of PA_N of SEQ ID NO: 7 from influenza virus type A RNA polymerase on the designing and screening of the peptides, proteins, antibodies or immune conjugates to develop the anti-influenza viral drugs.

The following applications were included: based on the protein dimensional structural coordinates, using computer simulation to design peptides, proteins, inorganic or organic compounds, antibodies or immune conjugates which bind to the specific site of influenza virus type A RNA polymerase;

Based on protein dimensional structure coordinates, using computer simulation to screen the peptides, proteins, inorganic or organic compounds, antibodies or immune conjugates which bound to the specific site of the influenza virus type A RNA polymerase;

Integrate peptides, proteins, inorganic or organic compounds, antibodies or immune conjugates which were designed or screened, based on the protein dimensional structure coordinates, into any subtype of influenza virus RNA polymerase which contain a more than 50% similar sequence as influenza virus type A RNA polymerase described above, and analyze the integration.

Integrate peptides, proteins, inorganic or organic compounds, antibodies or immune conjugates which were designed or screened, based on the protein dimensional structure coordinates, into any subtype of influenza virus RNA polymerase which contain more than 50% similar sequence as PA_N of SEQ ID NO: 7 from influenza virus type A RNA polymerase, crystallize peptides, proteins, inorganic or organic compounds, antibodies or immune conjugates, and analyze the integration of peptides or compounds with proteins through analyzing the three-dimensional structure obtained by the crystal diffraction method.

Candidate peptides, proteins, inorganic or organic compounds, antibodies or immune conjugates as the potential compounds which have at least a 50% similar sequence as PA_N of SEQ ID NO: 7 of influenza virus type A RNA polymerase.

In the ninth embodiment, present invention discloses that in the three-dimensional structure of three subunits PA、PB1 and PB2, or complex of PA、PB1 and PB2 from any subtype of influenza virus RNA polymerases, one of the proteins or regions, contains at least 40% sequence as PA_N of SEQ ID NO: 7 of influenza virus type A RNA polymerase.

In the tenth embodiment, present invention discloses that in the three-dimensional structure of three subunits PA, PB1 and PB2, or complex of PA、PB1 and PB2 from any subtype of influenza virus RNA polymerases, at least 40% of atomic coordinates on the carbon skeleton showed less than or equal to 1.7 Å of average variance, compared to the atomic coordinates of PA_N of SEQ ID NO: 7 from influenza virus type A RNA polymerase.

In the eleventh embodiment, present invention discloses that one peptide or micro molecule interacts with any residue of PA_N of SEQ ID NO: 7 from influenza virus type A RNA polymerase.

In the twelfth embodiment, present invention discloses the application of the three-dimensional structure of PA_N of SEQ ID NO: 7 from influenza virus type A RNA polymerase on drug screening and drug designing.

In the thirteenth embodiment, present invention discloses the methods for screening peptides, proteins, inorganic or organic compounds, antibodies or immune conjugates which can bind to protein, based on the three-dimensional structure of PA_N of SEQ ID NO: 7 from influenza virus type A RNA polymerase. These included the method to acquire the crystal containing PA_N of SEQ ID NO: 7 region, or methods to acquire a three dimensional protein structure of crystal containing of PA_N SEQ ID NO: 7 region. All three dimensional protein structures above were defined as having less than or equal to 1.7 Å of average variance of atomic coordinates on carbon skeleton, compared to 40% of the PA_N of SEQ ID NO: 7 from influenza virus type A RNA polymerase.

In the fourteenth embodiment, present invention discloses the methods for screening peptides, proteins, inorganic or organic compounds, antibodies or immune conjugates which can bind to protein, based on the three-dimensional structure of PA_N of SEQ ID NO: 7 front influenza virus type A RNA polymerase. These include the applications of three dimensional protein structures which contained at least three same residues of the three-dimensional structure of PA_N of SEQ ID NO: 7 from influenza virus type A RNA polymerase, or from peptides which can bind to peptides, proteins, inorganic or organic compounds, antibodies or immune conjugates above, and equal to 1.7 Å of average variance of atomic coordinates on carbon skeleton, on screening the peptides, proteins, inorganic or organic compounds, antibodies or immune conjugates.

Expression and Purification of PA_N Protein of Avian Flu:

Protein sequence of avian flu A/goose/Guangdong/1/96 were:

```
Sequence for protein PA:
                                                                  (SEQ ID NO: 1)
MEDFVRQCFNPMIVELAEKAMKEYGEDPKIETNKFAAICTHLEVCFM

YSDFHFIDERGESTIIESGDPNALLKHRFEIIEGRDRTMAWTVVNSICNT

TGVEKPKFLPDLYDYKENRFIEIGVTRREVHTYYLEKANKIKSEKTHIH

IFSFTGEEMATKADYTLDEESRARIKTRLFTIRQEMASRGLWDSFRQSE

RGEETIEERFEITGTMCRLADQSLPPNFSSLEKFRAYVDGFEPNGCIEG

KLSQMSKEVNARIEPFLKTTPRPLRLPDGPPCSQRSKFLLMDALKLSIE

DPSHEGEGIPLYDAIKCMKTFFGWKEPNIVKPHEKGINPNYLLAWKQV

LAELQDIENEEKIPKTKNMRKTSQLKWALGENMAPEKVDFEDCKDVS

DLRQYDSDEPKPRSLASWIQSEFNKACELTDSSWIELDEIGEDVAPIEHI

ASMRRNYFTAEVSHCRATEYIMKGVYINTALLNASCAAMDDFQLIPM

ISKCRTKEGRRKTNLYGFIIKGRSHLRNDTDVVNFVSMEFSLTDPRLEP

HKWEKYCVLEIGDMLLRTAIGQVSRPMFLYVRTNGTSKIKMKWGME

MRRCLLQSLQQIESMIEAESSVKEKDMTKEFFENKSETWPIGESPKGM

EEGSIGKVCRTLLAKSVFNSLYASPQLEGFSAESRKLLLIVQALRDNLE

PGTFDLGGLYEAIEECLINDPWVLLNASWFNSFLTHALK;

Also:
Met Glu Asp Phe Val Arg Gln Cys Phe Asn Pro Met Ile Val Glu Leu Ala Glu

Lys Ala Met Lys Glu Tyr Gly Glu Asp Pro Lys Ile Glu Thr Asn Lys Phe Ala Ala Ile

Cys Thr His Leu Glu Val Cys Phe Met Tyr Ser Asp Phe His Phe Ile Asp Glu Arg

Gly Glu Ser Thr Ile Ile Glu Ser Gly Asp Pro Asn Ala Leu Leu Lys His Arg Phe Glu

Ile Ile Glu Gly Arg Asp Arg Thr Met Ala Trp Thr Val Val Asn Ser Ile Cys Asn Thr

Thr Gly Val Glu Lys Pro Lys Phe Leu Pro Asp Leu Tyr Asp Tyr Lys Glu Asn Arg

Phe Ile Glu Ile Gly Val Thr Arg Arg Glu Val His Thr Tyr Tyr Leu Glu Lys Ala Asn

Lys Ile Lys Ser Glu Lys Thr His Ile His Ile Phe Ser Phe Thr Gly Glu Glu Met Ala

Thr Lys Ala Asp Tyr Thr Leu Asp Glu Glu Ser Arg Ala Arg Ile Lys Thr Arg Leu Phe

Thr Ile Arg Gln Glu Met Ala Ser Arg Gly Leu Trp Asp Ser Phe Arg Gln Ser Glu Arg

Gly Glu Glu Thr Ile Glu Glu Arg Phe Glu Ile Thr Gly Thr Met Cys Arg Leu Ala

Asp Gln Ser Leu Pro Pro Asn Phe Ser Ser Leu Glu Lys Phe Arg Ala Tyr Val Asp

Gly Phe Glu Pro Asn Gly Cys Ile Glu Gly Lys Leu Ser Gln Met Ser Lys Glu Val

Asn Ala Arg Ile Glu Pro Phe Leu Lys Thr Thr Pro Arg Pro Leu Arg Leu Pro Asp

Gly Pro Pro Cys Ser Gln Arg Ser Lys Phe Leu Leu Met Asp Ala Leu Lys Leu Ser

Ile Glu Asp Pro Ser His Glu Gly Glu Gly Ile Pro Leu Tyr Asp Ala Ile Lys Cys Met

Lys Thr Phe Phe Gly Trp Lys Glu Pro Asn Ile Val Lys Pro His Glu Lys Gly Ile Asn

Pro Asn Tyr Leu Leu Ala Trp Lys Gln Val Leu Ala Glu Leu Gln Asp Ile Glu Asn

Glu Glu Lys Ile Pro Lys Thr Lys Asn Met Arg Lys Thr Ser Gln Leu Lys Trp Ala Leu
```

-continued

Gly Glu Asn Met Ala Pro Glu Lys Val Asp Phe Glu Asp Cys Lys Asp Val Ser Asp
Leu Arg Gln Tyr Asp Ser Asp Glu Pro Lys Pro Arg Ser Leu Ala Ser Trp Ile Gln Ser
Glu Phe Asn Lys Ala Cys Glu Leu Thr Asp Ser Ser Trp Ile Glu Leu Asp Glu Ile Gly
Glu Asp Val Ala Pro Ile Glu His Ile Ala Ser Met Arg Arg Asn Tyr Phe Thr Ala Glu
Val Ser His Cys Arg Ala Thr Glu Tyr Ile Met Lys Gly Val Tyr Ile Asn Thr Ala Leu
Leu Asn Ala Ser Cys Ala Ala Met Asp Asp Phe Gln Leu Ile Pro Met Ile Ser Lys Cys
Arg Thr Lys Glu Gly Arg Arg Lys Thr Asn Leu Tyr Gly Phe Ile Ile Lys Gly Arg Ser
His Leu Arg Asn Asp Thr Asp Val Val Asn Phe Val Ser Met Glu Phe Ser Leu Thr
Asp Pro Arg Leu Glu Pro His Lys Trp Glu Lys Tyr Cys Val Leu Glu Ile Gly Asp
Met Leu Leu Arg Thr Ala Ile Gly Gln Val Ser Arg Pro Met Phe Leu Tyr Val Arg Thr
Asn Gly Thr Ser Lys Ile Lys Met Lys Trp Gly Met Glu Met Arg Arg Cys Leu Leu
Gln Ser Leu Gln Gln Ile Glu Ser Met Ile Glu Ala Glu Ser Ser Val Lys Glu Lys Asp
Met Thr Lys Glu Phe Phe Glu Asn Lys Ser Glu Thr Trp Pro Ile Gly Glu Ser Pro Lys
Gly Met Glu Glu Gly Ser Ile Gly Lys Val Cys Arg Thr Leu Leu Ala Lys Ser Val Phe
Asn Ser Leu Tyr Ala Ser Pro Gln Leu Glu Gly Phe Ser Ala Glu Ser Arg Lys Leu
Leu Leu Ile Val Gln Ala Leu Arg Asp Asn Leu Glu Pro Gly Thr Phe Asp Leu Gly
Gly Leu Tyr Glu Ala Ile Glu Glu Cys Leu Ile Asn Asp Pro Trp Val Leu Leu Asn Ala
Ser Trp Phe Asn Ser Phe Leu Thr His Ala Leu Lys.

Sequence for protein PB1: (SEQ ID NO: 2)

MDVNPTLLFLKVPAQNAISTTFPYTGDPPYSHGTGTGYTMDTVNRTHQYSE

KGKWTTNTETGAPQLNPIDGPLPEDNEPSGYAQTDCVLEAMAFLEKSHPGI

FENSCLETMEIVQQTRVDKLTQGRQTYDWTLNRNQPAATALANTIEVFRSN

GLTANESGRLIDFLKDVMESMDKGEMEIITHFQRKRRVRDNMTKKMVTQR

TIGKKKQRLNKRSYLIRALTLNTMTKDAERGKLKRRAIATPGMQIRGFVYF

VETLARSICEKLEQSGLPVGGNEKKAKLANVVRKMMTNSQDTELSFTITGD

NTKWNENQNPRMFLAMITYITRNQPEWFRNVLSIAPIMFSNKMARLGKGY

MFESKSMKLRTQIPAEMLASIDLKYFNESTRKKIEKIRPLLIDGTASLSPGMM

MGMFNMLSTVLGVSILNLGQKRYTKTTYWWDGLQSSDDFALIVNAPNHEG

IQAGVDRFYRTCKLVGINMSKKKSYINRTGTFEFTSFFYRYGFVANFSMELP

SFGVSGINESADMSIGVTVIKNNMINNDLGPATAQMALQLFIKDYRYTYRCH

RGDTQIQTRRSFELKKLWEQTRSKAGLLVSDGGPNLYNIRNLHIPEVCLKWE

LMDEDYQGRLCNPLNPFVSHKEIESVNNAVVMPAHGPAKSMEYDAVATTHS

WIPKRNRSILNTSQRGILEDEQMYQKCCNLFEKFFPSSSYRRPVGISSMVEA

MVSRARIDARIDFESGRIKKEEFAEIMKICSTIEELRRQK;

Also:

Met Asp Val Asn Pro Thr Leu Leu Phe Leu Lys Val Pro Ala Gln Asn Ala Ile

Ser Thr Thr Phe Pro Tyr Thr Gly Asp Pro Pro Tyr Ser His Gly Thr Gly Thr Gly Tyr

Thr Met Asp Thr Val Asn Arg Thr His Gln Tyr Ser Glu Lys Gly Lys Trp Thr Thr

Asn Thr Glu Thr Gly Ala Pro Gln Leu Asn Pro Ile Asp Gly Pro Leu Pro Glu Asp

Asn Glu Pro Ser Gly Tyr Ala Gln Thr Asp Cys Val Leu Glu Ala Met Ala Phe Leu

Glu Lys Ser His Pro Gly Ile Phe Glu Asn Ser Cys Leu Glu Thr Met Glu Ile Val Gln

-continued

Gln Thr Arg Val Asp Lys Leu Thr Gln Gly Arg Gln Thr Tyr Asp Trp Thr Leu Asn

Arg Asn Gln Pro Ala Ala Thr Ala Leu Ala Asn Thr Ile Glu Val Phe Arg Ser Asn Gly

Leu Thr Ala Asn Glu Ser Gly Arg Leu Ile Asp Phe Leu Lys Asp Val Met Glu Ser

Met Asp Lys Gly Glu Met Glu Ile Ile Thr His Phe Gln Arg Lys Arg Arg Val Arg Asp

Asn Met Thr Lys Lys Met Val Thr Gln Arg Thr Ile Gly Lys Lys Lys Gln Arg Leu

Asn Lys Arg Ser Tyr Leu Ile Arg Ala Leu Thr Leu Asn Thr Met Thr Lys Asp Ala

Glu Arg Gly Lys Leu Lys Arg Arg Ala Ile Ala Thr Pro Gly Met Gln Ile Arg Gly Phe

Val Tyr Phe Val Glu Thr Leu Ala Arg Ser Ile Cys Glu Lys Leu Glu Gln Ser Gly Leu

Pro Val Gly Gly Asn Glu Lys Lys Ala Lys Leu Ala Asn Val Val Arg Lys Met Met

Thr Asn Ser Gln Asp Thr Glu Leu Ser Phe Thr Ile Thr Gly Asp Asn Thr Lys Trp

Asn Glu Asn Gln Asn Pro Arg Met Phe Leu Ala Met Ile Thr Tyr Ile Thr Arg Asn

Gln Pro Glu Trp Phe Arg Asn Val Leu Ser Ile Ala Pro Ile Met Phe Ser Asn Lys Met

Ala Arg Leu Gly Lys Gly Tyr Met Phe Glu Ser Lys Ser Met Lys Leu Arg Thr Gln

Ile Pro Ala Glu Met Leu Ala Ser Ile Asp Leu Lys Tyr Phe Asn Glu Ser Thr Arg Lys

Lys Ile Glu Lys Ile Arg Pro Leu Leu Ile Asp Gly Thr Ala Ser Leu Ser Pro Gly Met

Met Met Gly Met Phe Asn Met Leu Ser Thr Val Leu Gly Val Ser Ile Leu Asn Leu

Gly Gln Lys Arg Tyr Thr Lys Thr Thr Tyr Trp Trp Asp Gly Leu Gln Ser Ser Asp

Asp Phe Ala Leu Ile Val Asn Ala Pro Asn His Glu Gly Ile Gln Ala Gly Val Asp Arg

Phe Tyr Arg Thr Cys Lys Leu Val Gly Ile Asn Met Ser Lys Lys Lys Ser Tyr Ile Asn

Arg Thr Gly Thr Phe Glu Phe Thr Ser Phe Phe Tyr Arg Tyr Gly Phe Val Ala Asn

Phe Ser Met Glu Leu Pro Ser Phe Gly Val Ser Gly Ile Asn Glu Ser Ala Asp Met Ser

Ile Gly Val Thr Val Ile Lys Asn Asn Met Ile Asn Asn Asp Leu Gly Pro Ala Thr Ala

Gln Met Ala Leu Gln Leu Phe Ile Lys Asp Tyr Arg Tyr Thr Tyr Arg Cys His Arg

Gly Asp Thr Gln Ile Gln Thr Arg Arg Ser Phe Glu Leu Lys Lys Leu Trp Glu Gln

Thr Arg Ser Lys Ala Gly Leu Leu Val Ser Asp Gly Gly Pro Asn Leu Tyr Asn Ile Arg

Asn Leu His Ile Pro Glu Val Cys Leu Lys Trp Glu Leu Met Asp Glu Asp Tyr Gln

Gly Arg Leu Cys Asn Pro Leu Asn Pro Phe Val Ser His Lys Glu Ile Glu Ser Val Asn

Asn Ala Val Val Met Pro Ala His Gly Pro Ala Lys Ser Met Glu Tyr Asp Ala Val Ala

Thr Thr His Ser Trp Ile Pro Lys Arg Asn Arg Ser Ile Leu Asn Thr Ser Gln Arg Gly

Ile Leu Glu Asp Glu Gln Met Tyr Gln Lys Cys Cys Asn Leu Phe Glu Lys Phe Phe

Pro Ser Ser Ser Tyr Arg Arg Pro Val Gly Ile Ser Ser Met Val Glu Ala Met Val Ser

Arg Ala Arg Ile Asp Ala Arg Ile Asp Phe Glu Ser Gly Arg Ile Lys Lys Glu Glu Phe

Ala Glu Ile Met Lys Ile Cys Ser Thr Ile Glu Glu Leu Arg Arg Gln Lys

Using molecular techniques inventors cloned the N-terminal (residues 1-256 of SEQ ID NO:1) and C-terminal (residues 257-716 of SEQ ID NO:1) of PA gene from influenza virus RNA polymerase into pGEX-6p (Amersham Pharmacia Inc.) respectively, to express GST-fusion proteins (GST-PA-N and GST-PA$_C$). Express vectors were transformed into E. coli BL21, and bacteria were induced with 0.1-1 mM IPTG (Isopropyl β-D-1-thiogalactopyranoside) (See example 1 for detail).

Inventors cloned N-terminal gene fragment (residues 1-48 of SEQ ID NO:2) of PB gene from influenza virus RNA polymerase into pGEX-6p, and expressed GST-fusion GST-PB1$_N$ protein.

Using the same method, inventors cloned N-terminal gene fragment (residues 1-25 or 1-48 of SEQ ID NO:2) of PB gene from influenza virus RNA polymerase into pGEX-6p, transformed expressing vector into E. coli BL21 and induced the E. coli BL21 0.1-1 mM IPTG, to express GST-fusion protein.

Inventors cultured and harvested transformed E. coli BL21, resuspended and lysed the pellet, spun it down, harvested the supernatant and subjected it to affinity column to purify GST-PA-N fusion protein.

Inventors resuspended the GST-PA$_C$ expressing E. coli and GST-PB1 expressing E. coli with 20 mM Tris-HCl (pH8.0)/250 mM NaCl buffer or 1×PBS (pH7.4) buffer, respectively, mixed two suspensions of GST-PA$_C$ and GST-PB1 with mole ratio at 0.1:1~1:0.1, at 0.5:1~1:0.5, preferably at 1:1.

Inventors purified GST fusion protein with affinity column Glutathione-Sepharose (Amersham Pharmacia Inc.). After enzymolysis with PRESCISSION PROTEASE (Amersham Pharmacia Inc.), the peptide complex PA$_C$/PB1 was further purified with Superdex-200 and Q sepharose (Amersham Pharmacia Inc.). The purity was determined with SDS-PAGE, and subjected the protein to further crystal experiment.

Using the same procedure, GST fusion protein was purified with affinity column Glutathione-Sepharose (Amersham Pharmacia Inc.). After enzymolysis with PRESCISSION PROTEASE (Amersham Pharmacia Inc), peptide GST-PA-N was further purified with Superdex-200 and Q sepharose (Amersham Pharmacia Inc.). The purity was determined with SDS-PAGE, and subjected the protein to further crystal experiment.

Figure 2:
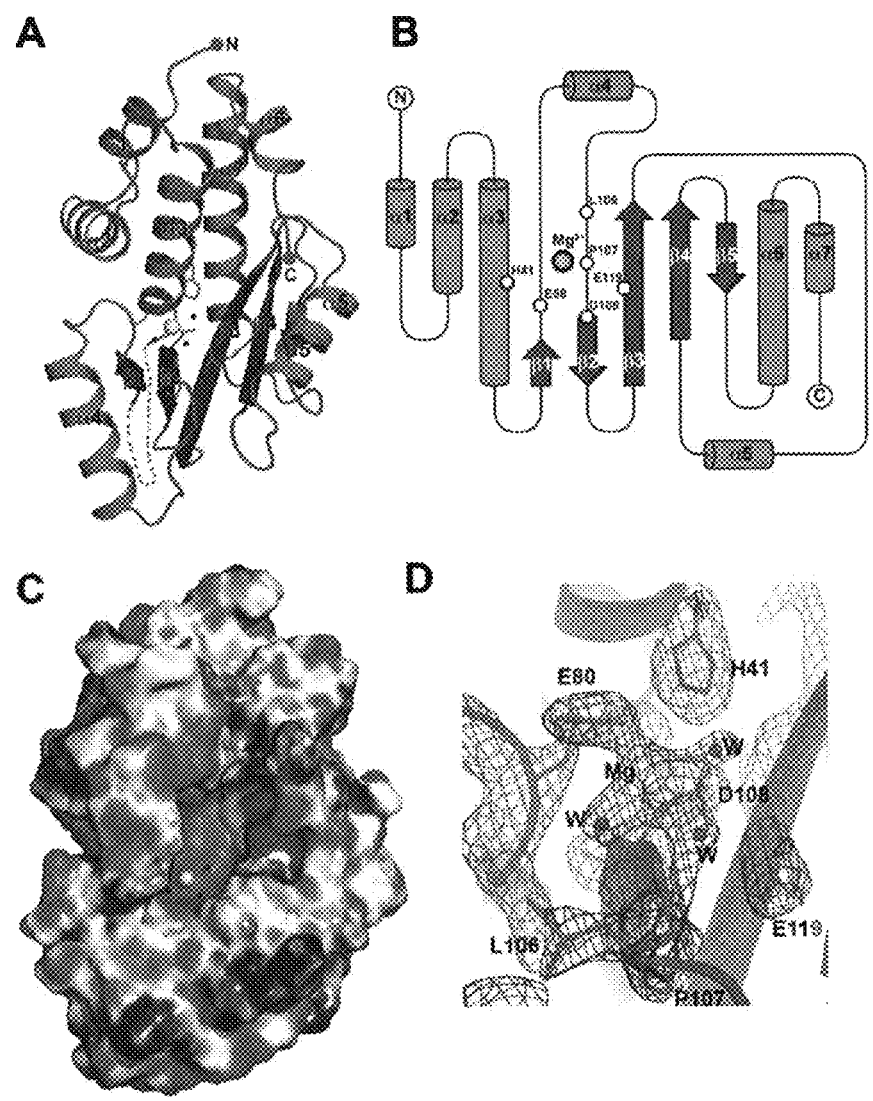
FIG. 2. Three-dimensional structure of PA_N of SEQ ID NO: 1 from RNA polymerase of influenza virus type A strain A/goose/Guangdong/1/96. (A), Ribbon representation showing the PA-N structure. The structure is colored according to secondary structure elements: α-helices are pink, β-sheets are magenta, and loops are green. Individual secondary structure elements are labeled. $Mg^{2+}$ ion is shown by a silver sphere and the three water molecules are indicated by black dots. (B), Topology figure of the PAN structure colored according to the scheme in (A). Ⓒ: C-terminal, Ⓝ: N-terminal. Circle indicates the amino acid residue. Solid circle indicates $Mg^{2+}$ ion. (C), Surface representation showing the same view of PA_N of SEQ ID NO: 1 as in (A), colored by electrostatic charge from red ($-10\ K_B T/e_c$, in which $K_B$ the Boltzmann constant, T is temperature and $e_c$ is the electron charge) to blue ($+10\ K_B T/e_c$). In the central area which is indicated by, color $Mg^{2+}$ ion is shown as a silver sphere and water molecules are shown by black spheres. Positively charged surface is indicated by blue, negatively charged surface is indicated by red, and uncharged amino acids are indicated by white. (D), Close-up view of the $Mg^{2+}$ binding site covered by a $2F_o$-$F_c$ electron density map (contoured at 1.5σ). Residues coordinating the $M^{2+}$ ion are shown in stick representation and labeled. The $M^{2+}$ ion is shown by a silver sphere and water molecules are shown by red spheres. The PA_N of SEQ ID NO: 1 structure is in the same orientation and colored according to the scheme in A.
Figure 3:
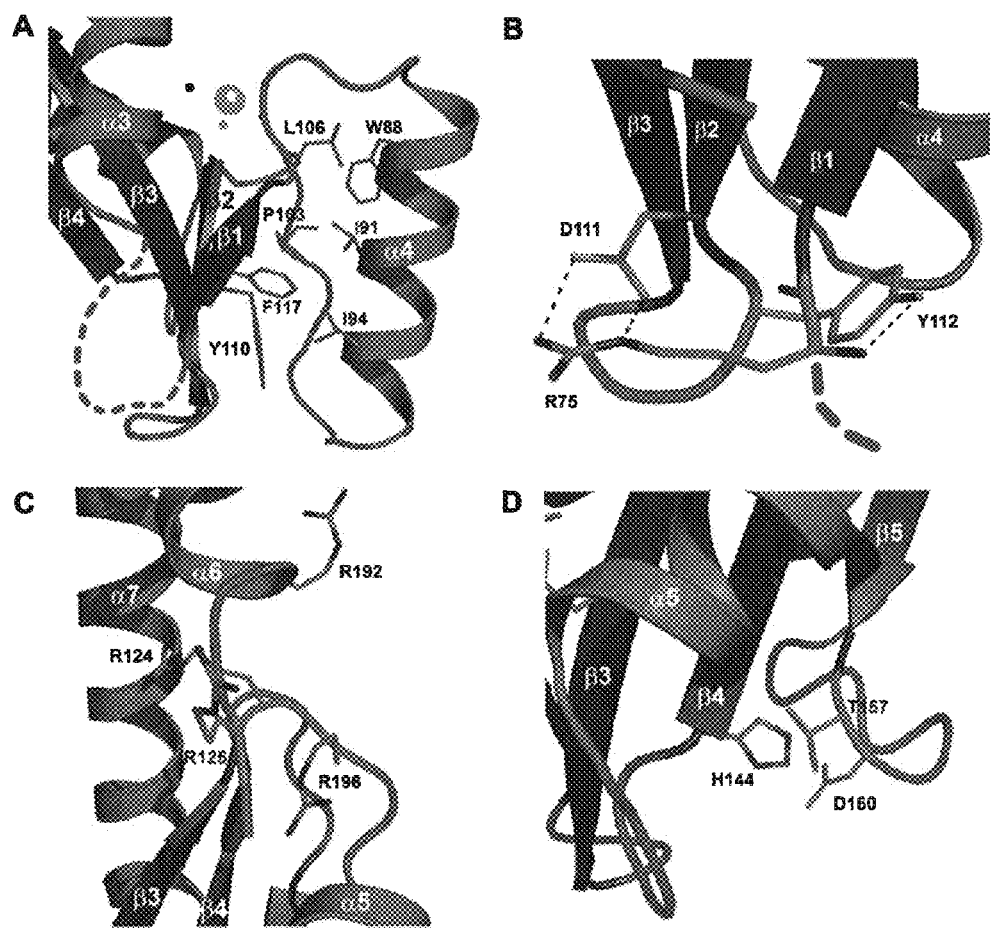
FIG. 3. Close-up view of ribbon representation for partial three-dimensional structure of PA_N of SEQ ID NO: 1 from RNA polymerase of influenza virus type A strain A/goose/Guangdong/1/96. $M^{2+}$ ion is shown by a silver sphere. Water molecules are indicated by black dots. Residues coordinating the $Mg^{2+}$ ion are shown in stick representation and labeled with red or blue.

(SEQ ID NO: 7) Sequence of the protein used for crystallization:
GPLGSMEDFVRQCFNPMIVELAEKA-MKEYGEDPKIETNKFAAICTHLEVC FMYSDFHFI-DERGESTHESGDPNALLKHRFE-HEGRDRTMAWTVVNSIC NTTGVEKPKFLPDLYDYKENRFIE-IGVTRREVHTYYLEKANKIKSEKTHI HIFSFT-GEEMATKADYTLDEESRARIKTRLFT-IRQEMASRGLWDSFRQSE RGEETIEERFEITGTMCRLADQSLPPNF-SSLEKFRAYVDGFEPNGCIEGK LSQMSKEVNAR;

A three-dimensional structure of the remaining region of PA (PA_N of SEQ ID NO:7) was revealed by X-ray crystallography as follows: PA_N of SEQ ID NO: 7 structure has an α/β architecture with five β-sheets (β1-5) seven α-helices (α1-7), like an open shell. Five parallel β-sheets (β1-5) formed a twisted plane surrounded by seven α-helices (α1-7), as shown in FIG. 2A. α-helices α2、 α4、 α5 and α7 formed the opened mouth of shell, and other α-helices and β-sheets formed the sharp-bottom and surface of the shell. α2-α5 and β3 surrounded a negatively charged cave which bound to a metal ion, which was probably magnesium, manganese, zinc, cuprum, cobalt or iron. And this metal was directly coordinated by following ligands: three water molecules, the acidic residues Glu80 and/or Asp108, and at least one acidic residue among the residues His41, Glu119, Leu106 and Pro107.

Preferably, the metal mentioned above was identified as magnesium. And Mg$^{2+}$ ion was directly coordinated by five ligands: acidic amino acid E80, D108 and three water molecules. Three water molecules formed the bonds to carbonyl oxygen of residues H41, E119, L106 and P107. These six residues bound to Mg$^{2+}$ ion were very conservative in the PA of influenza virus type A, B and C. It was only found that P107 was replaced by alanine or serine in influenza virus type B or C (see FIG. 1). According to the blast results from database Dali online program for 3D structural comparison, inventors found that PA_N of SEQ ID NO: 7 showed high similar structure compared to predicted nuclease Tt1808 from *Thermus thermophilus* Hb8 (PDB ID: 1WDJ, Z-score 4.8, r.m.s.d. 3.4 Å, compared with 87 residues of this nuclease), one well known restriction enzyme Sdal (PDB ID: 21XS, Z-score 3.9, r.m.s.d. 4.0 Å, compared with 95 residues of this enzyme), and Holliday junction resolvase Hjc (PDB ID: 1GEF, Z-score 3.8, r.m.s.d. 3.0 Å, compared with 76 residues of this resolvase).

Since these proteins contained a conserved (P) DX$_N$(D/E) XK active site, inventors proposed that PA_N of SEQ ID NO: 7 might contain endonuclease activity. The endonuclease activity of the influenza virus polymerase subunit is critical for snatching capped primers from host mRNA to initiate mRNA transcription. Inventors did the following biochemical and cell biological experiments to prove PA_N of SEQ ID NO: 7 was an endonuclease: 1) primer extension: transfected the plasmids which expressed PA, PB1 or PB2 into human embryonic kidney cell 293, and co-transfected the plasmids contained promoter of RNA polymerase of influenza virus at the same time. Expressed polymerase in 293 cells can identify and synthesize part of virus RNA. Polymerase activity was determined by detecting the types of virus RNA using primer extension assay in vitro.

2) Endonuclease activity and others. For example, inventors proved that mutation on predicted endonuclease activity sites H41, E80, L106, P107, D108 and E119, caused the loss of activity for snatching capped primers from host mRNA to initiate mRNA transcription, to different degrees. Polymerases with E80A, D108, E119A and K134A point mutations in PA showed background levels of mRNA synthesis, while retaining significant cRNA and vRNA synthesis activity, in comparison with wild-type polymerase, whereas H41A mutation showed no detectable synthesis of any of three viral RNAs. Notably, point mutations of the PB1 (SEQ ID NO: 2) residues, E508, E519 and D522, which have previously been claimed to be the polymerase endonuclease active centre, resulted in significant levels of activity. Sequence similarity searches did not identify a possible endonuclease activity motif around residues E508, E519 and D522 in PB1 (SEQ ID NO: 2). These observations strongly suggest that PA_N of SEQ ID NO: 7 provides a centre for polymerase endonuclease activity, whereas the binding site for residue on polymerase endonuclease depends on the subunits PB1 (SEQ ID NO: 2) and PB2. One possible RNA binding site could be formed by a cluster of four arginines on the protein surface: two arginine residues (R124 and R125) on the β3-α5 loop, and two arginines (R192 and R196) on helix α7.

PA has been linked to proteolysis of viral and host proteins. Residues T157 and S624 are claimed to be reported as the protease active site. Our own in vitro protease assays described indicate that PA_N of SEQ ID NO: 7 has no detectable proteolytic activity. Further studies are therefore required to clarify the role of PA in protease activity and to determine the location of the active site. Nevertheless, several residues surrounding T157, including E154, K158, D160, E165, E166, R168 and R170, are highly conserved across influenza species, suggesting that this region is an important part of the polymerase complex.

Figure 4:
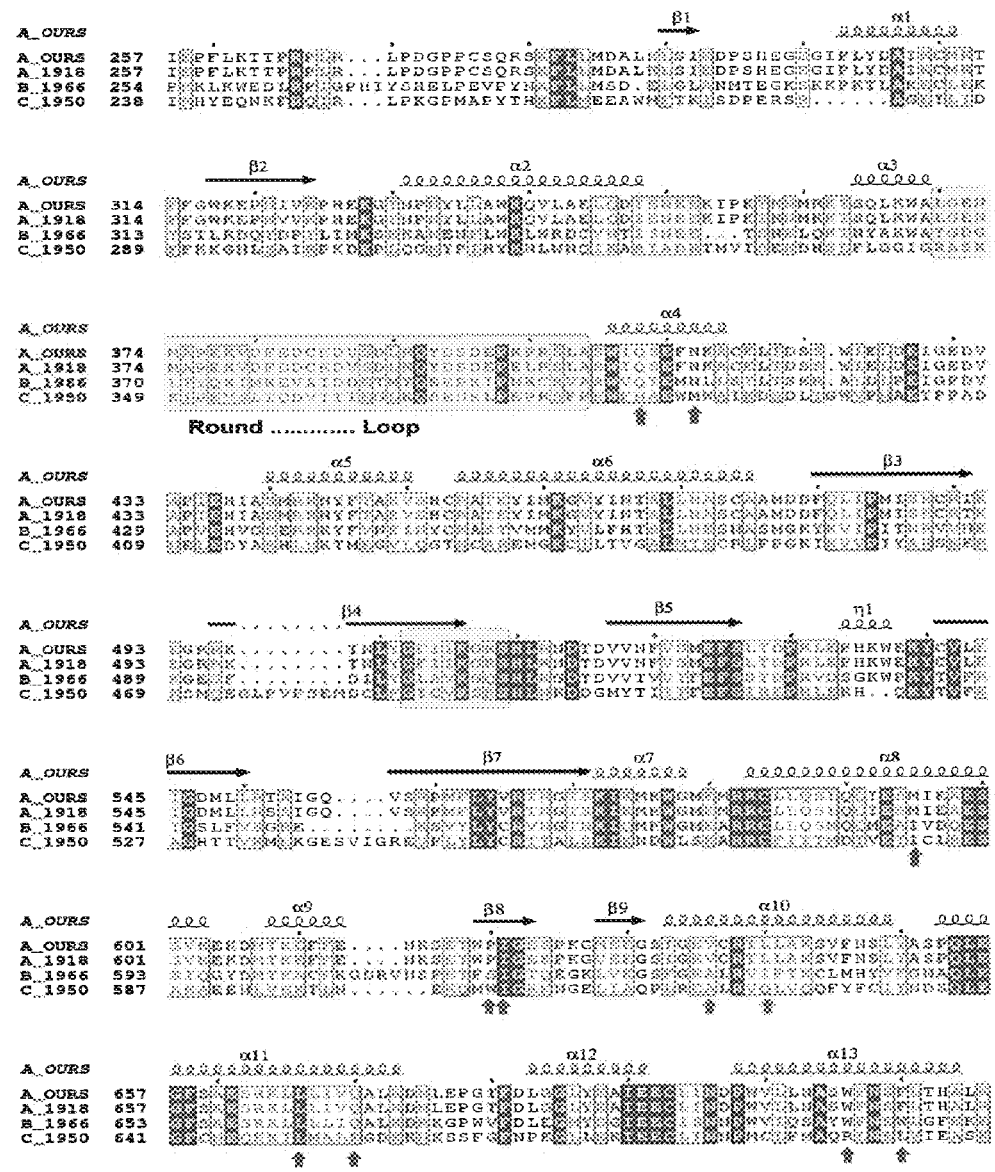
FIG. 4. C-terminal sequences of PA_N from three influenza viruses and the sequence of $PB1_N$ of SEQ ID NO: 2. A. Comparison of PA sequence from three different types of influenza virus. A_OURS is C-terminal sequences residues 257-717 of PA_N of SEQ ID NO: 1 from influenza virus type A strain A/goose/Guangdong/1/96, which according to the A_1996 in FIG. 1: A_1918: C-terminal sequence residues 257-717 of PA of SEQ ID NO: 8 from influenza virus type A strain, A/Brevig Mission/1/1918, which was a widely-circulating outbreak that caused the death of millions of people in Europe in 1918; B__1966: C-terminal sequences residues 253-713 of PA of SEQ ID NO: 3 from influenza virus type B strain B/Ann Arbor/1/1966; C__1950: C-terminal sequences residues 238-701 of PA of SEQ ID NO: 4 from influenza virus type C strain C/JJ/1950. Results showed highly conserved amino acid residues on C-terminal sequences of PA from influenza virus. B: Comparison of $PB1_N$ (SEQ ID NO: 2) sequence from four influenza viruses, A_OURS, A__1918, B__1966 and C__1950, as described above, "..." indicates the gene depletion in corresponding sites. In specification and claim, locus of specific amino acid was presented in the case A_OURS. Round loop in yellow frame is the big loop site in the structure. The other yellow frame (not labeled) is potential binding site for nucleic acids. Arrow indicates the amino acid residues in C-terminal of PA which bind to PB1 (SEQ ID NO: 2) peptide. In specification, locus of specific amino acid was presented in the case A_OURS (A__1996).

Notably, the region corresponding to α-helix and β sheet of influenza virus type A in influenza virus B or C was shown in FIG. 1 and FIGS. 4A & B. Sequence alignment for protein or peptide can be performed with CLUSTALW online program for sequence comparison.

In one embodiment, present invention discloses the expression and purification of PA_N of SEQ ID NO: 1 protein of influenza virus type A, including: (a), constructed the plasmid to express fusion or non-fusion peptides of influenza virus polymerase subunit PA. (residues 1~50 to 150-300 of SEQ ID NO:1). Transformed the following plasmids into prokaryotic or eukaryotic cells to express the tagged protein PAc; (b), recombinant proteins were then purified with an affinity column. After the tag was cleaved with protease, protein PA_N of SEQ ID NO: 7 was purified and its concentration was further determined.

In the three-dimensional structure of peptide PA_N of SEQ ID NO: 7 from influenza virus type A polymerase, at least 40% of atoms showed the same atomic coordinates, compared to that listed in Table. Or in a three-dimensional structure of influenza virus polymerase subunit PA_N of SEQ ID NO: 7, 40% of atomic coordinates on carbon skeleton of the amino acids of influenza virus polymerase subunit PA_N of SEQ ID NO: 7, showed less than or equal to 1.7 Å of average variance, compared to the atomic coordinates listed in Table 1.

In one embodiment, present invention discloses the methods to express and purify peptide PA_N of SEQ ID NO: 1 from influenza virus type A polymerase. A fusion protein was tagged with GST、Flag-tag、Myc-tag、MBP-tag or specific antibody; all plasmids contained selective gene, and optimal tag was GST. Recombinant proteins were then purified with an affinity column. After cleavage of tag with protease, proteins were purified by gel filtration chromatography or by ion exchange chromatography. Protein concentration was further determined by gel electrophoresis.

In one embodiment, present invention discloses the methods to express and purify peptide PA_N of SEQ ID NO: 1 from influenza virus type A polymerase. DNA fragment for PA_N of SEQ ID NO: 1 of influenza virus type A/goose/Guangdong/1/96 was cloned, and ligated to SalI-NotI restriction sites of expression vector pGEX-6p vector which contains the gene for resistance against ampicillin. Gene of avian H5N1 influenza A virus PA_N of SEQ ID NO: 1 was amplified with PCR, digested with BamHI and XhoI, ligated with BamHI-XhoI double digested vector, and transformed into E. coli stain BL21. Transformed BL21 was cultured, induced with 0.1-1 mM IPTG, and harvested with centrifuge.

In one embodiment, present invention discloses the methods to cocrystal peptide PA_N of SEQ ID NO: 7 from influenza virus type A polymerase, including: concentrated the purified peptide PA_N of SEQ ID NO: 7 to 5-30 mg/ml; screened the best conditions for crystal with hanging drop or sitting drop methods; obtained the crystal of peptide PA_N of SEQ ID NO: 7 of influenza virus type A polymerase.

In one embodiment, present invention discloses the methods to express the wild type or mutated peptide PA_N of SEQ ID NO: 1 which contained residues 1~50 to 200~300 of influenza virus type A polymerase (of SEQ ID NO:1), including: constructed the vector to express the fusion protein for the residues 1~50 to 200~300 of influenza virus type A polymerase (of SEQ ID NO:1); transformed the vectors and expressed fusion peptide PA_N of SEQ ID NO: 7. Peptide PA_N of SEQ ID NO: 7 had at least 40% same sequence as that in FIG. 1.

In one embodiment, present invention discloses the methods to express the wild type or mutated peptide PA_N of SEQ ID NO: 1. Inventors cloned the gene of PA_N of SEQ ID NO: 7 with PCR technique and other molecular techniques into various vectors, including series of pGEX from Amersham Pharmacia, pGEX-6p and pGEX-4T, series of pET from Novagen, and pMAL-c2 from Invitrogen, to express the GST-fusion protein GST-PA_N; vectors described above contained the gene for resistance against ampicillin, insertion sites used for ligation were BamHI and XhoI; DNA fragment for PA_N of SEQ ID NO: 7 was cloned from the genome of influenza virus type A/goose/Guangdong/1/96; DNA was double digested with BamHI and XhoI and ligated to BamHI-XhoI double digested expression vector, and transformed into E. coli BL21. Transformed E. coli BL21 was cultured, induced with IPTG (0.1~1 mM), centrifuged and harvested.

In one embodiment, present invention discloses the methods to screen candidate substances which can bind to peptide PA_N of SEQ ID NO: 7 with magnesium ion preferably, among the ions, magnesium, manganese, zinc, cuprum, cobalt or iron, including: (a), fixed PA_N of SEQ ID NO: 7 on the surface of carrier; (b), bound candidate substance to the PA_N of SEQ ID NO: 7 fixed carrier; (c), washed carrier with washing buffer to remove the unbound substance; (d), eluted and harvested candidate substance from the fixed carrier; (e), determined the concentration of free metal ions in the solution; (f), calculated the binding capacity of candidate substance to PA_N of SEQ ID NO: 7, based on the concentration of free metal ions in the solution.

In one embodiment, peptide PA_N of SEQ ID NO: 7 was covalently crosslinked or bound with affinity mediator on the surface of fixed carrier in above procedure (a). And affinity mediator on the surface of fixed carrier described here contained the binding groups.

In one embodiment, affinity mediator used was GST, Flag-tag, Myc-tag, MBP-tag, His-tag, specific antibody or other peptides, and the mediator on the surface of carrier was a corresponded binding groups.

In one embodiment, present invention discloses the methods to screen the candidate substances which can bind to the peptide PA_N of SEQ ID NO: 7 with magnesium ion preferably, among the ions, magnesium, manganese, zinc, cuprum, cobalt or iron. The candidate substances were protein labeled with an isotope or other molecules, preferably, including green fluorescent protein, various fusion peptides such as peroxidase, phosphohydrolase, protein kinase, transferase, et al.

In one embodiment, present invention discloses the methods to screen candidate substances which can bind to peptide PA_N of SEQ ID NO: 7 with one of the following ions: magnesium, manganese, zinc, cuprum, cobalt or iron, preferably magnesium. Then the affinity chromatography column was used on the surface of a fixed carrier.

Crystallization of Protein and Optimization:

For initial crystallization experiments, purified peptide PA_N of SEQ ID NO: 7 was concentrated at 5-30 mg/ml, and 1+1 µl hanging drops (protein: reservoir) were set up against a standard set of sparse-matrix crystallization experiments utilizing commercial screens (Hampton Research). Several hits were observed with hanging drop method, and obtained the primary crystal using various crystallization reagents.

A well-ordered crystal was obtained in SEQ ID NO: 7 in crystallization solution containing 25% PEG8000 or selenomethionine crystallization solutions containing 20%. PEG3350, in different pH 4-9 conditions, under further optimized conditions. Larger parental crystals were obtained at 2.2- Å resolution and selenomethionine-labeled crystals at ~3.0 Å resolutions in 100 mM MES pH. 6.5 crystallization solutions 20% PEG8000 or 20% PEG3350, 100 mM $MgCl_2$ or 100 mM $MgAc_2$ within one week. Collect all the X-ray diffraction data.

Data Collection and Crystal Structural Analysis:

First, using FR-E X-ray diffraction (from Rigaku) at 1.5418 Å wavelength collected the parent data of N-terminal peptide PA_N of SEQ ID NO: 7 with 2.9 Å resolution. Then collected selenium derivative crystal data with a 3.3 Å peak and edge using a synchrotron radiation meter (Line Station Number: SBC 19ID; detection screen: ADSC Q315) at APS in Chicago at 0.9783 and 0.9785 Å wavelength. Analyzed the three sets of data from HKL2000 (Otwinowski 1997) and found the parental crystal had P1 space group, and cell parameters: a=51.1 Å, b=151.0 Å, c=59.8 Å. $\alpha$=96.6°, $\beta$=96.8°, $\gamma$=109.5°. The selenomethionine labeled crystal had P6(4)22 space group, and cell parameters: $\alpha$=b=73.8 Å, c=123.4 Å, $\alpha$=$\beta$=90°, $\gamma$=120°. Phase was calculated using multi-wavelength anomalous scattering (Hendrickson 1991), and file sca was analyzed by using SHELXD (Sheldrick 1998), to find selenium atoms. Six selenium atoms were found and coordinated. Analyzed the coordinate and two sets of data Peak and Edge were analyzed and phase was calculated, using MLPHARE program. Then the electron density map was modified using DM program. Several secondary structures (including α-helix and β-sheet) were clearly observed on the calculated electron density map. Thus about 80 residues were modeled, and then the initial model was set up after the model repeated and modified with CNS software package. Based on the initial model from high-resolution parental data, molecule replacement was performed using Phaser program, a clear explanation for parental data was obtained. Structural models were further simulated and modified alternately using CNS program. It was shown that the R factor was 23.1%, the R-free factor was 25.2%. Three water molecules on the magnesium ion were integrated into this model. The R factor was 23.1% and the R-free factor was 25.2% in the corrected structure.

Atom coordinate of three-dimensional crystal structure of PA_N of SEQ ID NO: 7 peptide was shown in Table 1.

EXAMPLES

Example 1

Method for Expression of PA-N Peptide of Avian Influenza A Virus of SEQ ID NO: 7

In one embodiment, present inventor expressed protein PA with two peptides; one contained residues 1-256 of SEQ ID NO: 1 and the other contained residues 257-716 of SEQ ID NO: 1. Cloned nucleic acid fragment encoding these two fragments into expression vectors, the proteins are expressed and purified from *E. coli*. Purified the N-terminal region comprising residues 1-256 of SEQ ID NO:1 of and subjected to crystallization. The *E. coli* expressing the C-terminal region of PA is expressed, and the Protein is harvested and subjected to co-purification with N-terminal region of PB1 of SEQ ID NO: 2.

Residues 1-25 or 2-48 of PB1 of N-terminal of SEQ ID NO:2 were expressed in *E. coli* as GST fusion peptide. A fragment which contained at least 50% of residues 257-716 of avian influenza A virus PA_N of SEQ ID NO: 1 was expressed in *E. coli* or other eukaryotic cells.

Expression of PA-N of SEQ ID NO: 7 in *E. coli* and Purification

Nucleic acid encoding residues 1-256 of the avian influenza A virus PA of SEQ ID NO: 1 was cloned into BamHI-XhoI double digested pGEX-6p vector (Amersham Pharmacia Inc.) and over-expressed in *E. coli* strain BL21 containing gene encoding for resistance against ampicillin as glutathione S-transferase (GST) fusion protein. The recombinant protein was purified with a glutathione affinity column. GST was cleaved with and further separated with PRESCISSION PROTEASE PROTEASE (Amersham Biosciences) into GST and PA-N of SEQ ID NO: 7. A vector expressing the fusion protein was transformed into *E. coli* strain BL21. BL21 was cultured in LB medium overnight at 37 degree. After 12 hr incubation, BL12 was diluted 1/100 to large-scale culture medium, and cultured to OD~1.0. BL12 was induced with 0.1-1 mM IPTG for 3-6 hr and harvested by centrifuge. The cell pellet was stored at −20 degree or −80 degree for further use or directly used for the purification.

Expression and Purification of Complex of PA_N and PB1

Gene for residues 257-716 of the avian influenza A virus PA_N of SEQ ID NO: 1 was cloned into BamHI-XhoI double digested pGEX-6p vector (Amersham Pharmacia Inc.) and over-expressed in *E. coli* strain BL21 which contained a gene for resistance against ampicillin. Recombinant protein was purified with a glutathione affinity column. Glutathione S-transferase (GST) was cleaved and further separated with PRESCISSION PROTEASE (Amersham Biosciences) into GST peptide and PA_N of SEQ ID NO: 1 peptide. The vector expressing fusion protein was transformed into *E. coli* strain BL21. BL21 was cultured in LB medium overnight at 37° C. After 12 hr incubation, BL12 was diluted 1/100 to large-scale culture medium, and cultured to OD~1.0. BL12 was induced with 0.1-1 mM IPTG for 3-6 hr and harvested by centrifuge. The cell pellet was stored at −20° C. or −80° C. for further use or directly used for the purification.

Present inventors have expressed the peptides of residues 1-48 and 1-25 of avian influenza A virus PB of SEQ ID NO:2 previously. Here, gene for residues 1-48 of avian influenza A virus PB of SEQ ID NO:2 were cloned into BamHI-XhoI double digested pGEX-6p vector (Amersham Pharmacia Inc.), and over expressed in *E. coli* strain BL21 which contained a gene for resistance against ampicillin. Recombinant protein was purified with a glutathione affinity column. Glutathione S-transferase (GST) was cleaved with PRESCISSION PROTEASE (Amersham Biosciences) and further separated into GST peptide and PA_N of SEQ ID NO: 1 peptide. The vector expressing fusion protein was transformed into *E. coli* strain BL21. BL21 was cultured in LB medium, induced with 0.1-1 mM IPTG foe 3-6 hr. The cell was harvested by centrifuge, and the pellet was directly used for the purification or stored at −20° C. or −80° C. for further use.

The inventors resuspended the GST-PA_N expressing *E. coli* with 20 mM Tris-HCl (pH8.0)/250 mM NaCl buffer or 1×PBS (pH7.4) buffer, and lysed the cells by sonicator. Precipitate was discarded. Supernatant was harvested. GST-PA_N was purified with glutathione affinity column, then cleaved with PRESCISSION PROTEASE (Amersham Pharmacia Inc) and separated into GST peptide and PA_N of SEQ ID NO: 1 peptide. The protein was purified by ion exchange and gel filtration chromatography, and further concentrated to 5-30 mg/mL for crystallization.

The inventors resuspended GST-PAC expressing *E. coli* and GST-PB1N expressing *E. coli* with 20 mM Tris-HCl (pH8.0)/250 mM NaCl buffer or 1×PBS (pH7.4) buffer, respectively. The two suspensions of GST-PAC and GST-PB1 (SEQ ID NO: 2) were mixed with the mole ratio at 0.1:1~1:0.1, at 0.5:1~1:0.5, preferably at 1:1.

After lysing by sonicator or other methods, the mixed suspension was centrifuged at 20,000×g. The supernatant was harvested and subjected to Glutathione-Sepharose affinity column to which GST fusion protein can bind. The affinity column was completely washed with washing buffer described above, and the GST fusion protein was cleaved with PRESCISSION PROTEASE (Amersham Biosciences). It took 24 hours to completely cleave GST fusion protein. PAC/PB1N peptide complex was further purified with Q ion exchange (Amersham Pharmacia Inc.) and Superdex-200 gel filtration chromatography (Amersham Pharmacia Inc.). Protein concentration was determined with SDS-PAGE. Final purity was more than 90%. Purified protein was concentrated with Amicon Ultra centrifugal filtration devices (Millipore) to 5-30 mg/mL for further crystallization.

It is well known for the person who is working in the same area that, PA_N and PA$_C$ of SEQ ID NO: 1 and PB1$_N$ of SEQ ID NO: 2 not only can be expressed in *E. coli*, but and also in other eukaryotic cells, e.g. insect cells; other restriction enzymes, digestion sites and ligases can be used in the above clone procedure; also, these protein can be expressed with GST and other fusion markers, and purified with corresponding protocols. Finally, these fusion markers can be cleaved as described above. All alterations and modifications based on present invention as described above are under protection.

Notably, the region in influenza virus B or C, which corresponding to α-helix and β sheet of influenza virus type A, was shown in FIG. 1.

Example 2

Crystallization of PA-N of SEQ ID NO: 7

The protein of SEQ ID NO: 7 was concentrated to 5-30 mg/mL. The best conditions for crystallizing were screened using 1:1 μL hanging drops (protein:reservoir) set up against a standard set of sparse-matrix crystallization experiments utilizing commercial screens (Hampton Research). Several hits were observed with hanging drop method, and obtained the primary crystal using various crystallization reagents.

The protein SEQ ID NO: 7 was crystallized in the space group P1. A well-ordered crystal is obtained using 25% PEG8000 at pH 4-9 in different buffers. A selenomethionyt derivative of SEQ ID NO:7 is crystallized using 100 mM MES 20% PEG3350, 100 mM $MgCl_2$ or 100 mM MgAc2 in space group $P6_422$ at pH 6.5. The structure was phased to 3 Å by multiple-wavelength anomalous dispersion from a selenomethionyl derivative, and traced using 2.2 Å native data.

Notably, the region of influenza virus B or C, with corresponding α-helix and β-sheet of influenza virus type A, was shown in FIG. 1.

Example 3

Three-Dimensional Structure of PA-N of SEQ ID NO:7

First, using FR-E X-ray diffraction (from Rigaku) at 1.5418 Å wavelength, the parent data of N-terminal peptide PA_N of SEQ ID NO: 7 was collected with 2.9 Å resolution. Then collected selenium derivative crystal data with a 3.3 Å peak and edge using synchrotron radiation meter (Line Station Number: SBC 19ID; detection screen: ADSC Q315) at APS in Chicago at 0.9783 and 0.9785 Å wavelength. The three sets of data were analyzed from HKL2000 (Otwinowski 1997) and found the parental crystal had P1 space group, and cell parameters: a=51.1 Å, b=151.0 Å, c=59.8 Å, α=96.6°, β=96.8°, γ=109.5°. Selenomethionine labeled crystal had P6(4)22 space group, and cell parameters: α=b=73.8 Å, c=123.4 Å, α=β=90°, γ=120°. Phase was calculated using multi-wavelength anomalous scattering (Hendrickson 1991), and file sca was analyzed by using SHELXD (Sheldrick 1998), to find selenium atoms. Six selenium atoms were found and coordinated. Analyzed the coordinate and two sets of data Peak and Edge were analyzed and phase was calculated, using MLPHARE program. Then the electron density map was modified using a DM program. Several secondary structures (including α-helix and β-sheet) were clearly observed on the calculated electron density map. Thus, about 80 residues were modeled, then the initial model was set up after model repeated and modified with CNS software package. Based on the initial model from high-resolution parental data, molecule replacement was performed using Phaser program, then a clear explanation for parental data was obtained. Structural models were further simulated and modified alternately using CNS program. It was shown that the R factor was 23.1% and the R-free factor was 25.2%, Three water molecules on the magnesium ion were integrated into this model. The R factor was 23.1% and the R-free factor was 25.2% in the corrected structure.

Finally, it was calculated that the parental crystal had a P1 space group, and cell parameters: a=51.1 Å, b=151.0 Å, c=59.8 Å, α=96.6°, β=96.8°, γ=109.5°. The selenomethionine labeled crystal had a P6(4)22 space group, and cell parameters: α=b=73.8 Å, c=123.4 Å, α=β=90°, γ=120°.

Example 4

Crystallization of PA_N Peptide

Inventors concentrated the protein described above to 5-30 mg/mL. The best conditions for crystal were screened using 1+1 μl hanging drop method (protein:reservoir) with crystal reagents set up against a standard set of sparse-matrix crystallization experiments utilizing commercial screens (Screen Kit I/II and Index from Hampton Research and other companies.) Several hits were observed with hanging drop method, and obtained the primary crystal using several crystallization reagents.

Preferably, the protein was further crystallized using 25% PEG8000 at pH 4-9 in different buffers. A selenomethionyl derivative was crystallized using 20% PEG8000 or 20% PEG3350, 100 mM $MgCl_2$ or 100 mM $MgAc_2$. The structure was phased to 3 Å by multiple-wavelength anomalous dispersion from a selenomethionyl derivative, and traced using 2.2 Å native data.

Example 5

The Method to Screen PA_N of SEQ ID NO: 7 Binding Small Molecules

In the process of screening the small molecules for anti-influenza viral drugs, fusion genes formed from the PA_N of SEQ ID NO: 7 gene and the GFP gene were used as the indicators for the depolymerization of the protein complex by the small molecules. The PA_N of SEQ ID NO: 7 gene was ligated with the GFP gene to express the GFP-fusion protein.

Method 1: the method for expression and purification of PA_N SEQ ID NO: 7. GST-fusion protein (GST-PA_N) was expressed. Subjected and bound GST-PA_N of SEQ ID NO: 7 protein to Glutathione affinity column. This column was stained green after binding with GST-PA_N due to GFP protein which ligated with PA_N of SEQ ID NO: 7. The column was washed with washing buffer to remove unbound protein. Next, the mixture containing small molecular compounds for screening was loaded into the column (notably, the mixture didn't contain Glutathione or other compounds to elute the GST from column). Gradually, the small molecular compounds were separated and purified using GFP protein as an indicator. The compounds binding to PA_N of SEQ ID NO: 7 peptide were tracked and determined on the affinity column. Beside the above method, which used GST as the affinity medium, Flag-tag, Myc-tag, MBP (Maltose binding protein)-tag, and other specific antibodies can be used as affinity mediators too. Corresponding mediators can be fixed on the affinity column, i.e., anti-Flag-tag antibody (Sigma) was fixed on the column when Flag-tag was chosen as the medium. Compounds binding to PA_N of SEQ ID NO: 7 can be determined by mass spectrum and others.

Method 2: PA_N of SEQ ID NO: 7 was purified and bound covalently to a gel medium using a chemical crosslink method, and kept the protein from denaturing. The isotope-labeled small molecular compounds or peptides were loaded to the gel medium and bound to PA_N of SEQ ID NO: 7 protein. If any small molecular compounds or peptides were bound to PA_N of SEQ ID NO: 7 protein, concentration of elution would be decreased. The gel medium was washed to remove other unbound compounds or peptides. PA _N of SEQ ID NO: 7 was denatured using urea, and eluted the bound small molecular compounds or peptides from column. Using mass spectrum and other methods analyzed these small molecular compounds or peptides and further obtained their structural information. This small molecular compound was the potential drug to deactivate PA_N of SEQ ID NO: 7.

Example 6

Application of Three-Dimensiona Structure of PA_N of SEQ ID NO: 7 on the Designing and Screening of Peptides, Proteins, Inorganic or Organic Compounds to Develop Anti-Influenza Viral Drugs.

Application of three-dimensional structure of PA_N of SEQ ID NO: 7 on the designing and screening of peptides, proteins, inorganic or organic compounds to develop anti-influenza viral drugs, as described in the following: based on the three-dimensional structure of PA_N of SEQ ID NO: 7, using computer simulation, to design the peptides or compounds which can bind to specific site of influenza virus type A RNA polymerase; based on the three-dimensional structure of PA_N of SEQ ID NO: 7, using computer simulation, screen the peptides or compounds which can bind to a specific site of influenza virus type A RNA polymerase; based on the three-dimensional structure of PA_N of SEQ ID NO: 7, design or screen peptides or compounds which can bind to any subtype of influenza virus RNA polymerase which contain a more than 50% similar sequence as the influenza virus type A RNA polymerase described above, and analyze the binding capacity; based on the three-dimensional structure of PA_N of SEQ ID NO: 7, design or screen, and crystallize the peptides or compounds, which can bind to any subtype of influenza virus RNA polymerase which contain a more than 50% similar sequence as PA_N of SEQ ID NO: 7 from influenza virus type A RNA polymerase, and analyze the integration of these peptides or compounds with RNA polymerase through analyzing the three-dimensional structure obtained by the crystal diffraction method.

Example 7

Based on the Three-Dimensional Structure of PA_N of SEQ ID NO: 7 from Influenza Virus Type A RNA Polymerase, Design and Screen the Peptides for Anti-Influenza Viral Drug.

The potential anti-influenza peptide drugs which contain at least 3 same residues as the PA_N of SEQ ID NO: 7 described above.

Any protein or region the three-dimensional structure of three subunits PA, PB1 and PB2, or the complex of PA, PB1 and PB2 from any subtype of influenza virus RNA polymerases, contains at least 40% of the same sequence as the PA_N of SEQ ID NO: 7 from influenza virus type A RNA polymerase we described above.

Any protein or region in the three-dimensional structure of three subunits PA, PB1 and PB2, or the complex of PA, PB1 and PB2 from any subtype of the influenza virus RNA polymerases, showed less than or equal to 1.7 Å of average variance, compared to at least 40% of the same sequence as the PA_N of SEQ ID NO: 7 from influenza virus type A RNA polymerase as described above.

Any protein in the three-dimensional structure of three subunits PA, PB1 and PB2, or the complex of PA, PB1 and PB2 from any subtype of influenza virus RNA polymerases, contains at least 40% of the same sequence as region 2-12 of $PB1_N$ of SEQ ID NO: 2 from influenza virus type A RNA polymerase as described above.

Any peptide or small molecules having interaction with the key amino acids on subunits PA of influenza virus RNA polymerases described above.

The application of the three-dimensional structure of PA_N of SEQ ID NO: 7 described above on the drug screen and design.

A method to screen the substances or peptides based on the three-dimensional structure of PA_N of SEQ ID NO: 7, including: acquiring the crystal containing PA_N of SEQ ID NO: 7 peptide and parental crystal having a P1 space group, and cell parameters: a=51.1 Å, b=151.0 Å, c=59.8 Å, α=96.6°, β=96.8°, γ=109.5°. And a selenomethionine labeled crystal having a P6(4)22 space group, and cell parameters: α=b=73.8 Å, c=123.4 Å, α=β=90°, γ=120°. Acquiring a three dimensional protein structure of the crystal containing PA_N of SEQ ID NO: 7 peptide by X-ray crystallography, and including structures containing at least 40% of atomic coordinates on carbon skeleton with less than or equal to 1.7 Å of average variance, compared to the amino acids of influenza virus polymerase subunit PA_N of SEQ ID NO: 7.

A method to express influenza virus polymerase subunit. PA_N of SEQ ID NO: 1: express PA in *E. coli* or eukaryotic cells. Express and purify the protein which contains at least 40% of the same sequence as PA_N of SEQ ID NO: 7.

In one optimal embodiment, application of PA_N of SEQ ID NO: 7 can be used on the designing and screening of peptides, proteins, compounds and drugs for anti-influenza virus.

In one optimal embodiment, peptides used for the treatment of infections caused by influenza virus, including those which have an interaction with peptide PA_N of SEQ ID NO: 7, at least one α-helix or β-sheet, at least one residue as described above.

In one optimal embodiment, proteins used for the treatment of infections caused by influenza virus, including those which have an interaction with peptide PA_N of SEQ ID NO: 7, at least one α-helix or β-sheet, at least one residue as described above.

In one optimal embodiment, compounds used for the treatment of infections caused by influenza virus, including those which have an interaction with peptide PA_N of SEQ ID NO: 7, at least one α-helix or β-sheet, at least one residue as described above.

In one optimal embodiment, a combination of drugs included peptides, proteins or compounds as described above.

A combination of drugs in the present invention including a carrier or excipient, which are preferably hydrophilic, and antibodies and/or immune conjugates that can be dissolved in buffer, saline, and others. These solutions were sterilized with regular techniques and contained no other substances. These components included some supplemental substances which are pharmaceutically suitable and close to physiological conditions, such as buffers for adjusting pH, and reagents for adjusting toxicity, for example, sodium acetate, sodium chloride, potassium chloride, calcium chloride, sodium lactate and so on. Because the concentration of the fusion protein had a varied range, components described above can be chosen based on the selected mode and required volume, viscosity, weight, etc, of the specific patient.

Therefore, a typical embodiment in the present invention was to deliver daily 1.2-1200 μg of pharmaceutical immunotoxin components to the brain. Another typical embodiment was to inject about 0.1-10 mg of pharmaceutical immunotoxin components to patients with breast, ovarian or lung cancer, i.v. 0.1-100 mg per person daily can be used, when drug was applied to a secluded location, and not into the blood or lymphatic system, such facilities into a coelome or lacuna. The methods to prepare components were well known and mastered by professionals, and are described in the publications, i.e. Remington's Pharmaceutical Science, 19th ed., Mack Publishing Company, Easton, Pa. (1995).

Components in the present invention can be used for therapeutic treatments. In one application for treatments, component was applied into the patients (with glioblastoma, breast cancer, ovarian cancer or lung cancer), the dose should be sufficient to provide relief or partial control of the disease and its complications, which is called "effective dose". Application of effective dose depends on the severity of the disease and the patient's general health. The effective dose of components gives some relief which can be confirmed with subjective symptoms, or some improvement which can be recorded by physicians or other qualified observer.

Giving single or multiple doses depends on the need, dose, frequency, and tolerance of the patients. Regardless, a sufficient amount of the immunotoxin should be provided to treat patients effectively. Preferably, immunotoxin can be given once, or periodically, until particular treatment effect was obtained or continuous treatment was stopped by adverse reaction. Typically, these doses are sufficient to treat or improve symptoms of the disease without non-tolerant toxicity.

Immune conjugates in present invention can be prepared as immune parenteral sustained release formulation (such as implants, oil injection, or microparticle system) (for details of protein delivery system, see Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995)). Particulate systems include microspheres, particles, microcapsules, nano-micro-capsules, nano-microspheres, and nanoparticles. Therapeutic protein is the core in the microcapsules. In a small sphere, the therapeutic substance is dispersed in the particles. Particles microspheres, and microcapsules, less than about 1 µm, are usually referred to as nano-particles, nano-sphere, micro-and nano-capsules. The only way to deliver nanoparticles to a capillary which has about 5 µm diameter is intravenous. The diameter of microparticles is about 100 µm, and microparticles can be delivered by subcutaneous or intramuscular injection. For examples, Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339, (1992). Both were cited in present invention.

Polymer in composition of immune conjugates can be used for controlled release of ions in present invention. It is well known that various degradable or non-degradable polymers are used to control the drug release (Langer, R., *Accounts Chem. Res.* 26:537-542 (1993)). For example, retarding polymer polaxamer 407 is viscous and ambulatory at low temperatures, but forms semi-solid gel at body temperature. It was proved that polaxamer 407 is an effective carrier for formation of recombinant interleukin-2 and urease and sustained delivery (Johnston, etc., Pharm. Res. 9:425-434 (1992), Pee, etc. J. Parent. Sci. Tech. 44 (2):58-65 (1990)). Similarly, hydroxyapatite has also been used as a protein controlled release microcarrier (Ijntema etc., Int. J. Pharm. 112:215-224 (1994)). On the other hand, liposomes are used for lipid-coated controlled release and targeted drug delivery (Betageri, et.al, LIPOSOME DRUG DELIVERY SYSTEMS, Technomic Publishing Co., Inc., Lancaster, Pa. (1993)). Many other therapeutic proteins controlled release system has been well understood. See more examples, U.S. Pat. No. 5,055,303, 5,188,837, 4,235,871, 4,501,728, 4,837,028, 4,957,735 and 5,019,369, 5,055,303; 5,514,670; 5,413,797; 5,268,164; 5,004,697; 4,902,505; 5,506,206, 5,271,961; 5,254,342 and 5,534,496, and all of these are referenced in present invention.

Results

TABLE 1

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| | | | | | | | | | | |
|---|---|---|---|---|---|---|---|---|---|---|
| atom | 1 | CB | LEU | A | −2 | 3.950 | 4.473 | −17.980 | 1.00 | 42.68 A |
| atom | 2 | CG | LEU | A | −2 | 3.113 | 3.369 | −17.352 | 1.00 | 46.79 A |
| atom | 3 | CD1 | LEU | A | −2 | 1.703 | 3.867 | −17.027 | 1.00 | 39.32 A |
| atom | 4 | CD2 | LEU | A | −2 | 3.090 | 2.207 | −18.307 | 1.00 | 45.13 A |
| atom | 5 | C | LEU | A | −2 | 5.682 | 5.991 | −17.097 | 1.00 | 41.97 A |
| atom | 6 | O | LEU | A | −2 | 5.934 | 6.563 | −18.159 | 1.00 | 42.15 A |
| atom | 7 | N | LEU | A | −2 | 3.258 | 6.395 | −16.620 | 1.00 | 47.49 A |
| atom | 8 | CA | LEU | A | −2 | 4.330 | 5.390 | −16.837 | 1.00 | 44.02 A |
| atom | 9 | N | GLY | A | −1 | 6.533 | 5.854 | −16.087 | 1.00 | 42.00 A |
| atom | 10 | CA | GLY | A | −1 | 7.882 | 6.349 | −16.164 | 1.00 | 40.64 A |
| atom | 11 | C | GLY | A | −1 | 8.680 | 5.318 | −16.925 | 1.00 | 41.01 A |
| atom | 12 | O | GLY | A | −1 | 8.114 | 4.427 | −17.544 | 1.00 | 44.33 A |
| atom | 13 | N | SER | A | 0 | 9.995 | 5.453 | −16.912 | 1.00 | 40.13 A |
| atom | 14 | CA | SER | A | 0 | 10.881 | 4.524 | −17.610 | 1.00 | 41.09 A |
| atom | 15 | CB | SER | A | 0 | 11.918 | 5.355 | −18.360 | 1.00 | 41.31 A |
| atom | 16 | OG | SER | A | 0 | 12.929 | 4.549 | −18.922 | 1.00 | 47.46 A |
| atom | 17 | C | SER | A | 0 | 11.556 | 3.640 | −16.550 | 1.00 | 39.90 A |
| atom | 18 | O | SER | A | 0 | 12.102 | 4.178 | −15.578 | 1.00 | 40.03 A |
| atom | 19 | N | MET | A | 1 | 11.538 | 2.309 | −16.680 | 1.00 | 37.39 A |
| atom | 20 | CA | MET | A | 1 | 12.180 | 1.527 | −15.616 | 1.00 | 35.12 A |
| atom | 21 | CB | MET | A | 1 | 11.891 | 0.025 | −15.681 | 1.00 | 32.68 A |
| atom | 22 | CG | MET | A | 1 | 12.678 | −0.726 | −14.573 | 1.00 | 31.16 A |
| atom | 23 | SD | MET | A | 1 | 11.985 | −0.567 | −12.881 | 1.00 | 35.48 A |
| atom | 24 | CE | MET | A | 1 | 10.653 | −1.712 | −13.127 | 1.00 | 35.22 A |
| atom | 25 | C | MET | A | 1 | 13.673 | 1.674 | −15.590 | 1.00 | 35.84 A |
| atom | 26 | O | MET | A | 1 | 14.281 | 1.637 | −14.534 | 1.00 | 36.20 A |
| atom | 27 | N | GLU | A | 2 | 14.257 | 1.813 | −16.766 | 1.00 | 37.08 A |
| atom | 28 | CA | GLU | A | 2 | 15.694 | 1.949 | −16.905 | 1.00 | 42.95 A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| atom | 29 | CB | GLU | A | 2 | 16.001 | 1.955 | −18.391 | 1.00 | 43.58 | A |
|---|---|---|---|---|---|---|---|---|---|---|---|
| atom | 30 | CG | GLU | A | 2 | 17.253 | 1.267 | −18.786 | 1.00 | 49.09 | A |
| atom | 31 | CD | GLU | A | 2 | 18.072 | 2.155 | −19.661 | 1.00 | 50.99 | A |
| atom | 32 | OE1 | GLU | A | 2 | 17.572 | 2.546 | −20.732 | 1.00 | 48.73 | A |
| atom | 33 | OE2 | GLU | A | 2 | 19.203 | 2.480 | −19.259 | 1.00 | 57.22 | A |
| atom | 34 | C | GLU | A | 2 | 16.188 | 3.232 | −16.187 | 1.00 | 43.64 | A |
| atom | 35 | O | GLU | A | 2 | 17.312 | 3.281 | −15.669 | 1.00 | 42.26 | A |
| atom | 36 | N | ASP | A | 3 | 15.314 | 4.248 | −16.155 | 1.00 | 45.03 | A |
| atom | 37 | CA | ASP | A | 3 | 15.544 | 5.547 | −15.492 | 1.00 | 46.05 | A |
| atom | 38 | CB | ASP | A | 3 | 14.448 | 6.586 | −15.810 | 1.00 | 49.57 | A |
| atom | 39 | CG | ASP | A | 3 | 14.576 | 7.257 | −17.168 | 1.00 | 50.47 | A |
| atom | 40 | OD1 | ASP | A | 3 | 13.734 | 8.159 | −17.411 | 1.00 | 55.29 | A |
| atom | 41 | OD2 | ASP | A | 3 | 15.453 | 6.908 | −17.979 | 1.00 | 49.01 | A |
| atom | 42 | C | ASP | A | 3 | 15.412 | 5.330 | −13.993 | 1.00 | 46.74 | A |
| atom | 43 | O | ASP | A | 3 | 16.231 | 5.797 | −13.199 | 1.00 | 50.29 | A |
| atom | 44 | N | PHE | A | 4 | 14.332 | 4.653 | −13.615 | 1.00 | 44.42 | A |
| atom | 45 | CA | PHE | A | 4 | 14.072 | 4.403 | −12.207 | 1.00 | 42.70 | A |
| atom | 46 | CB | PHE | A | 4 | 12.787 | 3.579 | −12.050 | 1.00 | 39.48 | A |
| atom | 47 | CG | PHE | A | 4 | 12.687 | 2.841 | −10.751 | 1.00 | 37.51 | A |
| atom | 48 | CD1 | PHE | A | 4 | 12.130 | 3.437 | −9.611 | 1.00 | 36.82 | A |
| atom | 49 | CD2 | PHE | A | 4 | 13.188 | 1.546 | −10.654 | 1.00 | 31.62 | A |
| atom | 50 | CE1 | PHE | A | 4 | 12.084 | 2.734 | −8.389 | 1.00 | 35.90 | A |
| atom | 51 | CE2 | PHE | A | 4 | 13.145 | 0.848 | −9.450 | 1.00 | 30.43 | A |
| atom | 52 | CZ | PHE | A | 4 | 12.597 | 1.438 | −8.318 | 1.00 | 30.97 | A |
| atom | 53 | C | PHE | A | 4 | 15.263 | 3.672 | −11.617 | 1.00 | 42.90 | A |
| atom | 54 | O | PHE | A | 4 | 15.826 | 4.091 | −10.626 | 1.00 | 43.95 | A |
| atom | 55 | N | VAL | A | 5 | 15.659 | 2.582 | −12.246 | 1.00 | 44.15 | A |
| atom | 56 | CA | VAL | A | 5 | 16.788 | 1.826 | −11.746 | 1.00 | 42.86 | A |
| atom | 57 | CB | VAL | A | 5 | 17.055 | 0.638 | −12.676 | 1.00 | 40.10 | A |
| atom | 58 | CG1 | VAL | A | 5 | 18.535 | 0.306 | −12.684 | 1.00 | 39.97 | A |
| atom | 59 | CG2 | VAL | A | 5 | 16.221 | −0.545 | −12.194 | 1.00 | 37.11 | A |
| atom | 60 | C | VAL | A | 5 | 18.078 | 2.650 | −11.537 | 1.00 | 42.69 | A |
| atom | 61 | O | VAL | A | 5 | 18.836 | 2.409 | −10.612 | 1.00 | 40.16 | A |
| atom | 62 | N | ARG | A | 6 | 18.335 | 3.634 | −12.381 | 1.00 | 45.00 | A |
| atom | 63 | CA | ARG | A | 6 | 19.575 | 4.400 | −12.229 | 1.00 | 46.37 | A |
| atom | 64 | CB | ARG | A | 6 | 20.003 | 4.967 | −13.581 | 1.00 | 42.81 | A |
| atom | 65 | CG | ARG | A | 6 | 20.450 | 3.885 | −14.536 | 1.00 | 38.09 | A |
| atom | 66 | CD | ARG | A | 6 | 20.756 | 4.430 | −15.932 | 1.00 | 40.42 | A |
| atom | 67 | NE | ARG | A | 6 | 20.923 | 3.360 | −16.918 | 1.00 | 40.98 | A |
| atom | 68 | CZ | ARG | A | 6 | 21.986 | 2.560 | −17.003 | 1.00 | 42.59 | A |
| atom | 69 | NH1 | ARG | A | 6 | 23.006 | 2.697 | −16.163 | 1.00 | 42.00 | A |
| atom | 70 | NH2 | ARG | A | 6 | 22.019 | 1.600 | −17.922 | 1.00 | 44.47 | A |
| atom | 71 | C | ARG | A | 6 | 19.634 | 5.503 | −11.187 | 1.00 | 46.76 | A |
| atom | 72 | O | ARG | A | 6 | 20.714 | 5.834 | −10.692 | 1.00 | 49.73 | A |
| atom | 73 | N | GLN | A | 7 | 18.486 | 6.079 | −10.868 | 1.00 | 48.18 | A |
| atom | 74 | CA | GLN | A | 7 | 18.434 | 7.140 | −9.884 | 1.00 | 51.56 | A |
| atom | 75 | CB | GLN | A | 7 | 17.509 | 8.289 | −10.403 | 1.00 | 53.67 | A |
| atom | 76 | CG | GLN | A | 7 | 16.327 | 7.877 | −11.373 | 1.00 | 61.44 | A |
| atom | 77 | CD | GLN | A | 7 | 16.282 | 8.626 | −12.753 | 1.00 | 64.49 | A |
| atom | 78 | OE1 | GLN | A | 7 | 15.438 | 9.510 | −12.985 | 1.00 | 62.59 | A |
| atom | 79 | NE2 | GLN | A | 7 | 17.176 | 8.240 | −13.667 | 1.00 | 63.60 | A |
| atom | 80 | C | GLN | A | 7 | 17.982 | 6.567 | −8.542 | 1.00 | 52.89 | A |
| atom | 81 | O | GLN | A | 7 | 17.831 | 7.289 | −7.560 | 1.00 | 56.01 | A |
| atom | 82 | N | CYS | A | 8 | 17.814 | 5.248 | −8.498 | 1.00 | 56.56 | A |
| atom | 83 | CA | CYS | A | 8 | 17.344 | 4.573 | −7.284 | 1.00 | 57.62 | A |
| atom | 84 | CB | CYS | A | 8 | 15.996 | 3.940 | −7.553 | 1.00 | 63.28 | A |
| atom | 85 | SG | CYS | A | 8 | 15.683 | 2.467 | −6.567 | 1.00 | 74.56 | A |
| atom | 86 | C | CYS | A | 8 | 18.262 | 3.528 | −6.647 | 1.00 | 56.08 | A |
| atom | 87 | O | CYS | A | 8 | 18.208 | 3.320 | −5.438 | 1.00 | 54.96 | A |
| atom | 88 | N | PHE | A | 9 | 19.074 | 2.833 | −7.428 | 1.00 | 53.84 | A |
| atom | 89 | CA | PHE | A | 9 | 19.979 | 1.915 | −6.776 | 1.00 | 53.37 | A |
| atom | 90 | CB | PHE | A | 9 | 20.061 | 0.530 | −7.463 | 1.00 | 52.01 | A |
| atom | 91 | CG | PHE | A | 9 | 18.795 | −0.252 | −7.378 | 1.00 | 48.64 | A |
| atom | 92 | CD1 | PHE | A | 9 | 17.768 | −0.011 | −8.283 | 1.00 | 46.82 | A |
| atom | 93 | CD2 | PHE | A | 9 | 18.597 | −1.184 | −6.368 | 1.00 | 47.14 | A |
| atom | 94 | CE1 | PHE | A | 9 | 16.550 | −0.683 | −8.187 | 1.00 | 48.45 | A |
| atom | 95 | CE2 | PHE | A | 9 | 17.375 | −1.870 | −6.258 | 1.00 | 48.65 | A |
| atom | 96 | CZ | PHE | A | 9 | 16.350 | −1.610 | −7.177 | 1.00 | 46.42 | A |
| atom | 97 | C | PHE | A | 9 | 21.313 | 2.606 | −6.824 | 1.00 | 54.11 | A |
| atom | 98 | O | PHE | A | 9 | 21.534 | 3.531 | −7.600 | 1.00 | 51.32 | A |
| atom | 99 | N | ASN | A | 10 | 22.180 | 2.128 | −5.950 | 1.00 | 55.46 | A |
| atom | 100 | CA | ASN | A | 10 | 23.553 | 2.569 | −5.791 | 1.00 | 55.38 | A |
| atom | 101 | CB | ASN | A | 10 | 24.150 | 1.710 | −4.674 | 1.00 | 58.76 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| | | | | | | | | | | | |
|---|---|---|---|---|---|---|---|---|---|---|---|
| atom | 102 | CG | ASN | A | 10 | 25.644 | 1.749 | −4.631 | 1.00 | 60.59 | A |
| atom | 103 | OD1 | ASN | A | 10 | 26.231 | 2.300 | −3.705 | 1.00 | 65.69 | A |
| atom | 104 | ND2 | ASN | A | 10 | 26.278 | 1.147 | −5.626 | 1.00 | 63.98 | A |
| atom | 105 | C | ASN | A | 10 | 24.233 | 2.345 | −7.143 | 1.00 | 54.66 | A |
| atom | 106 | O | ASN | A | 10 | 23.922 | 1.377 | −7.806 | 1.00 | 52.86 | A |
| atom | 107 | N | PRO | A | 11 | 25.168 | 3.224 | −7.562 | 1.00 | 53.42 | A |
| atom | 108 | CD | PRO | A | 11 | 25.728 | 4.370 | −6.826 | 1.00 | 52.23 | A |
| atom | 109 | CA | PRO | A | 11 | 25.850 | 3.066 | −8.862 | 1.00 | 51.84 | A |
| atom | 110 | CB | PRO | A | 11 | 26.834 | 4.236 | −8.884 | 1.00 | 49.10 | A |
| atom | 111 | CG | PRO | A | 11 | 26.220 | 5.235 | −7.960 | 1.00 | 50.95 | A |
| atom | 112 | C | PRO | A | 11 | 26.572 | 1.730 | −9.082 | 1.00 | 50.92 | A |
| atom | 113 | O | PRO | A | 11 | 26.671 | 1.243 | −10.208 | 1.00 | 54.87 | A |
| atom | 114 | N | MET | A | 12 | 27.098 | 1.176 | −7.992 | 1.00 | 47.95 | A |
| atom | 115 | CA | MET | A | 12 | 27.839 | −0.094 | −7.971 | 1.00 | 48.68 | A |
| atom | 116 | CB | MET | A | 12 | 28.486 | −0.252 | −6.591 | 1.00 | 50.45 | A |
| atom | 117 | CG | MET | A | 12 | 29.802 | −1.013 | −6.529 | 1.00 | 55.26 | A |
| atom | 118 | SD | MET | A | 12 | 30.234 | −1.375 | −4.804 | 1.00 | 63.75 | A |
| atom | 119 | CE | MET | A | 12 | 30.364 | 0.325 | −4.080 | 1.00 | 62.47 | A |
| atom | 120 | C | MET | A | 12 | 26.905 | −1.296 | −8.266 | 1.00 | 47.20 | A |
| atom | 121 | O | MET | A | 12 | 27.234 | −2.143 | −9.104 | 1.00 | 46.03 | A |
| atom | 122 | N | ILE | A | 13 | 25.756 | −1.351 | −7.581 | 1.00 | 45.58 | A |
| atom | 123 | CA | ILE | A | 13 | 24.754 | −2.408 | −7.754 | 1.00 | 45.11 | A |
| atom | 124 | CB | ILE | A | 13 | 23.474 | −2.146 | −6.844 | 1.00 | 43.43 | A |
| atom | 125 | CG2 | ILE | A | 13 | 22.386 | −3.175 | −7.143 | 1.00 | 39.78 | A |
| atom | 126 | CG1 | ILE | A | 13 | 23.832 | −2.098 | −5.357 | 1.00 | 38.45 | A |
| atom | 127 | CD1 | ILE | A | 13 | 24.402 | −3.328 | −4.828 | 1.00 | 39.15 | A |
| atom | 128 | C | ILE | A | 13 | 24.338 | −2.386 | −9.230 | 1.00 | 45.07 | A |
| atom | 129 | O | ILE | A | 13 | 24.360 | −3.415 | −9.911 | 1.00 | 46.72 | A |
| atom | 130 | N | VAL | A | 14 | 23.991 | −1.204 | −9.732 | 1.00 | 43.32 | A |
| atom | 131 | CA | VAL | A | 14 | 23.580 | −1.079 | −11.132 | 1.00 | 45.47 | A |
| atom | 132 | CB | VAL | A | 14 | 23.142 | 0.388 | −11.476 | 1.00 | 43.81 | A |
| atom | 133 | CG1 | VAL | A | 14 | 23.105 | 0.615 | −12.988 | 1.00 | 46.88 | A |
| atom | 134 | CG2 | VAL | A | 14 | 21.771 | 0.658 | −10.909 | 1.00 | 44.25 | A |
| atom | 135 | C | VAL | A | 14 | 24.658 | −1.524 | −12.099 | 1.00 | 47.57 | A |
| atom | 136 | O | VAL | A | 14 | 24.381 | −2.175 | −13.112 | 1.00 | 48.49 | A |
| atom | 137 | N | GLU | A | 15 | 25.895 | −1.166 | −11.782 | 1.00 | 49.11 | A |
| atom | 138 | CA | GLU | A | 15 | 27.009 | −1.549 | −12.635 | 1.00 | 50.47 | A |
| atom | 139 | CB | GLU | A | 15 | 28.266 | −0.751 | −12.238 | 1.00 | 52.20 | A |
| atom | 140 | CG | GLU | A | 15 | 28.869 | 0.117 | −13.377 | 1.00 | 60.18 | A |
| atom | 141 | CD | GLU | A | 15 | 27.971 | 1.285 | −13.861 | 1.00 | 65.65 | A |
| atom | 142 | OE1 | GLU | A | 15 | 28.311 | 2.459 | −13.573 | 1.00 | 66.66 | A |
| atom | 143 | OE2 | GLU | A | 15 | 26.942 | 1.057 | −14.550 | 1.00 | 65.06 | A |
| atom | 144 | C | GLU | A | 15 | 27.197 | −3.081 | −12.610 | 1.00 | 47.67 | A |
| atom | 145 | O | GLU | A | 15 | 27.290 | −3.691 | −13.656 | 1.00 | 47.11 | A |
| atom | 146 | N | LEU | A | 16 | 27.186 | −3.699 | −11.429 | 1.00 | 46.20 | A |
| atom | 147 | CA | LEU | A | 16 | 27.291 | −5.165 | −11.316 | 1.00 | 45.45 | A |
| atom | 148 | CB | LEU | A | 16 | 27.378 | −5.592 | −9.823 | 1.00 | 42.50 | A |
| atom | 149 | CG | LEU | A | 16 | 28.597 | −5.225 | −8.964 | 1.00 | 38.79 | A |
| atom | 150 | CD1 | LEU | A | 16 | 28.341 | −5.482 | −7.478 | 1.00 | 31.13 | A |
| atom | 151 | CD2 | LEU | A | 16 | 29.738 | −6.063 | −9.452 | 1.00 | 34.24 | A |
| atom | 152 | C | LEU | A | 16 | 26.109 | −5.886 | −12.013 | 1.00 | 45.51 | A |
| atom | 153 | O | LEU | A | 16 | 26.266 | −6.972 | −12.571 | 1.00 | 46.65 | A |
| atom | 154 | N | ALA | A | 17 | 24.930 | −5.272 | −11.999 | 1.00 | 43.51 | A |
| atom | 155 | CA | ALA | A | 17 | 23.757 | −5.871 | −12.664 | 1.00 | 46.11 | A |
| atom | 156 | CB | ALA | A | 17 | 22.433 | −5.278 | −12.114 | 1.00 | 42.78 | A |
| atom | 157 | C | ALA | A | 17 | 23.792 | −5.735 | −14.189 | 1.00 | 46.51 | A |
| atom | 158 | O | ALA | A | 17 | 23.214 | −6.548 | −14.923 | 1.00 | 47.54 | A |
| atom | 159 | N | GLU | A | 18 | 24.464 | −4.692 | −14.662 | 1.00 | 45.60 | A |
| atom | 160 | CA | GLU | A | 18 | 24.618 | −4.498 | −16.098 | 1.00 | 46.17 | A |
| atom | 161 | CB | GLU | A | 18 | 25.198 | −3.107 | −16.416 | 1.00 | 48.87 | A |
| atom | 162 | CG | GLU | A | 18 | 24.120 | −2.177 | −16.971 | 1.00 | 53.41 | A |
| atom | 163 | CD | GLU | A | 18 | 24.449 | −0.706 | −16.925 | 1.00 | 58.79 | A |
| atom | 164 | OE1 | GLU | A | 18 | 24.917 | −0.252 | −15.865 | 1.00 | 61.00 | A |
| atom | 165 | OE2 | GLU | A | 18 | 24.215 | −0.018 | −17.947 | 1.00 | 59.74 | A |
| atom | 166 | C | GLU | A | 18 | 25.506 | −5.637 | −16.585 | 1.00 | 46.33 | A |
| atom | 167 | O | GLU | A | 18 | 25.126 | −6.350 | −17.509 | 1.00 | 47.38 | A |
| atom | 168 | N | LYS | A | 19 | 26.632 | −5.868 | −15.906 | 1.00 | 46.80 | A |
| atom | 169 | CA | LYS | A | 19 | 27.526 | −6.963 | −16.293 | 1.00 | 44.28 | A |
| atom | 170 | CB | LYS | A | 19 | 28.834 | −6.968 | −15.442 | 1.00 | 45.41 | A |
| atom | 171 | CG | LYS | A | 19 | 29.452 | −5.589 | −14.958 | 1.00 | 49.67 | A |
| atom | 172 | CD | LYS | A | 19 | 30.367 | −4.863 | −15.995 | 1.00 | 55.59 | A |
| atom | 173 | CE | LYS | A | 19 | 31.055 | −3.537 | −15.484 | 1.00 | 59.67 | A |
| atom | 174 | NZ | LYS | A | 19 | 30.276 | −2.241 | −15.374 | 1.00 | 62.02 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| atom | 175 | C | LYS | A | 19 | 26.805 | −8.340 | −16.151 | 1.00 | 43.48 | A |
|---|---|---|---|---|---|---|---|---|---|---|---|
| atom | 176 | O | LYS | A | 19 | 26.945 | −9.199 | −17.012 | 1.00 | 44.22 | A |
| atom | 177 | N | ALA | A | 20 | 26.031 | −8.555 | −15.087 | 1.00 | 40.80 | A |
| atom | 178 | CA | ALA | A | 20 | 25.341 | −9.851 | −14.950 | 1.00 | 38.48 | A |
| atom | 179 | CB | ALA | A | 20 | 24.496 | −9.913 | −13.662 | 1.00 | 32.85 | A |
| atom | 180 | C | ALA | A | 20 | 24.464 | −10.130 | −16.157 | 1.00 | 39.83 | A |
| atom | 181 | O | ALA | A | 20 | 24.339 | −11.273 | −16.614 | 1.00 | 41.50 | A |
| atom | 182 | N | MET | A | 21 | 23.874 | −9.062 | −16.680 | 1.00 | 41.34 | A |
| atom | 183 | CA | MET | A | 21 | 23.000 | −9.122 | −17.853 | 1.00 | 43.95 | A |
| atom | 184 | CB | MET | A | 21 | 22.110 | −7.867 | −17.874 | 1.00 | 42.74 | A |
| atom | 185 | CG | MET | A | 21 | 21.032 | −7.878 | −16.782 | 1.00 | 40.72 | A |
| atom | 186 | SD | MET | A | 21 | 19.675 | −6.771 | −17.157 | 1.00 | 42.46 | A |
| atom | 187 | CE | MET | A | 21 | 18.628 | −7.810 | −18.333 | 1.00 | 37.53 | A |
| atom | 188 | C | MET | A | 21 | 23.720 | −9.314 | −19.209 | 1.00 | 44.45 | A |
| atom | 189 | O | MET | A | 21 | 23.486 | −10.303 | −19.902 | 1.00 | 43.76 | A |
| atom | 190 | N | LYS | A | 22 | 24.615 | −8.386 | −19.555 | 1.00 | 46.28 | A |
| atom | 191 | CA | LYS | A | 22 | 25.378 | −8.418 | −20.811 | 1.00 | 48.64 | A |
| atom | 192 | CB | LYS | A | 22 | 26.303 | −7.199 | −20.872 | 1.00 | 49.17 | A |
| atom | 193 | CG | LYS | A | 22 | 25.548 | −5.878 | −20.753 | 1.00 | 50.98 | A |
| atom | 194 | CD | LYS | A | 22 | 26.451 | −4.667 | −20.927 | 1.00 | 55.86 | A |
| atom | 195 | CE | LYS | A | 22 | 27.480 | −4.578 | −19.811 | 1.00 | 55.75 | A |
| atom | 196 | NZ | LYS | A | 22 | 27.643 | −3.181 | −19.315 | 1.00 | 58.63 | A |
| atom | 197 | C | LYS | A | 22 | 26.168 | −9.719 | −21.027 | 1.00 | 50.64 | A |
| atom | 198 | O | LYS | A | 22 | 26.430 | −10.118 | −22.169 | 1.00 | 51.65 | A |
| atom | 199 | N | GLU | A | 23 | 26.526 | −10.372 | −19.917 | 1.00 | 53.81 | A |
| atom | 200 | CA | GLU | A | 23 | 27.255 | −11.653 | −19.908 | 1.00 | 54.64 | A |
| atom | 201 | CB | GLU | A | 23 | 27.688 | −12.026 | −18.468 | 1.00 | 54.60 | A |
| atom | 202 | CG | GLU | A | 23 | 27.981 | −13.535 | −18.265 | 1.00 | 57.32 | A |
| atom | 203 | CD | GLU | A | 23 | 28.482 | −13.893 | −16.860 | 1.00 | 56.55 | A |
| atom | 204 | OE1 | GLU | A | 23 | 28.285 | −13.095 | −15.921 | 1.00 | 60.36 | A |
| atom | 205 | OE2 | GLU | A | 23 | 29.075 | −14.982 | −16.696 | 1.00 | 53.41 | A |
| atom | 206 | C | GLU | A | 23 | 26.338 | −12.725 | −20.460 | 1.00 | 53.54 | A |
| atom | 207 | O | GLU | A | 23 | 26.763 | −13.809 | −20.830 | 1.00 | 52.19 | A |
| atom | 208 | N | TYR | A | 24 | 25.055 | −12.402 | −20.501 | 1.00 | 54.56 | A |
| atom | 209 | CA | TYR | A | 24 | 24.063 | −13.336 | −21.027 | 1.00 | 56.31 | A |
| atom | 210 | CB | TYR | A | 24 | 23.029 | −13.708 | −19.958 | 1.00 | 57.66 | A |
| atom | 211 | CG | TYR | A | 24 | 23.589 | −14.649 | −18.926 | 1.00 | 64.03 | A |
| atom | 212 | CD1 | TYR | A | 24 | 24.298 | −14.170 | −17.825 | 1.00 | 65.84 | A |
| atom | 213 | CE1 | TYR | A | 24 | 24.877 | −15.044 | −16.912 | 1.00 | 66.64 | A |
| atom | 214 | CD2 | TYR | A | 24 | 23.480 | −16.026 | −19.090 | 1.00 | 65.92 | A |
| atom | 215 | CE2 | TYR | A | 24 | 24.065 | −16.909 | −18.186 | 1.00 | 66.70 | A |
| atom | 216 | CZ | TYR | A | 24 | 24.760 | −16.415 | −17.104 | 1.00 | 68.77 | A |
| atom | 217 | OH | TYR | A | 24 | 25.322 | −17.293 | −16.198 | 1.00 | 67.91 | A |
| atom | 218 | C | TYR | A | 24 | 23.351 | −12.774 | −22.240 | 1.00 | 55.08 | A |
| atom | 219 | O | TYR | A | 24 | 22.244 | −13.188 | −22.579 | 1.00 | 55.69 | A |
| atom | 220 | N | GLY | A | 25 | 24.002 | −11.828 | −22.898 | 1.00 | 54.51 | A |
| atom | 221 | CA | GLY | A | 25 | 23.396 | −11.228 | −24.061 | 1.00 | 53.11 | A |
| atom | 222 | C | GLY | A | 25 | 22.022 | −10.770 | −23.655 | 1.00 | 52.36 | A |
| atom | 223 | O | GLY | A | 25 | 21.013 | −11.165 | −24.229 | 1.00 | 53.34 | A |
| atom | 224 | N | GLU | A | 26 | 21.983 | −9.977 | −22.602 | 1.00 | 51.94 | A |
| atom | 225 | CA | GLU | A | 26 | 20.727 | −9.441 | −22.153 | 1.00 | 51.53 | A |
| atom | 226 | CB | GLU | A | 26 | 20.298 | −10.028 | −20.791 | 1.00 | 54.80 | A |
| atom | 227 | CG | GLU | A | 26 | 19.047 | −10.937 | −20.924 | 1.00 | 55.63 | A |
| atom | 228 | CD | GLU | A | 26 | 18.834 | −11.916 | −19.764 | 1.00 | 58.44 | A |
| atom | 229 | OE1 | GLU | A | 26 | 17.778 | −12.595 | −19.725 | 1.00 | 58.82 | A |
| atom | 230 | OE2 | GLU | A | 26 | 19.724 | −12.023 | −18.897 | 1.00 | 58.97 | A |
| atom | 231 | C | GLU | A | 26 | 21.094 | −7.985 | −22.113 | 1.00 | 50.05 | A |
| atom | 232 | O | GLU | A | 26 | 22.167 | −7.584 | −21.639 | 1.00 | 50.48 | A |
| atom | 233 | N | ASP | A | 27 | 20.229 | −7.216 | −22.730 | 1.00 | 47.66 | A |
| atom | 234 | CA | ASP | A | 27 | 20.426 | −5.818 | −22.828 | 1.00 | 44.83 | A |
| atom | 235 | CB | ASP | A | 27 | 19.920 | −5.397 | −24.202 | 1.00 | 44.18 | A |
| atom | 236 | CG | ASP | A | 27 | 20.345 | −4.028 | −24.586 | 1.00 | 44.77 | A |
| atom | 237 | OD1 | ASP | A | 27 | 20.673 | −3.855 | −25.773 | 1.00 | 47.00 | A |
| atom | 238 | OD2 | ASP | A | 27 | 20.333 | −3.135 | −23.715 | 1.00 | 42.36 | A |
| atom | 239 | C | ASP | A | 27 | 19.595 | −5.228 | −21.700 | 1.00 | 43.93 | A |
| atom | 240 | O | ASP | A | 27 | 18.425 | −5.558 | −21.529 | 1.00 | 43.85 | A |
| atom | 241 | N | PRO | A | 28 | 20.221 | −4.404 | −20.860 | 1.00 | 42.74 | A |
| atom | 242 | CD | PRO | A | 28 | 21.681 | −4.466 | −20.723 | 1.00 | 40.77 | A |
| atom | 243 | CA | PRO | A | 28 | 19.571 | −3.746 | −19.723 | 1.00 | 41.90 | A |
| atom | 244 | CB | PRO | A | 28 | 20.723 | −3.059 | −18.974 | 1.00 | 42.27 | A |
| atom | 245 | CG | PRO | A | 28 | 21.985 | −3.481 | −19.663 | 1.00 | 41.06 | A |
| atom | 246 | C | PRO | A | 28 | 18.503 | −2.764 | −20.181 | 1.00 | 41.23 | A |
| atom | 247 | O | PRO | A | 28 | 17.531 | −2.533 | −19.464 | 1.00 | 42.06 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| | | | | | | | | | | |
|---|---|---|---|---|---|---|---|---|---|---|
| atom | 248 | N | LYS | A | 29 | 18.677 | −2.221 | −21.390 | 1.00 | 41.53 | A |
| atom | 249 | CA | LYS | A | 29 | 17.735 | −1.249 | −21.959 | 1.00 | 39.49 | A |
| atom | 250 | CB | LYS | A | 29 | 18.395 | −0.407 | −23.052 | 1.00 | 44.02 | A |
| atom | 251 | CG | LYS | A | 29 | 19.184 | 0.767 | −22.527 | 1.00 | 44.99 | A |
| atom | 252 | CD | LYS | A | 29 | 19.978 | 1.395 | −23.644 | 1.00 | 47.86 | A |
| atom | 253 | CE | LYS | A | 29 | 20.373 | 2.812 | −23.280 | 1.00 | 51.87 | A |
| atom | 254 | NZ | LYS | A | 29 | 19.196 | 3.714 | −23.171 | 1.00 | 53.96 | A |
| atom | 255 | C | LYS | A | 29 | 16.452 | −1.829 | −22.538 | 1.00 | 39.01 | A |
| atom | 256 | O | LYS | A | 29 | 15.432 | −1.153 | −22.597 | 1.00 | 32.75 | A |
| atom | 257 | N | ILE | A | 30 | 16.503 | −3.073 | −22.989 | 1.00 | 40.47 | A |
| atom | 258 | CA | ILE | A | 30 | 15.321 | −3.696 | −23.569 | 1.00 | 40.91 | A |
| atom | 259 | CB | ILE | A | 30 | 15.708 | −4.749 | −24.638 | 1.00 | 37.22 | A |
| atom | 260 | CG2 | ILE | A | 30 | 14.462 | −5.541 | −25.065 | 1.00 | 38.23 | A |
| atom | 261 | CG1 | ILE | A | 30 | 16.372 | −4.050 | −25.822 | 1.00 | 32.15 | A |
| atom | 262 | CD1 | ILE | A | 30 | 17.028 | −4.998 | −26.797 | 1.00 | 35.02 | A |
| atom | 263 | C | ILE | A | 30 | 14.579 | −4.395 | −22.437 | 1.00 | 43.92 | A |
| atom | 264 | O | ILE | A | 30 | 13.358 | −4.231 | −22.269 | 1.00 | 44.73 | A |
| atom | 265 | N | GLU | A | 31 | 15.363 | −5.144 | −21.663 | 1.00 | 42.61 | A |
| atom | 266 | CA | GLU | A | 31 | 14.887 | −5.939 | −20.552 | 1.00 | 43.14 | A |
| atom | 267 | CB | GLU | A | 31 | 15.675 | −7.211 | −20.565 | 1.00 | 46.36 | A |
| atom | 268 | CG | GLU | A | 31 | 15.539 | −7.959 | −21.834 | 1.00 | 52.65 | A |
| atom | 269 | CD | GLU | A | 31 | 14.816 | −9.236 | −21.582 | 1.00 | 58.46 | A |
| atom | 270 | OE1 | GLU | A | 31 | 13.567 | −9.214 | −21.527 | 1.00 | 61.85 | A |
| atom | 271 | OE2 | GLU | A | 31 | 15.502 | −10.263 | −21.398 | 1.00 | 61.65 | A |
| atom | 272 | C | GLU | A | 31 | 14.980 | −5.316 | −19.164 | 1.00 | 40.85 | A |
| atom | 273 | O | GLU | A | 31 | 15.566 | −5.902 | −18.249 | 1.00 | 38.71 | A |
| atom | 274 | N | THR | A | 32 | 14.359 | −4.155 | −19.015 | 1.00 | 39.14 | A |
| atom | 275 | CA | THR | A | 32 | 14.350 | −3.387 | −17.781 | 1.00 | 37.11 | A |
| atom | 276 | CB | THR | A | 32 | 13.732 | −2.025 | −18.062 | 1.00 | 40.05 | A |
| atom | 277 | OG1 | THR | A | 32 | 12.505 | −2.185 | −18.782 | 1.00 | 40.87 | A |
| atom | 278 | CG2 | THR | A | 32 | 14.692 | −1.190 | −18.916 | 1.00 | 33.55 | A |
| atom | 279 | C | THR | A | 32 | 13.720 | −3.976 | −16.512 | 1.00 | 36.64 | A |
| atom | 280 | O | THR | A | 32 | 14.149 | −3.640 | −15.414 | 1.00 | 34.19 | A |
| atom | 281 | N | ASN | A | 33 | 12.712 | −4.839 | −16.644 | 1.00 | 38.30 | A |
| atom | 282 | CA | ASN | A | 33 | 12.089 | −5.437 | −15.472 | 1.00 | 37.16 | A |
| atom | 283 | CB | ASN | A | 33 | 10.723 | −6.063 | −15.841 | 1.00 | 36.89 | A |
| atom | 284 | CG | ASN | A | 33 | 9.575 | −5.048 | −15.775 | 1.00 | 33.43 | A |
| atom | 285 | OD1 | ASN | A | 33 | 9.716 | −3.986 | −15.162 | 1.00 | 30.32 | A |
| atom | 286 | ND2 | ASN | A | 33 | 8.425 | −5.386 | −16.368 | 1.00 | 31.48 | A |
| atom | 287 | C | ASN | A | 33 | 13.033 | −6.424 | −14.762 | 1.00 | 39.07 | A |
| atom | 288 | O | ASN | A | 33 | 12.977 | −6.533 | −13.532 | 1.00 | 41.04 | A |
| atom | 289 | N | LYS | A | 34 | 13.920 | −7.115 | −15.484 | 1.00 | 39.80 | A |
| atom | 290 | CA | LYS | A | 34 | 14.854 | −8.004 | −14.772 | 1.00 | 41.50 | A |
| atom | 291 | CB | LYS | A | 34 | 15.303 | −9.145 | −15.632 | 1.00 | 41.51 | A |
| atom | 292 | CG | LYS | A | 34 | 15.046 | −8.929 | −17.080 | 1.00 | 47.03 | A |
| atom | 293 | CD | LYS | A | 34 | 15.873 | −9.871 | −17.913 | 1.00 | 51.64 | A |
| atom | 294 | CE | LYS | A | 34 | 15.873 | −11.292 | −17.352 | 1.00 | 51.85 | A |
| atom | 295 | NZ | LYS | A | 34 | 16.923 | −11.545 | −16.313 | 1.00 | 54.15 | A |
| atom | 296 | C | LYS | A | 34 | 16.071 | −7.210 | −14.322 | 1.00 | 41.53 | A |
| atom | 297 | O | LYS | A | 34 | 16.649 | −7.483 | −13.266 | 1.00 | 43.70 | A |
| atom | 298 | N | PHE | A | 35 | 16.460 | −6.221 | −15.126 | 1.00 | 39.89 | A |
| atom | 299 | CA | PHE | A | 35 | 17.579 | −5.332 | −14.760 | 1.00 | 38.55 | A |
| atom | 300 | CB | PHE | A | 35 | 17.688 | −4.218 | −15.849 | 1.00 | 36.62 | A |
| atom | 301 | CG | PHE | A | 35 | 18.642 | −3.077 | −15.554 | 1.00 | 37.12 | A |
| atom | 302 | CD1 | PHE | A | 35 | 18.310 | −1.799 | −16.017 | 1.00 | 37.37 | A |
| atom | 303 | CD2 | PHE | A | 35 | 19.823 | −3.230 | −14.823 | 1.00 | 36.94 | A |
| atom | 304 | CE1 | PHE | A | 35 | 19.161 | −0.701 | −15.784 | 1.00 | 43.08 | A |
| atom | 305 | CE2 | PHE | A | 35 | 20.664 | −2.133 | −14.593 | 1.00 | 37.85 | A |
| atom | 306 | CZ | PHE | A | 35 | 20.310 | −0.873 | −15.068 | 1.00 | 38.28 | A |
| atom | 307 | C | PHE | A | 35 | 17.163 | −4.886 | −13.324 | 1.00 | 36.20 | A |
| atom | 308 | O | PHE | A | 35 | 17.878 | −5.160 | −12.371 | 1.00 | 36.26 | A |
| atom | 309 | N | ALA | A | 36 | 15.964 | −4.338 | −13.133 | 1.00 | 34.83 | A |
| atom | 310 | CA | ALA | A | 36 | 15.559 | −3.976 | −11.755 | 1.00 | 31.80 | A |
| atom | 311 | CB | ALA | A | 36 | 14.202 | −3.270 | −11.758 | 1.00 | 27.32 | A |
| atom | 312 | C | ALA | A | 36 | 15.536 | −5.184 | −10.768 | 1.00 | 30.83 | A |
| atom | 313 | O | ALA | A | 36 | 15.932 | −5.057 | −9.596 | 1.00 | 27.25 | A |
| atom | 314 | N | ALA | A | 37 | 15.086 | −6.351 | −11.246 | 1.00 | 30.32 | A |
| atom | 315 | CA | ALA | A | 37 | 15.066 | −7.569 | −10.409 | 1.00 | 30.71 | A |
| atom | 316 | CB | ALA | A | 37 | 14.353 | −8.730 | −11.140 | 1.00 | 28.33 | A |
| atom | 317 | C | ALA | A | 37 | 16.488 | −7.991 | −10.032 | 1.00 | 30.07 | A |
| atom | 318 | O | ALA | A | 37 | 16.752 | −8.434 | −8.919 | 1.00 | 30.03 | A |
| atom | 319 | N | ILE | A | 38 | 17.408 | −7.864 | −10.977 | 1.00 | 33.99 | A |
| atom | 320 | CA | ILE | A | 38 | 18.795 | −8.212 | −10.695 | 1.00 | 36.57 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| | | | | | | | | | | | |
|---|---|---|---|---|---|---|---|---|---|---|---|
| atom | 321 | CB | ILE | A | 38 | 19.719 | −8.127 | −11.962 | 1.00 | 36.34 | A |
| atom | 322 | CG2 | ILE | A | 38 | 21.169 | −8.294 | −11.533 | 1.00 | 35.22 | A |
| atom | 323 | CG1 | ILE | A | 38 | 19.363 | −9.223 | −12.985 | 1.00 | 36.70 | A |
| atom | 324 | CD1 | ILE | A | 38 | 18.349 | −10.255 | −12.507 | 1.00 | 39.19 | A |
| atom | 325 | C | ILE | A | 38 | 19.343 | −7.299 | −9.615 | 1.00 | 35.29 | A |
| atom | 326 | O | ILE | A | 38 | 19.920 | −7.768 | −8.657 | 1.00 | 38.26 | A |
| atom | 327 | N | CYS | A | 39 | 19.107 | −5.998 | −9.753 | 1.00 | 37.22 | A |
| atom | 328 | CA | CYS | A | 39 | 19.582 | −4.992 | −8.788 | 1.00 | 34.88 | A |
| atom | 329 | CB | CYS | A | 39 | 19.216 | −3.570 | −9.251 | 1.00 | 33.48 | A |
| atom | 330 | SG | CYS | A | 39 | 19.977 | −3.015 | −10.800 | 1.00 | 42.93 | A |
| atom | 331 | C | CYS | A | 39 | 19.082 | −5.158 | −7.358 | 1.00 | 32.00 | A |
| atom | 332 | O | CYS | A | 39 | 19.844 | −5.057 | −6.414 | 1.00 | 35.64 | A |
| atom | 333 | N | THR | A | 40 | 17.790 | −5.412 | −7.219 | 1.00 | 31.07 | A |
| atom | 334 | CA | THR | A | 40 | 17.144 | −5.584 | −5.923 | 1.00 | 28.40 | A |
| atom | 335 | CB | THR | A | 40 | 15.669 | −5.888 | −6.107 | 1.00 | 26.66 | A |
| atom | 336 | OG1 | THR | A | 40 | 15.103 | −4.888 | −6.952 | 1.00 | 31.71 | A |
| atom | 337 | CG2 | THR | A | 40 | 14.952 | −5.924 | −4.770 | 1.00 | 30.14 | A |
| atom | 338 | C | THR | A | 40 | 17.721 | −6.737 | −5.127 | 1.00 | 28.69 | A |
| atom | 339 | O | THR | A | 40 | 17.849 | −6.681 | −3.891 | 1.00 | 28.36 | A |
| atom | 340 | N | HIS | A | 41 | 18.020 | −7.802 | −5.860 | 1.00 | 27.91 | A |
| atom | 341 | CA | HIS | A | 41 | 18.545 | −9.034 | −5.294 | 1.00 | 28.27 | A |
| atom | 342 | CB | HIS | A | 41 | 18.352 | −10.176 | −6.279 | 1.00 | 25.16 | A |
| atom | 343 | CG | HIS | A | 41 | 19.159 | −11.381 | −5.946 | 1.00 | 22.38 | A |
| atom | 344 | CD2 | HIS | A | 41 | 19.019 | −12.294 | −4.962 | 1.00 | 23.88 | A |
| atom | 345 | ND1 | HIS | A | 41 | 20.273 | −11.745 | −6.665 | 1.00 | 23.29 | A |
| atom | 346 | CE1 | HIS | A | 41 | 20.785 | −12.841 | −6.137 | 1.00 | 24.39 | A |
| atom | 347 | NE2 | HIS | A | 41 | 20.045 | −13.195 | −5.102 | 1.00 | 24.18 | A |
| atom | 348 | C | HIS | A | 41 | 19.997 | −8.903 | −5.000 | 1.00 | 25.95 | A |
| atom | 349 | O | HIS | A | 41 | 20.539 | −9.524 | −4.112 | 1.00 | 26.54 | A |
| atom | 350 | N | LEU | A | 42 | 20.653 | −8.131 | −5.825 | 1.00 | 32.18 | A |
| atom | 351 | CA | LEU | A | 42 | 22.056 | −7.915 | −5.612 | 1.00 | 35.76 | A |
| atom | 352 | CB | LEU | A | 42 | 22.610 | −7.136 | −6.791 | 1.00 | 34.58 | A |
| atom | 353 | CG | LEU | A | 42 | 23.893 | −7.576 | −7.470 | 1.00 | 33.08 | A |
| atom | 354 | CD1 | LEU | A | 42 | 24.264 | −6.385 | −8.295 | 1.00 | 33.98 | A |
| atom | 355 | CD2 | LEU | A | 42 | 25.023 | −7.909 | −6.497 | 1.00 | 35.49 | A |
| atom | 356 | C | LEU | A | 42 | 22.067 | −7.094 | −4.313 | 1.00 | 37.40 | A |
| atom | 357 | O | LEU | A | 42 | 22.800 | −7.388 | −3.382 | 1.00 | 43.72 | A |
| atom | 358 | N | GLU | A | 43 | 21.177 | −6.109 | −4.222 | 1.00 | 39.03 | A |
| atom | 359 | CA | GLU | A | 43 | 21.116 | −5.258 | −3.027 | 1.00 | 40.12 | A |
| atom | 360 | CB | GLU | A | 43 | 20.155 | −4.058 | −3.216 | 1.00 | 43.45 | A |
| atom | 361 | CG | GLU | A | 43 | 20.610 | −2.802 | −2.429 | 1.00 | 48.40 | A |
| atom | 362 | CD | GLU | A | 43 | 19.638 | −1.623 | −2.508 | 1.00 | 51.64 | A |
| atom | 363 | OE1 | GLU | A | 43 | 19.272 | −1.182 | −3.622 | 1.00 | 56.54 | A |
| atom | 364 | OE2 | GLU | A | 43 | 19.245 | −1.114 | −1.440 | 1.00 | 52.79 | A |
| atom | 365 | C | GLU | A | 43 | 20.745 | −6.007 | −1.746 | 1.00 | 39.87 | A |
| atom | 366 | O | GLU | A | 43 | 21.152 | −5.596 | −0.659 | 1.00 | 41.49 | A |
| atom | 367 | N | VAL | A | 44 | 20.005 | −7.110 | −1.839 | 1.00 | 38.37 | A |
| atom | 368 | CA | VAL | A | 44 | 19.654 | −7.826 | −0.604 | 1.00 | 35.53 | A |
| atom | 369 | CB | VAL | A | 44 | 18.491 | −8.828 | −0.800 | 1.00 | 35.23 | A |
| atom | 370 | CG1 | VAL | A | 44 | 18.304 | −9.657 | 0.456 | 1.00 | 35.78 | A |
| atom | 371 | CG2 | VAL | A | 44 | 17.204 | −8.095 | −1.116 | 1.00 | 36.61 | A |
| atom | 372 | C | VAL | A | 44 | 20.858 | −8.621 | −0.123 | 1.00 | 36.04 | A |
| atom | 373 | O | VAL | A | 44 | 21.116 | −8.729 | 1.080 | 1.00 | 33.16 | A |
| atom | 374 | N | CYS | A | 45 | 21.583 | −9.172 | −1.090 | 1.00 | 34.25 | A |
| atom | 375 | CA | CYS | A | 45 | 22.764 | −9.963 | −0.819 | 1.00 | 35.83 | A |
| atom | 376 | CB | CYS | A | 45 | 23.336 | −10.476 | −2.141 | 1.00 | 35.02 | A |
| atom | 377 | SG | CYS | A | 45 | 22.362 | −11.813 | −2.936 | 1.00 | 40.03 | A |
| atom | 378 | C | CYS | A | 45 | 23.787 | −9.106 | −0.048 | 1.00 | 36.91 | A |
| atom | 379 | O | CYS | A | 45 | 24.556 | −9.603 | 0.785 | 1.00 | 33.76 | A |
| atom | 380 | N | PHE | A | 46 | 23.792 | −7.804 | −0.316 | 1.00 | 38.49 | A |
| atom | 381 | CA | PHE | A | 46 | 24.700 | −6.931 | 0.405 | 1.00 | 37.16 | A |
| atom | 382 | CB | PHE | A | 46 | 25.031 | −5.660 | −0.376 | 1.00 | 39.49 | A |
| atom | 383 | CG | PHE | A | 46 | 25.779 | −5.902 | −1.646 | 1.00 | 43.99 | A |
| atom | 384 | CD1 | PHE | A | 46 | 26.892 | −6.738 | −1.676 | 1.00 | 46.57 | A |
| atom | 385 | CD2 | PHE | A | 46 | 25.390 | −5.274 | −2.815 | 1.00 | 46.19 | A |
| atom | 386 | CE1 | PHE | A | 46 | 27.603 | −6.938 | −2.856 | 1.00 | 44.28 | A |
| atom | 387 | CE2 | PHE | A | 46 | 26.097 | −5.473 | −3.992 | 1.00 | 45.67 | A |
| atom | 388 | CZ | PHE | A | 46 | 27.203 | −6.307 | −4.010 | 1.00 | 40.31 | A |
| atom | 389 | C | PHE | A | 46 | 24.116 | −6.529 | 1.749 | 1.00 | 37.48 | A |
| atom | 390 | O | PHE | A | 46 | 24.830 | −6.485 | 2.745 | 1.00 | 37.98 | A |
| atom | 391 | N | MET | A | 47 | 22.825 | −6.242 | 1.813 | 1.00 | 36.87 | A |
| atom | 392 | CA | MET | A | 47 | 22.283 | −5.836 | 3.111 | 1.00 | 38.47 | A |
| atom | 393 | CB | MET | A | 47 | 20.777 | −5.631 | 3.039 | 1.00 | 37.55 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| atom | 394 | CG  | MET | A | 47 | 20.355 | −4.487  | 2.128  | 1.00 | 42.04 | A |
|------|-----|-----|-----|---|----|--------|---------|--------|------|-------|---|
| atom | 395 | SD  | MET | A | 47 | 18.766 | −3.804  | 2.560  | 1.00 | 43.14 | A |
| atom | 396 | CE  | MET | A | 47 | 17.614 | −4.743  | 1.404  | 1.00 | 43.24 | A |
| atom | 397 | C   | MET | A | 47 | 22.590 | −6.942  | 4.117  | 1.00 | 40.63 | A |
| atom | 398 | O   | MET | A | 47 | 23.003 | −6.697  | 5.257  | 1.00 | 42.62 | A |
| atom | 399 | N   | TYR | A | 48 | 22.404 | −8.163  | 3.623  | 1.00 | 39.69 | A |
| atom | 400 | CA  | TYR | A | 48 | 22.594 | −9.432  | 4.320  | 1.00 | 37.34 | A |
| atom | 401 | CB  | TYR | A | 48 | 21.958 | −10.517 | 3.409  | 1.00 | 38.09 | A |
| atom | 402 | CG  | TYR | A | 48 | 21.451 | −11.799 | 4.049  | 1.00 | 35.80 | A |
| atom | 403 | CD1 | TYR | A | 48 | 22.324 | −12.657 | 4.697  | 1.00 | 36.18 | A |
| atom | 404 | CE1 | TYR | A | 48 | 21.878 | −13.877 | 5.243  | 1.00 | 34.95 | A |
| atom | 405 | CD2 | TYR | A | 48 | 20.096 | −12.162 | 3.969  | 1.00 | 38.08 | A |
| atom | 406 | CE2 | TYR | A | 48 | 19.635 | −13.373 | 4.497  | 1.00 | 37.87 | A |
| atom | 407 | CZ  | TYR | A | 48 | 20.533 | −14.219 | 5.144  | 1.00 | 36.76 | A |
| atom | 408 | OH  | TYR | A | 48 | 20.080 | −15.407 | 5.657  | 1.00 | 35.00 | A |
| atom | 409 | C   | TYR | A | 48 | 24.027 | −9.820  | 4.775  | 1.00 | 37.15 | A |
| atom | 410 | O   | TYR | A | 48 | 24.174 | −10.424 | 5.839  | 1.00 | 34.29 | A |
| atom | 411 | N   | SER | A | 49 | 25.074 | −9.510  | 3.995  | 1.00 | 39.36 | A |
| atom | 412 | CA  | SER | A | 49 | 26.449 | −9.886  | 4.415  | 1.00 | 43.91 | A |
| atom | 413 | CB  | SER | A | 49 | 27.481 | −9.839  | 3.253  | 1.00 | 45.79 | A |
| atom | 414 | OG  | SER | A | 49 | 27.049 | −9.073  | 2.141  | 1.00 | 48.61 | A |
| atom | 415 | C   | SER | A | 49 | 27.017 | −9.082  | 5.580  | 1.00 | 44.28 | A |
| atom | 416 | O   | SER | A | 49 | 27.129 | −7.865  | 5.505  | 1.00 | 45.47 | A |
| atom | 417 | N   | ARG | A | 75 | 31.819 | −11.861 | 8.497  | 1.00 | 41.95 | A |
| atom | 418 | CA  | ARG | A | 75 | 31.154 | −13.133 | 8.780  | 1.00 | 42.91 | A |
| atom | 419 | CB  | ARG | A | 75 | 29.935 | −12.969 | 9.675  | 1.00 | 40.89 | A |
| atom | 420 | CG  | ARG | A | 75 | 29.152 | −14.320 | 9.740  | 1.00 | 46.35 | A |
| atom | 421 | CD  | ARG | A | 75 | 27.688 | −14.191 | 10.184 | 1.00 | 48.00 | A |
| atom | 422 | NE  | ARG | A | 75 | 26.961 | −15.466 | 10.264 | 1.00 | 49.52 | A |
| atom | 423 | CZ  | ARG | A | 75 | 25.854 | −15.613 | 10.985 | 1.00 | 49.57 | A |
| atom | 424 | NH1 | ARG | A | 75 | 25.400 | −14.572 | 11.660 | 1.00 | 49.18 | A |
| atom | 425 | NH2 | ARG | A | 75 | 25.187 | −16.762 | 11.026 | 1.00 | 47.00 | A |
| atom | 426 | C   | ARG | A | 75 | 30.618 | −13.816 | 7.544  | 1.00 | 44.58 | A |
| atom | 427 | O   | ARG | A | 75 | 30.443 | −15.035 | 7.517  | 1.00 | 42.56 | A |
| atom | 428 | N   | PHE | A | 76 | 30.286 | −13.001 | 6.559  | 1.00 | 44.38 | A |
| atom | 429 | CA  | PHE | A | 76 | 29.735 | −13.473 | 5.325  | 1.00 | 45.14 | A |
| atom | 430 | CB  | PHE | A | 76 | 28.437 | −12.736 | 5.047  | 1.00 | 42.47 | A |
| atom | 431 | CG  | PHE | A | 76 | 27.315 | −13.232 | 5.848  | 1.00 | 40.56 | A |
| atom | 432 | CD1 | PHE | A | 76 | 26.734 | −12.455 | 6.832  | 1.00 | 39.54 | A |
| atom | 433 | CD2 | PHE | A | 76 | 26.892 | −14.547 | 5.672  | 1.00 | 39.84 | A |
| atom | 434 | CE1 | PHE | A | 76 | 25.719 | −12.987 | 7.623  | 1.00 | 38.10 | A |
| atom | 435 | CE2 | PHE | A | 76 | 25.900 | −15.082 | 6.431  | 1.00 | 38.89 | A |
| atom | 436 | CZ  | PHE | A | 76 | 25.312 | −14.311 | 7.428  | 1.00 | 38.25 | A |
| atom | 437 | C   | PHE | A | 76 | 30.707 | −13.170 | 4.244  | 1.00 | 47.00 | A |
| atom | 438 | O   | PHE | A | 76 | 31.500 | −12.255 | 4.383  | 1.00 | 47.41 | A |
| atom | 439 | N   | GLU | A | 77 | 30.653 | −13.914 | 3.149  | 1.00 | 48.93 | A |
| atom | 440 | CA  | GLU | A | 77 | 31.534 | −13.617 | 2.026  | 1.00 | 51.25 | A |
| atom | 441 | CB  | GLU | A | 77 | 32.574 | −14.744 | 1.834  | 1.00 | 48.93 | A |
| atom | 442 | CG  | GLU | A | 77 | 33.329 | −14.713 | 0.502  | 1.00 | 53.34 | A |
| atom | 443 | CD  | GLU | A | 77 | 34.294 | −13.538 | 0.364  | 1.00 | 58.18 | A |
| atom | 444 | OE1 | GLU | A | 77 | 35.426 | −13.613 | 0.895  | 1.00 | 57.63 | A |
| atom | 445 | OE2 | GLU | A | 77 | 33.919 | −12.531 | −0.278 | 1.00 | 61.59 | A |
| atom | 446 | C   | GLU | A | 77 | 30.592 | −13.497 | 0.827  | 1.00 | 52.25 | A |
| atom | 447 | O   | GLU | A | 77 | 29.837 | −14.440 | 0.569  | 1.00 | 52.35 | A |
| atom | 448 | N   | ILE | A | 78 | 30.588 | −12.347 | 0.126  | 1.00 | 54.08 | A |
| atom | 449 | CA  | ILE | A | 78 | 29.705 | −12.209 | −1.050 | 1.00 | 52.39 | A |
| atom | 450 | CB  | ILE | A | 78 | 29.509 | −10.778 | −1.676 | 1.00 | 53.38 | A |
| atom | 451 | CG2 | ILE | A | 78 | 28.031 | −10.589 | −2.048 | 1.00 | 53.24 | A |
| atom | 452 | CG1 | ILE | A | 78 | 30.100 | −9.676  | −0.803 | 1.00 | 55.99 | A |
| atom | 453 | CD1 | ILE | A | 78 | 29.107 | −8.842  | −0.067 | 1.00 | 55.00 | A |
| atom | 454 | C   | ILE | A | 78 | 30.313 | −12.941 | −2.216 | 1.00 | 51.21 | A |
| atom | 455 | O   | ILE | A | 78 | 31.487 | −12.754 | −2.543 | 1.00 | 53.03 | A |
| atom | 456 | N   | ILE | A | 79 | 29.469 | −13.728 | −2.864 | 1.00 | 47.56 | A |
| atom | 457 | CA  | ILE | A | 79 | 29.812 | −14.518 | −4.032 | 1.00 | 43.50 | A |
| atom | 458 | CB  | ILE | A | 79 | 29.273 | −15.927 | −3.845 | 1.00 | 40.48 | A |
| atom | 459 | CG2 | ILE | A | 79 | 29.778 | −16.847 | −4.937 | 1.00 | 44.90 | A |
| atom | 460 | CG1 | ILE | A | 79 | 29.666 | −16.427 | −2.453 | 1.00 | 37.21 | A |
| atom | 461 | CD1 | ILE | A | 79 | 30.545 | −17.632 | −2.466 | 1.00 | 37.28 | A |
| atom | 462 | C   | ILE | A | 79 | 29.115 | −13.846 | −5.215 | 1.00 | 43.40 | A |
| atom | 463 | O   | ILE | A | 79 | 29.698 | −13.684 | −6.277 | 1.00 | 42.18 | A |
| atom | 464 | N   | GLU | A | 80 | 27.864 | −13.441 | −4.994 | 1.00 | 44.19 | A |
| atom | 465 | CA  | GLU | A | 80 | 27.035 | −12.759 | −5.996 | 1.00 | 44.54 | A |
| atom | 466 | CB  | GLU | A | 80 | 25.628 | −12.518 | −5.442 | 1.00 | 44.85 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| | | | | | | | | | | | |
|---|---|---|---|---|---|---|---|---|---|---|---|
| atom | 467 | CG | GLU | A | 80 | 24.668 | −11.886 | −6.439 | 1.00 | 45.12 | A |
| atom | 468 | CD | GLU | A | 80 | 24.475 | −12.745 | −7.664 | 1.00 | 43.40 | A |
| atom | 469 | OE1 | GLU | A | 80 | 25.298 | −12.648 | −8.597 | 1.00 | 43.73 | A |
| atom | 470 | OE2 | GLU | A | 80 | 23.506 | −13.529 | −7.683 | 1.00 | 45.10 | A |
| atom | 471 | C | GLU | A | 80 | 27.613 | −11.404 | −6.368 | 1.00 | 43.67 | A |
| atom | 472 | O | GLU | A | 80 | 28.053 | −10.674 | −5.494 | 1.00 | 46.02 | A |
| atom | 473 | N | GLY | A | 81 | 27.591 | −11.048 | −7.647 | 1.00 | 43.11 | A |
| atom | 474 | CA | GLY | A | 81 | 28.110 | −9.745 | −8.030 | 1.00 | 44.72 | A |
| atom | 475 | C | GLY | A | 81 | 29.525 | −9.816 | −8.563 | 1.00 | 45.52 | A |
| atom | 476 | O | GLY | A | 81 | 29.956 | −8.954 | −9.325 | 1.00 | 47.39 | A |
| atom | 477 | N | ARG | A | 82 | 30.247 | −10.855 | −8.160 | 1.00 | 45.70 | A |
| atom | 478 | CA | ARG | A | 82 | 31.614 | −11.067 | −8.613 | 1.00 | 45.43 | A |
| atom | 479 | CB | ARG | A | 82 | 32.382 | −12.023 | −7.654 | 1.00 | 44.98 | A |
| atom | 480 | CG | ARG | A | 82 | 32.606 | −11.555 | −6.199 | 1.00 | 46.17 | A |
| atom | 481 | CD | ARG | A | 82 | 33.412 | −12.624 | −5.390 | 1.00 | 48.12 | A |
| atom | 482 | NE | ARG | A | 82 | 33.592 | −12.256 | −3.983 | 1.00 | 51.12 | A |
| atom | 483 | CZ | ARG | A | 82 | 34.683 | −11.673 | −3.483 | 1.00 | 54.24 | A |
| atom | 484 | NH1 | ARG | A | 82 | 35.721 | −11.385 | −4.266 | 1.00 | 56.07 | A |
| atom | 485 | NH2 | ARG | A | 82 | 34.740 | −11.365 | −2.194 | 1.00 | 54.61 | A |
| atom | 486 | C | ARG | A | 82 | 31.636 | −11.697 | −10.009 | 1.00 | 45.82 | A |
| atom | 487 | O | ARG | A | 82 | 30.727 | −12.439 | −10.373 | 1.00 | 45.46 | A |
| atom | 488 | N | ASP | A | 83 | 32.724 | −11.431 | −10.733 | 1.00 | 44.64 | A |
| atom | 489 | CA | ASP | A | 83 | 32.989 | −11.974 | −12.054 | 1.00 | 45.15 | A |
| atom | 490 | CB | ASP | A | 83 | 34.345 | −11.440 | −12.539 | 1.00 | 48.61 | A |
| atom | 491 | CG | ASP | A | 83 | 34.748 | −11.969 | −13.897 | 1.00 | 49.45 | A |
| atom | 492 | OD1 | ASP | A | 83 | 35.527 | −12.948 | −13.957 | 1.00 | 50.94 | A |
| atom | 493 | OD2 | ASP | A | 83 | 34.295 | −11.396 | −14.907 | 1.00 | 50.04 | A |
| atom | 494 | C | ASP | A | 83 | 33.030 | −13.479 | −11.873 | 1.00 | 44.55 | A |
| atom | 495 | O | ASP | A | 83 | 33.655 | −13.956 | −10.953 | 1.00 | 43.23 | A |
| atom | 496 | N | ARG | A | 84 | 32.351 | −14.208 | −12.752 | 1.00 | 43.58 | A |
| atom | 497 | CA | ARG | A | 84 | 32.263 | −15.675 | −12.710 | 1.00 | 42.66 | A |
| atom | 498 | CB | ARG | A | 84 | 31.778 | −16.190 | −14.056 | 1.00 | 43.43 | A |
| atom | 499 | CG | ARG | A | 84 | 30.597 | −17.099 | −13.969 | 1.00 | 48.53 | A |
| atom | 500 | CD | ARG | A | 84 | 30.291 | −17.679 | −15.319 | 1.00 | 55.45 | A |
| atom | 501 | NE | ARG | A | 84 | 28.900 | −18.087 | −15.400 | 1.00 | 62.20 | A |
| atom | 502 | CZ | ARG | A | 84 | 28.446 | −18.985 | −16.268 | 1.00 | 66.57 | A |
| atom | 503 | NH1 | ARG | A | 84 | 29.282 | −19.572 | −17.124 | 1.00 | 67.32 | A |
| atom | 504 | NH2 | ARG | A | 84 | 27.155 | −19.293 | −16.293 | 1.00 | 68.30 | A |
| atom | 505 | C | ARG | A | 84 | 33.537 | −16.421 | −12.337 | 1.00 | 40.76 | A |
| atom | 506 | O | ARG | A | 84 | 33.507 | −17.367 | −11.559 | 1.00 | 40.00 | A |
| atom | 507 | N | THR | A | 85 | 34.650 | −15.987 | −12.915 | 1.00 | 39.50 | A |
| atom | 508 | CA | THR | A | 85 | 35.947 | −16.593 | −12.680 | 1.00 | 39.49 | A |
| atom | 509 | CB | THR | A | 85 | 36.968 | −16.060 | −13.754 | 1.00 | 36.42 | A |
| atom | 510 | OG1 | THR | A | 85 | 36.763 | −16.742 | −15.008 | 1.00 | 42.11 | A |
| atom | 511 | CG2 | THR | A | 85 | 38.377 | −16.230 | −13.298 | 1.00 | 38.23 | A |
| atom | 512 | C | THR | A | 85 | 36.421 | −16.350 | −11.242 | 1.00 | 38.76 | A |
| atom | 513 | O | THR | A | 85 | 37.020 | −17.224 | −10.623 | 1.00 | 38.87 | A |
| atom | 514 | N | MET | A | 86 | 36.121 | −15.162 | −10.720 | 1.00 | 41.86 | A |
| atom | 515 | CA | MET | A | 86 | 36.462 | −14.750 | −9.343 | 1.00 | 44.33 | A |
| atom | 516 | CB | MET | A | 86 | 36.161 | −13.242 | −9.170 | 1.00 | 49.50 | A |
| atom | 517 | CG | MET | A | 86 | 36.667 | −12.633 | −7.861 | 1.00 | 57.79 | A |
| atom | 518 | SD | MET | A | 86 | 38.349 | −13.229 | −7.482 | 1.00 | 66.07 | A |
| atom | 519 | CE | MET | A | 86 | 39.057 | −11.836 | −6.502 | 1.00 | 64.38 | A |
| atom | 520 | C | MET | A | 86 | 35.643 | −15.564 | −8.339 | 1.00 | 42.01 | A |
| atom | 521 | O | MET | A | 86 | 36.150 | −16.092 | −7.342 | 1.00 | 40.76 | A |
| atom | 522 | N | ALA | A | 87 | 34.360 | −15.662 | −8.674 | 1.00 | 40.62 | A |
| atom | 523 | CA | ALA | A | 87 | 33.337 | −16.376 | −7.911 | 1.00 | 40.93 | A |
| atom | 524 | CB | ALA | A | 87 | 31.984 | −16.217 | −8.619 | 1.00 | 42.27 | A |
| atom | 525 | C | ALA | A | 87 | 33.651 | −17.849 | −7.671 | 1.00 | 40.41 | A |
| atom | 526 | O | ALA | A | 87 | 33.531 | −18.352 | −6.556 | 1.00 | 39.41 | A |
| atom | 527 | N | TRP | A | 88 | 34.058 | −18.543 | −8.725 | 1.00 | 42.61 | A |
| atom | 528 | CA | TRP | A | 88 | 34.441 | −19.936 | −8.564 | 1.00 | 42.23 | A |
| atom | 529 | CB | TRP | A | 88 | 34.422 | −20.683 | −9.915 | 1.00 | 40.21 | A |
| atom | 530 | CG | TRP | A | 88 | 33.008 | −21.102 | −10.366 | 1.00 | 40.99 | A |
| atom | 531 | CD2 | TRP | A | 88 | 32.153 | −22.081 | −9.739 | 1.00 | 42.30 | A |
| atom | 532 | CE2 | TRP | A | 88 | 30.924 | −22.088 | −10.446 | 1.00 | 40.77 | A |
| atom | 533 | CE3 | TRP | A | 88 | 32.312 | −22.960 | −8.654 | 1.00 | 41.86 | A |
| atom | 534 | CD1 | TRP | A | 88 | 32.270 | −20.573 | −11.404 | 1.00 | 39.66 | A |
| atom | 535 | NE1 | TRP | A | 88 | 31.018 | −21.160 | −11.451 | 1.00 | 40.72 | A |
| atom | 536 | CZ2 | TRP | A | 88 | 29.858 | −22.924 | −10.086 | 1.00 | 41.45 | A |
| atom | 537 | CZ3 | TRP | A | 88 | 31.248 | −23.789 | −8.304 | 1.00 | 39.24 | A |
| atom | 538 | CH2 | TRP | A | 88 | 30.045 | −23.768 | −9.022 | 1.00 | 38.44 | A |
| atom | 539 | C | TRP | A | 88 | 35.795 | −20.024 | −7.846 | 1.00 | 43.60 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| | | | | | | | | | | | |
|---|---|---|---|---|---|---|---|---|---|---|---|
| atom | 540 | O | TRP | A | 88 | 36.021 | −20.933 | −7.065 | 1.00 | 45.98 | A |
| atom | 541 | N | THR | A | 89 | 36.676 | −19.057 | −8.064 | 1.00 | 43.15 | A |
| atom | 542 | CA | THR | A | 89 | 37.956 | −19.060 | −7.347 | 1.00 | 45.86 | A |
| atom | 543 | CB | THR | A | 89 | 38.862 | −17.863 | −7.860 | 1.00 | 47.26 | A |
| atom | 544 | OG1 | THR | A | 89 | 39.275 | −18.123 | −9.216 | 1.00 | 49.62 | A |
| atom | 545 | CG2 | THR | A | 89 | 40.093 | −17.667 | −7.010 | 1.00 | 47.94 | A |
| atom | 546 | C | THR | A | 89 | 37.580 | −19.004 | −5.842 | 1.00 | 44.42 | A |
| atom | 547 | O | THR | A | 89 | 37.792 | −19.980 | −5.141 | 1.00 | 46.98 | A |
| atom | 548 | N | VAL | A | 90 | 36.922 | −17.934 | −5.390 | 1.00 | 43.78 | A |
| atom | 549 | CA | VAL | A | 90 | 36.469 | −17.807 | −3.990 | 1.00 | 40.57 | A |
| atom | 550 | CB | VAL | A | 90 | 35.498 | −16.584 | −3.809 | 1.00 | 41.79 | A |
| atom | 551 | CG1 | VAL | A | 90 | 35.054 | −16.475 | −2.348 | 1.00 | 42.03 | A |
| atom | 552 | CG2 | VAL | A | 90 | 36.140 | −15.319 | −4.285 | 1.00 | 41.27 | A |
| atom | 553 | C | VAL | A | 90 | 35.712 | −19.045 | −3.470 | 1.00 | 39.99 | A |
| atom | 554 | O | VAL | A | 90 | 35.955 | −19.504 | −2.346 | 1.00 | 37.37 | A |
| atom | 555 | N | VAL | A | 91 | 34.780 | −19.559 | −4.278 | 1.00 | 37.69 | A |
| atom | 556 | CA | VAL | A | 91 | 34.016 | −20.745 | −3.875 | 1.00 | 36.06 | A |
| atom | 557 | CB | VAL | A | 91 | 32.857 | −21.136 | −4.893 | 1.00 | 37.21 | A |
| atom | 558 | CG1 | VAL | A | 91 | 32.369 | −22.586 | −4.609 | 1.00 | 33.90 | A |
| atom | 559 | CG2 | VAL | A | 91 | 31.666 | −20.192 | −4.755 | 1.00 | 38.20 | A |
| atom | 560 | C | VAL | A | 91 | 34.887 | −21.992 | −3.709 | 1.00 | 38.63 | A |
| atom | 561 | O | VAL | A | 91 | 34.792 | −22.700 | −2.712 | 1.00 | 37.86 | A |
| atom | 562 | N | ASN | A | 92 | 35.740 | −22.273 | −4.682 | 1.00 | 39.13 | A |
| atom | 563 | CA | ASN | A | 92 | 36.553 | −23.475 | −4.581 | 1.00 | 41.25 | A |
| atom | 564 | CB | ASN | A | 92 | 37.248 | −23.756 | −5.917 | 1.00 | 39.87 | A |
| atom | 565 | CG | ASN | A | 92 | 36.347 | −24.501 | −6.871 | 1.00 | 44.60 | A |
| atom | 566 | OD1 | ASN | A | 92 | 35.875 | −23.951 | −7.858 | 1.00 | 44.24 | A |
| atom | 567 | ND2 | ASN | A | 92 | 36.073 | −25.759 | −6.557 | 1.00 | 50.21 | A |
| atom | 568 | C | ASN | A | 92 | 37.544 | −23.539 | −3.420 | 1.00 | 42.53 | A |
| atom | 569 | O | ASN | A | 92 | 37.778 | −24.619 | −2.851 | 1.00 | 42.46 | A |
| atom | 570 | N | SER | A | 93 | 38.094 | −22.392 | −3.039 | 1.00 | 44.28 | A |
| atom | 571 | CA | SER | A | 93 | 39.035 | −22.361 | −1.937 | 1.00 | 46.79 | A |
| atom | 572 | CB | SER | A | 93 | 40.059 | −21.257 | −2.120 | 1.00 | 45.93 | A |
| atom | 573 | OG | SER | A | 93 | 39.515 | −19.997 | −1.794 | 1.00 | 44.54 | A |
| atom | 574 | C | SER | A | 93 | 38.260 | −22.158 | −0.638 | 1.00 | 50.53 | A |
| atom | 575 | O | SER | A | 93 | 38.837 | −21.831 | 0.386 | 1.00 | 51.99 | A |
| atom | 576 | N | ILE | A | 94 | 36.940 | −22.277 | −0.689 | 1.00 | 51.53 | A |
| atom | 577 | CA | ILE | A | 94 | 36.212 | −22.243 | 0.557 | 1.00 | 51.51 | A |
| atom | 578 | CB | ILE | A | 94 | 34.842 | −21.509 | 0.492 | 1.00 | 50.23 | A |
| atom | 579 | CG2 | ILE | A | 94 | 33.841 | −22.222 | 1.421 | 1.00 | 48.98 | A |
| atom | 580 | CG1 | ILE | A | 94 | 34.999 | −20.072 | 1.024 | 1.00 | 50.40 | A |
| atom | 581 | CD1 | ILE | A | 94 | 34.041 | −19.069 | 0.481 | 1.00 | 47.99 | A |
| atom | 582 | C | ILE | A | 94 | 36.071 | −23.750 | 0.698 | 1.00 | 53.15 | A |
| atom | 583 | O | ILE | A | 94 | 36.571 | −24.307 | 1.658 | 1.00 | 55.61 | A |
| atom | 584 | N | CYS | A | 95 | 35.491 | −24.409 | −0.305 | 1.00 | 52.06 | A |
| atom | 585 | CA | CYS | A | 95 | 35.336 | −25.857 | −0.262 | 1.00 | 53.79 | A |
| atom | 586 | CB | CYS | A | 95 | 34.902 | −26.393 | −1.620 | 1.00 | 53.05 | A |
| atom | 587 | SG | CYS | A | 95 | 33.253 | −25.840 | −1.986 | 1.00 | 54.92 | A |
| atom | 588 | C | CYS | A | 95 | 36.554 | −26.635 | 0.210 | 1.00 | 55.49 | A |
| atom | 589 | O | CYS | A | 95 | 36.478 | −27.853 | 0.455 | 1.00 | 55.86 | A |
| atom | 590 | N | ASN | A | 96 | 37.690 | −25.958 | 0.319 | 1.00 | 55.68 | A |
| atom | 591 | CA | ASN | A | 96 | 38.851 | −26.666 | 0.806 | 1.00 | 55.18 | A |
| atom | 592 | CB | ASN | A | 96 | 39.666 | −27.256 | −0.360 | 1.00 | 56.31 | A |
| atom | 593 | CG | ASN | A | 96 | 40.012 | −26.240 | −1.425 | 1.00 | 57.52 | A |
| atom | 594 | OD1 | ASN | A | 96 | 40.154 | −26.575 | −2.609 | 1.00 | 51.39 | A |
| atom | 595 | ND2 | ASN | A | 96 | 40.193 | −25.000 | −1.009 | 1.00 | 57.95 | A |
| atom | 596 | C | ASN | A | 96 | 39.758 | −26.018 | 1.875 | 1.00 | 56.82 | A |
| atom | 597 | O | ASN | A | 96 | 40.884 | −26.467 | 2.075 | 1.00 | 58.67 | A |
| atom | 598 | N | THR | A | 97 | 39.299 | −24.974 | 2.569 | 1.00 | 54.78 | A |
| atom | 599 | CA | THR | A | 97 | 40.109 | −24.511 | 3.684 | 1.00 | 54.72 | A |
| atom | 600 | CB | THR | A | 97 | 40.333 | −22.978 | 3.840 | 1.00 | 52.31 | A |
| atom | 601 | OG1 | THR | A | 97 | 40.064 | −22.258 | 2.628 | 1.00 | 52.23 | A |
| atom | 602 | CG2 | THR | A | 97 | 41.793 | −22.752 | 4.240 | 1.00 | 53.06 | A |
| atom | 603 | C | THR | A | 97 | 39.163 | −25.009 | 4.762 | 1.00 | 56.04 | A |
| atom | 604 | O | THR | A | 97 | 39.578 | −25.340 | 5.860 | 1.00 | 59.53 | A |
| atom | 605 | N | THR | A | 98 | 37.881 | −25.077 | 4.400 | 1.00 | 55.67 | A |
| atom | 606 | CA | THR | A | 98 | 36.837 | −25.620 | 5.259 | 1.00 | 53.77 | A |
| atom | 607 | CB | THR | A | 98 | 35.453 | −24.945 | 4.994 | 1.00 | 53.83 | A |
| atom | 608 | OG1 | THR | A | 98 | 34.906 | −25.429 | 3.763 | 1.00 | 48.94 | A |
| atom | 609 | CG2 | THR | A | 98 | 35.589 | −23.424 | 4.916 | 1.00 | 51.70 | A |
| atom | 610 | C | THR | A | 98 | 36.862 | −27.052 | 4.722 | 1.00 | 55.29 | A |
| atom | 611 | O | THR | A | 98 | 37.941 | −27.594 | 4.589 | 1.00 | 58.04 | A |
| atom | 612 | N | GLY | A | 99 | 35.727 | −27.671 | 4.405 | 1.00 | 56.19 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor;
atom

| | | | | | | | | | | |
|---|---|---|---|---|---|---|---|---|---|---|
| atom | 613 | CA | GLY | A | 99 | 35.774 | −29.033 | 3.863 | 1.00 | 55.87 | A |
| atom | 614 | C | GLY | A | 99 | 34.465 | −29.392 | 3.172 | 1.00 | 56.58 | A |
| atom | 615 | O | GLY | A | 99 | 34.192 | −30.522 | 2.732 | 1.00 | 55.82 | A |
| atom | 616 | N | VAL | A | 100 | 33.663 | −28.341 | 3.127 | 1.00 | 57.92 | A |
| atom | 617 | CA | VAL | A | 100 | 32.343 | −28.216 | 2.539 | 1.00 | 55.66 | A |
| atom | 618 | CB | VAL | A | 100 | 31.980 | −26.701 | 2.627 | 1.00 | 54.33 | A |
| atom | 619 | CG1 | VAL | A | 100 | 30.527 | −26.447 | 2.322 | 1.00 | 51.01 | A |
| atom | 620 | CG2 | VAL | A | 100 | 32.382 | −26.177 | 3.990 | 1.00 | 51.08 | A |
| atom | 621 | C | VAL | A | 100 | 32.479 | −28.651 | 1.088 | 1.00 | 56.71 | A |
| atom | 622 | O | VAL | A | 100 | 33.513 | −28.400 | 0.488 | 1.00 | 56.97 | A |
| atom | 623 | N | GLU | A | 101 | 31.447 | −29.276 | 0.527 | 1.00 | 56.67 | A |
| atom | 624 | CA | GLU | A | 101 | 31.494 | −29.737 | −0.869 | 1.00 | 58.88 | A |
| atom | 625 | CB | GLU | A | 101 | 30.558 | −30.957 | −1.041 | 1.00 | 60.22 | A |
| atom | 626 | CG | GLU | A | 101 | 29.485 | −31.099 | 0.040 | 1.00 | 62.20 | A |
| atom | 627 | CD | GLU | A | 101 | 29.841 | −32.135 | 1.109 | 1.00 | 66.28 | A |
| atom | 628 | OE1 | GLU | A | 101 | 31.036 | −32.247 | 1.473 | 1.00 | 65.57 | A |
| atom | 629 | OE2 | GLU | A | 101 | 28.922 | −32.829 | 1.608 | 1.00 | 64.13 | A |
| atom | 630 | C | GLU | A | 101 | 31.141 | −28.639 | −1.886 | 1.00 | 58.15 | A |
| atom | 631 | O | GLU | A | 101 | 30.530 | −27.645 | −1.506 | 1.00 | 56.89 | A |
| atom | 632 | N | LYS | A | 102 | 31.495 | −28.831 | −3.155 | 1.00 | 56.94 | A |
| atom | 633 | CA | LYS | A | 102 | 31.213 | −27.835 | −4.151 | 1.00 | 57.30 | A |
| atom | 634 | CB | LYS | A | 102 | 32.011 | −28.135 | −5.476 | 1.00 | 57.07 | A |
| atom | 635 | CG | LYS | A | 102 | 33.221 | −27.199 | −5.709 | 1.00 | 60.89 | A |
| atom | 636 | CD | LYS | A | 102 | 34.200 | −27.637 | −6.848 | 1.00 | 64.34 | A |
| atom | 637 | CE | LYS | A | 102 | 35.371 | −28.568 | −6.402 | 1.00 | 66.72 | A |
| atom | 638 | NZ | LYS | A | 102 | 36.457 | −28.042 | −5.492 | 1.00 | 67.81 | A |
| atom | 639 | C | LYS | A | 102 | 29.728 | −27.688 | −4.445 | 1.00 | 55.88 | A |
| atom | 640 | O | LYS | A | 102 | 29.012 | −28.670 | −4.595 | 1.00 | 55.93 | A |
| atom | 641 | N | PRO | A | 103 | 29.240 | −26.445 | −4.481 | 1.00 | 53.38 | A |
| atom | 642 | CD | PRO | A | 103 | 29.775 | −25.213 | −3.876 | 1.00 | 53.53 | A |
| atom | 643 | CA | PRO | A | 103 | 27.816 | −26.321 | −4.793 | 1.00 | 51.50 | A |
| atom | 644 | CB | PRO | A | 103 | 27.529 | −24.834 | −4.587 | 1.00 | 51.32 | A |
| atom | 645 | CG | PRO | A | 103 | 28.527 | −24.406 | −3.606 | 1.00 | 53.26 | A |
| atom | 646 | C | PRO | A | 103 | 27.855 | −26.623 | −6.256 | 1.00 | 49.35 | A |
| atom | 647 | O | PRO | A | 103 | 28.928 | −26.760 | −6.799 | 1.00 | 50.06 | A |
| atom | 648 | N | LYS | A | 104 | 26.729 | −26.726 | −6.920 | 1.00 | 45.56 | A |
| atom | 649 | CA | LYS | A | 104 | 26.903 | −26.942 | −8.315 | 1.00 | 43.54 | A |
| atom | 650 | CB | LYS | A | 104 | 25.967 | −28.037 | −8.814 | 1.00 | 42.70 | A |
| atom | 651 | CG | LYS | A | 104 | 26.114 | −29.216 | −7.905 | 1.00 | 43.31 | A |
| atom | 652 | CD | LYS | A | 104 | 26.219 | −30.554 | −8.566 | 1.00 | 42.54 | A |
| atom | 653 | CE | LYS | A | 104 | 25.765 | −31.572 | −7.539 | 1.00 | 41.19 | A |
| atom | 654 | NZ | LYS | A | 104 | 24.378 | −31.241 | −7.085 | 1.00 | 44.29 | A |
| atom | 655 | C | LYS | A | 104 | 26.724 | −25.604 | −8.992 | 1.00 | 44.17 | A |
| atom | 656 | O | LYS | A | 104 | 27.351 | −25.338 | −10.012 | 1.00 | 41.08 | A |
| atom | 657 | N | PHE | A | 105 | 25.955 | −24.718 | −8.360 | 1.00 | 44.90 | A |
| atom | 658 | CA | PHE | A | 105 | 25.688 | −23.397 | −8.958 | 1.00 | 44.83 | A |
| atom | 659 | CB | PHE | A | 105 | 24.182 | −23.165 | −9.009 | 1.00 | 45.12 | A |
| atom | 660 | CG | PHE | A | 105 | 23.464 | −24.091 | −9.946 | 1.00 | 48.07 | A |
| atom | 661 | CD1 | PHE | A | 105 | 23.311 | −23.762 | −11.288 | 1.00 | 49.36 | A |
| atom | 662 | CD2 | PHE | A | 105 | 22.994 | −25.331 | −9.506 | 1.00 | 47.08 | A |
| atom | 663 | CE1 | PHE | A | 105 | 22.717 | −24.666 | −12.184 | 1.00 | 46.35 | A |
| atom | 664 | CE2 | PHE | A | 105 | 22.403 | −26.234 | −10.405 | 1.00 | 43.08 | A |
| atom | 665 | CZ | PHE | A | 105 | 22.263 | −25.896 | −11.735 | 1.00 | 44.50 | A |
| atom | 666 | C | PHE | A | 105 | 26.273 | −22.024 | −8.555 | 1.00 | 45.10 | A |
| atom | 667 | O | PHE | A | 105 | 25.914 | −21.032 | −9.176 | 1.00 | 47.09 | A |
| atom | 668 | N | LEU | A | 106 | 27.143 | −21.888 | −7.566 | 1.00 | 44.72 | A |
| atom | 669 | CA | LEU | A | 106 | 27.598 | −20.519 | −7.223 | 1.00 | 41.66 | A |
| atom | 670 | CB | LEU | A | 106 | 27.769 | −19.646 | −8.468 | 1.00 | 38.14 | A |
| atom | 671 | CG | LEU | A | 106 | 29.083 | −19.561 | −9.236 | 1.00 | 43.50 | A |
| atom | 672 | CD1 | LEU | A | 106 | 29.340 | −18.114 | −9.745 | 1.00 | 39.91 | A |
| atom | 673 | CD2 | LEU | A | 106 | 30.194 | −19.983 | −8.294 | 1.00 | 36.99 | A |
| atom | 674 | C | LEU | A | 106 | 26.474 | −19.929 | −6.403 | 1.00 | 38.26 | A |
| atom | 675 | O | LEU | A | 106 | 25.478 | −19.450 | −6.947 | 1.00 | 40.61 | A |
| atom | 676 | N | PRO | A | 107 | 26.602 | −20.010 | −5.078 | 1.00 | 33.25 | A |
| atom | 677 | CD | PRO | A | 107 | 27.691 | −20.707 | −4.380 | 1.00 | 34.70 | A |
| atom | 678 | CA | PRO | A | 107 | 25.607 | −19.490 | −4.145 | 1.00 | 34.72 | A |
| atom | 679 | CB | PRO | A | 107 | 26.044 | −20.056 | −2.795 | 1.00 | 31.70 | A |
| atom | 680 | CG | PRO | A | 107 | 27.033 | −21.130 | −3.112 | 1.00 | 35.82 | A |
| atom | 681 | C | PRO | A | 107 | 25.725 | −17.980 | −4.161 | 1.00 | 35.92 | A |
| atom | 682 | O | PRO | A | 107 | 26.451 | −17.404 | −4.982 | 1.00 | 33.74 | A |
| atom | 683 | N | ASP | A | 108 | 25.043 | −17.329 | −3.234 | 1.00 | 37.90 | A |
| atom | 684 | CA | ASP | A | 108 | 25.138 | −15.884 | −3.177 | 1.00 | 38.18 | A |
| atom | 685 | CB | ASP | A | 108 | 23.776 | −15.275 | −2.894 | 1.00 | 39.07 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| | | | | | | | | | | |
|---|---|---|---|---|---|---|---|---|---|---|
| atom | 686 | CG | ASP | A | 108 | 22.812 | −15.439 | −4.052 | 1.00 | 40.14 | A |
| atom | 687 | OD1 | ASP | A | 108 | 23.251 | −15.265 | −5.204 | 1.00 | 40.70 | A |
| atom | 688 | OD2 | ASP | A | 108 | 21.613 | −15.719 | −3.826 | 1.00 | 40.82 | A |
| atom | 689 | C | ASP | A | 108 | 26.073 | −15.495 | −2.064 | 1.00 | 40.30 | A |
| atom | 690 | O | ASP | A | 108 | 26.755 | −14.477 | −2.128 | 1.00 | 44.69 | A |
| atom | 691 | N | LEU | A | 109 | 26.087 | −16.330 | −1.037 | 1.00 | 40.01 | A |
| atom | 692 | CA | LEU | A | 109 | 26.888 | −16.070 | 0.139 | 1.00 | 38.75 | A |
| atom | 693 | CB | LEU | A | 109 | 26.047 | −15.364 | 1.209 | 1.00 | 35.61 | A |
| atom | 694 | CG | LEU | A | 109 | 25.554 | −13.924 | 1.152 | 1.00 | 34.93 | A |
| atom | 695 | CD1 | LEU | A | 109 | 24.761 | −13.642 | 2.434 | 1.00 | 36.76 | A |
| atom | 696 | CD2 | LEU | A | 109 | 26.717 | −12.976 | 1.062 | 1.00 | 38.70 | A |
| atom | 697 | C | LEU | A | 109 | 27.456 | −17.298 | 0.795 | 1.00 | 39.03 | A |
| atom | 698 | O | LEU | A | 109 | 27.100 | −18.430 | 0.500 | 1.00 | 38.99 | A |
| atom | 699 | N | TYR | A | 110 | 28.331 | −17.035 | 1.739 | 1.00 | 38.65 | A |
| atom | 700 | CA | TYR | A | 110 | 28.902 | −18.103 | 2.481 | 1.00 | 39.37 | A |
| atom | 701 | CB | TYR | A | 110 | 30.202 | −18.558 | 1.852 | 1.00 | 41.64 | A |
| atom | 702 | CG | TYR | A | 110 | 30.828 | −19.646 | 2.667 | 1.00 | 40.06 | A |
| atom | 703 | CD1 | TYR | A | 110 | 30.519 | −20.991 | 2.465 | 1.00 | 40.71 | A |
| atom | 704 | CE1 | TYR | A | 110 | 31.081 | −21.976 | 3.276 | 1.00 | 40.45 | A |
| atom | 705 | CD2 | TYR | A | 110 | 31.694 | −19.314 | 3.688 | 1.00 | 40.36 | A |
| atom | 706 | CE2 | TYR | A | 110 | 32.231 | −20.248 | 4.507 | 1.00 | 42.36 | A |
| atom | 707 | CZ | TYR | A | 110 | 31.938 | −21.581 | 4.305 | 1.00 | 43.06 | A |
| atom | 708 | OH | TYR | A | 110 | 32.517 | −22.476 | 5.166 | 1.00 | 49.40 | A |
| atom | 709 | C | TYR | A | 110 | 29.055 | −17.592 | 3.903 | 1.00 | 41.72 | A |
| atom | 710 | O | TYR | A | 110 | 29.552 | −16.478 | 4.142 | 1.00 | 39.70 | A |
| atom | 711 | N | ASP | A | 111 | 28.541 | −18.410 | 4.825 | 1.00 | 43.66 | A |
| atom | 712 | CA | ASP | A | 111 | 28.511 | −18.149 | 6.263 | 1.00 | 45.72 | A |
| atom | 713 | CB | ASP | A | 111 | 27.109 | −18.533 | 6.770 | 1.00 | 48.49 | A |
| atom | 714 | CG | ASP | A | 111 | 26.789 | −18.025 | 8.186 | 1.00 | 50.22 | A |
| atom | 715 | OD1 | ASP | A | 111 | 25.596 | −18.106 | 8.569 | 1.00 | 52.51 | A |
| atom | 716 | OD2 | ASP | A | 111 | 27.690 | −17.547 | 8.906 | 1.00 | 51.41 | A |
| atom | 717 | C | ASP | A | 111 | 29.537 | −19.067 | 6.902 | 1.00 | 48.87 | A |
| atom | 718 | O | ASP | A | 111 | 29.374 | −20.275 | 6.844 | 1.00 | 49.70 | A |
| atom | 719 | N | TYR | A | 112 | 30.606 | −18.540 | 7.487 | 1.00 | 50.31 | A |
| atom | 720 | CA | TYR | A | 112 | 31.533 | −19.457 | 8.130 | 1.00 | 53.30 | A |
| atom | 721 | CB | TYR | A | 112 | 33.024 | −19.112 | 7.809 | 1.00 | 55.43 | A |
| atom | 722 | CG | TYR | A | 112 | 33.269 | −17.699 | 7.375 | 1.00 | 54.66 | A |
| atom | 723 | CD1 | TYR | A | 112 | 33.744 | −17.367 | 6.090 | 1.00 | 53.25 | A |
| atom | 724 | CE1 | TYR | A | 112 | 33.870 | −16.021 | 5.717 | 1.00 | 57.26 | A |
| atom | 725 | CD2 | TYR | A | 112 | 32.979 | −16.685 | 8.253 | 1.00 | 58.61 | A |
| atom | 726 | CE2 | TYR | A | 112 | 33.113 | −15.398 | 7.913 | 1.00 | 60.19 | A |
| atom | 727 | CZ | TYR | A | 112 | 33.554 | −15.051 | 6.670 | 1.00 | 58.76 | A |
| atom | 728 | OH | TYR | A | 112 | 33.614 | −13.696 | 6.482 | 1.00 | 65.53 | A |
| atom | 729 | C | TYR | A | 112 | 31.189 | −19.587 | 9.643 | 1.00 | 55.08 | A |
| atom | 730 | O | TYR | A | 112 | 31.837 | −20.331 | 10.372 | 1.00 | 56.73 | A |
| atom | 731 | N | LYS | A | 113 | 30.120 | −18.900 | 10.072 | 1.00 | 55.29 | A |
| atom | 732 | CA | LYS | A | 113 | 29.591 | −19.002 | 11.449 | 1.00 | 56.09 | A |
| atom | 733 | CB | LYS | A | 113 | 28.453 | −17.972 | 11.689 | 1.00 | 56.20 | A |
| atom | 734 | CG | LYS | A | 113 | 28.332 | −17.281 | 13.052 | 1.00 | 55.66 | A |
| atom | 735 | CD | LYS | A | 113 | 27.399 | −17.930 | 14.097 | 1.00 | 57.79 | A |
| atom | 736 | CE | LYS | A | 113 | 27.119 | −16.871 | 15.167 | 1.00 | 60.62 | A |
| atom | 737 | NZ | LYS | A | 113 | 26.541 | −17.265 | 16.484 | 1.00 | 63.18 | A |
| atom | 738 | C | LYS | A | 113 | 28.980 | −20.406 | 11.380 | 1.00 | 54.82 | A |
| atom | 739 | O | LYS | A | 113 | 29.456 | −21.342 | 12.032 | 1.00 | 53.82 | A |
| atom | 740 | N | GLU | A | 114 | 27.940 | −20.537 | 10.544 | 1.00 | 54.84 | A |
| atom | 741 | CA | GLU | A | 114 | 27.238 | −21.820 | 10.316 | 1.00 | 55.29 | A |
| atom | 742 | CB | GLU | A | 114 | 25.819 | −21.604 | 9.780 | 1.00 | 54.61 | A |
| atom | 743 | CG | GLU | A | 114 | 24.846 | −20.944 | 10.741 | 1.00 | 55.66 | A |
| atom | 744 | CD | GLU | A | 114 | 24.631 | −21.753 | 12.011 | 1.00 | 57.58 | A |
| atom | 745 | OE1 | GLU | A | 114 | 25.059 | −21.295 | 13.095 | 1.00 | 59.01 | A |
| atom | 746 | OE2 | GLU | A | 114 | 24.029 | −22.849 | 11.932 | 1.00 | 58.27 | A |
| atom | 747 | C | GLU | A | 114 | 28.006 | −22.680 | 9.310 | 1.00 | 55.89 | A |
| atom | 748 | O | GLU | A | 114 | 27.699 | −23.857 | 9.078 | 1.00 | 56.20 | A |
| atom | 749 | N | ASN | A | 115 | 28.978 | −22.040 | 8.674 | 1.00 | 56.98 | A |
| atom | 750 | CA | ASN | A | 115 | 29.869 | −22.711 | 7.740 | 1.00 | 55.57 | A |
| atom | 751 | CB | ASN | A | 115 | 30.788 | −23.582 | 8.630 | 1.00 | 59.40 | A |
| atom | 752 | CG | ASN | A | 115 | 32.039 | −24.088 | 7.937 | 1.00 | 63.31 | A |
| atom | 753 | OD1 | ASN | A | 115 | 32.118 | −25.272 | 7.620 | 1.00 | 66.27 | A |
| atom | 754 | ND2 | ASN | A | 115 | 33.039 | −23.213 | 7.734 | 1.00 | 63.22 | A |
| atom | 755 | C | ASN | A | 115 | 29.105 | −23.488 | 6.615 | 1.00 | 52.00 | A |
| atom | 756 | O | ASN | A | 115 | 29.221 | −24.712 | 6.461 | 1.00 | 49.66 | A |
| atom | 757 | N | ARG | A | 116 | 28.338 | −22.720 | 5.831 | 1.00 | 47.90 | A |
| atom | 758 | CA | ARG | A | 116 | 27.542 | −23.181 | 4.685 | 1.00 | 44.55 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor;
atom

| atom | 759 | CB  | ARG | A | 116 | 26.143 | −23.602 | 5.110  | 1.00 | 43.12 | A |
|------|-----|-----|-----|---|-----|--------|---------|--------|------|-------|---|
| atom | 760 | CG  | ARG | A | 116 | 25.551 | −22.664 | 6.126  | 1.00 | 40.16 | A |
| atom | 761 | CD  | ARG | A | 116 | 24.064 | −22.731 | 6.162  | 1.00 | 37.94 | A |
| atom | 762 | NE  | ARG | A | 116 | 23.547 | −22.889 | 7.515  | 1.00 | 43.66 | A |
| atom | 763 | CZ  | ARG | A | 116 | 22.954 | −21.924 | 8.218  | 1.00 | 46.68 | A |
| atom | 764 | NH1 | ARG | A | 116 | 22.802 | −20.706 | 7.704  | 1.00 | 47.95 | A |
| atom | 765 | NH2 | ARG | A | 116 | 22.470 | −22.186 | 9.427  | 1.00 | 42.71 | A |
| atom | 766 | C   | ARG | A | 116 | 27.361 | −22.043 | 3.687  | 1.00 | 44.58 | A |
| atom | 767 | O   | ARG | A | 116 | 27.576 | −20.871 | 4.010  | 1.00 | 42.41 | A |
| atom | 768 | N   | PHE | A | 117 | 26.940 | −22.405 | 2.482  | 1.00 | 42.87 | A |
| atom | 769 | CA  | PHE | A | 117 | 26.674 | −21.421 | 1.459  | 1.00 | 42.19 | A |
| atom | 770 | CB  | PHE | A | 117 | 26.963 | −21.978 | 0.055  | 1.00 | 40.11 | A |
| atom | 771 | CG  | PHE | A | 117 | 28.418 | −22.115 | −0.248 | 1.00 | 41.38 | A |
| atom | 772 | CD1 | PHE | A | 117 | 29.043 | −23.357 | −0.207 | 1.00 | 39.79 | A |
| atom | 773 | CD2 | PHE | A | 117 | 29.168 | −20.993 | −0.596 | 1.00 | 44.76 | A |
| atom | 774 | CE1 | PHE | A | 117 | 30.397 | −23.484 | −0.513 | 1.00 | 42.83 | A |
| atom | 775 | CE2 | PHE | A | 117 | 30.525 | −21.105 | −0.912 | 1.00 | 44.05 | A |
| atom | 776 | CZ  | PHE | A | 117 | 31.145 | −22.353 | −0.869 | 1.00 | 45.62 | A |
| atom | 777 | C   | PHE | A | 117 | 25.202 | −21.093 | 1.594  | 1.00 | 39.75 | A |
| atom | 778 | O   | PHE | A | 117 | 24.445 | −21.858 | 2.192  | 1.00 | 40.05 | A |
| atom | 779 | N   | ILE | A | 118 | 24.826 | −19.959 | 1.008  | 1.00 | 38.79 | A |
| atom | 780 | CA  | ILE | A | 118 | 23.471 | −19.432 | 0.997  | 1.00 | 38.48 | A |
| atom | 781 | CB  | ILE | A | 118 | 23.339 | −18.285 | 1.990  | 1.00 | 36.93 | A |
| atom | 782 | CG2 | ILE | A | 118 | 21.869 | −17.812 | 2.065  | 1.00 | 31.93 | A |
| atom | 783 | CG1 | ILE | A | 118 | 23.941 | −18.741 | 3.326  | 1.00 | 34.46 | A |
| atom | 784 | CD1 | ILE | A | 118 | 24.154 | −17.649 | 4.344  | 1.00 | 35.07 | A |
| atom | 785 | C   | ILE | A | 118 | 23.114 | −18.859 | −0.361 | 1.00 | 39.11 | A |
| atom | 786 | O   | ILE | A | 118 | 23.917 | −18.138 | −0.972 | 1.00 | 42.06 | A |
| atom | 787 | N   | GLU | A | 119 | 21.897 | −19.184 | −0.794 | 1.00 | 35.76 | A |
| atom | 788 | CA  | GLU | A | 119 | 21.320 | −18.723 | −2.047 | 1.00 | 36.35 | A |
| atom | 789 | CB  | GLU | A | 119 | 20.628 | −19.863 | −2.777 | 1.00 | 36.51 | A |
| atom | 790 | CG  | GLU | A | 119 | 21.532 | −20.778 | −3.537 | 1.00 | 36.17 | A |
| atom | 791 | CD  | GLU | A | 119 | 21.933 | −20.164 | −4.839 | 1.00 | 36.33 | A |
| atom | 792 | OE1 | GLU | A | 119 | 22.692 | −20.799 | −5.606 | 1.00 | 39.05 | A |
| atom | 793 | OE2 | GLU | A | 119 | 21.473 | −19.034 | −5.113 | 1.00 | 35.16 | A |
| atom | 794 | C   | GLU | A | 119 | 20.250 | −17.792 | −1.547 | 1.00 | 38.85 | A |
| atom | 795 | O   | GLU | A | 119 | 19.518 | −18.156 | −0.620 | 1.00 | 37.77 | A |
| atom | 796 | N   | ILE | A | 120 | 20.127 | −16.613 | −2.138 | 1.00 | 37.28 | A |
| atom | 797 | CA  | ILE | A | 120 | 19.094 | −15.718 | −1.674 | 1.00 | 37.51 | A |
| atom | 798 | CB  | ILE | A | 120 | 19.729 | −14.416 | −1.078 | 1.00 | 37.32 | A |
| atom | 799 | CG2 | ILE | A | 120 | 18.677 | −13.324 | −0.946 | 1.00 | 34.95 | A |
| atom | 800 | CG1 | ILE | A | 120 | 20.327 | −14.750 | 0.310  | 1.00 | 39.31 | A |
| atom | 801 | CD1 | ILE | A | 120 | 21.491 | −13.865 | 0.763  | 1.00 | 36.98 | A |
| atom | 802 | C   | ILE | A | 120 | 18.163 | −15.448 | −2.851 | 1.00 | 38.10 | A |
| atom | 803 | O   | ILE | A | 120 | 18.612 | −15.381 | −4.000 | 1.00 | 39.63 | A |
| atom | 804 | N   | GLY | A | 121 | 16.872 | −15.329 | −2.546 | 1.00 | 37.30 | A |
| atom | 805 | CA  | GLY | A | 121 | 15.865 | −15.064 | −3.548 | 1.00 | 37.17 | A |
| atom | 806 | C   | GLY | A | 121 | 15.000 | −13.934 | −3.054 | 1.00 | 36.82 | A |
| atom | 807 | O   | GLY | A | 121 | 14.817 | −13.766 | −1.863 | 1.00 | 36.82 | A |
| atom | 808 | N   | VAL | A | 122 | 14.525 | −13.129 | −3.990 | 1.00 | 33.00 | A |
| atom | 809 | CA  | VAL | A | 122 | 13.610 | −12.033 | −3.699 | 1.00 | 33.82 | A |
| atom | 810 | CB  | VAL | A | 122 | 14.201 | −10.595 | −3.938 | 1.00 | 33.41 | A |
| atom | 811 | CG1 | VAL | A | 122 | 13.108 | −9.539  | −3.739 | 1.00 | 30.21 | A |
| atom | 812 | CG2 | VAL | A | 122 | 15.369 | −10.290 | −2.974 | 1.00 | 29.62 | A |
| atom | 813 | C   | VAL | A | 122 | 12.653 | −12.320 | −4.830 | 1.00 | 35.76 | A |
| atom | 814 | O   | VAL | A | 122 | 13.082 | −12.312 | −5.987 | 1.00 | 33.60 | A |
| atom | 815 | N   | THR | A | 123 | 11.394 | −12.617 | −4.499 | 1.00 | 34.83 | A |
| atom | 816 | CA  | THR | A | 123 | 10.399 | −12.971 | −5.508 | 1.00 | 35.88 | A |
| atom | 817 | CB  | THR | A | 123 | 9.986  | −14.500 | −5.375 | 1.00 | 34.09 | A |
| atom | 818 | OG1 | THR | A | 123 | 8.901  | −14.791 | −6.267 | 1.00 | 37.93 | A |
| atom | 819 | CG2 | THR | A | 123 | 9.566  | −14.841 | −3.941 | 1.00 | 35.45 | A |
| atom | 820 | C   | THR | A | 123 | 9.139  | −12.113 | −5.479 | 1.00 | 34.18 | A |
| atom | 821 | O   | THR | A | 123 | 8.789  | −11.517 | −4.451 | 1.00 | 35.28 | A |
| atom | 822 | N   | ARG | A | 124 | 8.451  | −12.044 | −6.612 | 1.00 | 34.99 | A |
| atom | 823 | CA  | ARG | A | 124 | 7.214  | −11.265 | −6.710 | 1.00 | 37.23 | A |
| atom | 824 | CB  | ARG | A | 124 | 7.232  | −10.411 | −7.984 | 1.00 | 40.43 | A |
| atom | 825 | CG  | ARG | A | 124 | 8.251  | −9.235  | −7.964 | 1.00 | 35.06 | A |
| atom | 826 | CD  | ARG | A | 124 | 8.596  | −8.795  | −9.382 | 1.00 | 38.03 | A |
| atom | 827 | NE  | ARG | A | 124 | 9.791  | −9.501  | −9.838 | 1.00 | 35.43 | A |
| atom | 828 | CZ  | ARG | A | 124 | 10.152 | −9.704  | −11.102| 1.00 | 34.56 | A |
| atom | 829 | NH1 | ARG | A | 124 | 9.414  | −9.256  | −12.111| 1.00 | 37.09 | A |
| atom | 830 | NH2 | ARG | A | 124 | 11.281 | −10.359 | −11.352| 1.00 | 35.12 | A |
| atom | 831 | C   | ARG | A | 124 | 6.093  | −12.312 | −6.747 | 1.00 | 38.56 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor;
atom

| atom | 832 | O | ARG | A | 124 | 4.913 | −11.973 | −6.878 | 1.00 | 36.25 | A |
|---|---|---|---|---|---|---|---|---|---|---|---|
| atom | 833 | N | ARG | A | 125 | 6.485 | −13.583 | −6.595 | 1.00 | 37.65 | A |
| atom | 834 | CA | ARG | A | 125 | 5.526 | −14.682 | −6.588 | 1.00 | 38.69 | A |
| atom | 835 | CB | ARG | A | 125 | 5.971 | −15.773 | −7.585 | 1.00 | 37.70 | A |
| atom | 836 | CG | ARG | A | 125 | 5.630 | −15.378 | −8.999 | 1.00 | 35.26 | A |
| atom | 837 | CD | ARG | A | 125 | 6.558 | −15.889 | −10.069 | 1.00 | 39.07 | A |
| atom | 838 | NE | ARG | A | 125 | 7.772 | −16.516 | −9.570 | 1.00 | 43.48 | A |
| atom | 839 | CZ | ARG | A | 125 | 8.141 | −17.749 | −9.878 | 1.00 | 40.05 | A |
| atom | 840 | NH1 | ARG | A | 125 | 7.379 | −18.474 | −10.672 | 1.00 | 43.26 | A |
| atom | 841 | NH2 | ARG | A | 125 | 9.274 | −18.243 | −9.412 | 1.00 | 36.24 | A |
| atom | 842 | C | ARG | A | 125 | 5.367 | −15.218 | −5.189 | 1.00 | 38.52 | A |
| atom | 843 | O | ARG | A | 125 | 5.839 | −14.602 | −4.250 | 1.00 | 39.10 | A |
| atom | 844 | N | GLU | A | 126 | 4.687 | −16.353 | −5.066 | 1.00 | 40.14 | A |
| atom | 845 | CA | GLU | A | 126 | 4.474 | −16.993 | −3.773 | 1.00 | 42.54 | A |
| atom | 846 | CB | GLU | A | 126 | 3.371 | −18.073 | −3.884 | 1.00 | 47.01 | A |
| atom | 847 | CG | GLU | A | 126 | 1.879 | −17.587 | −3.972 | 1.00 | 55.76 | A |
| atom | 848 | CD | GLU | A | 126 | 1.547 | −16.400 | −3.052 | 1.00 | 61.77 | A |
| atom | 849 | OE1 | GLU | A | 126 | 1.409 | −15.269 | −3.570 | 1.00 | 61.97 | A |
| atom | 850 | OE2 | GLU | A | 126 | 1.410 | −16.571 | −1.815 | 1.00 | 65.58 | A |
| atom | 851 | C | GLU | A | 126 | 5.818 | −17.599 | −3.336 | 1.00 | 41.81 | A |
| atom | 852 | O | GLU | A | 126 | 6.426 | −18.332 | −4.126 | 1.00 | 39.90 | A |
| atom | 853 | N | VAL | A | 127 | 6.297 | −17.293 | −2.111 | 1.00 | 40.69 | A |
| atom | 854 | CA | VAL | A | 127 | 7.632 | −17.811 | −1.702 | 1.00 | 40.14 | A |
| atom | 855 | CB | VAL | A | 127 | 8.269 | −17.174 | −0.334 | 1.00 | 39.75 | A |
| atom | 856 | CG1 | VAL | A | 127 | 8.103 | −15.655 | −0.285 | 1.00 | 41.88 | A |
| atom | 857 | CG2 | VAL | A | 127 | 7.720 | −17.840 | 0.930 | 1.00 | 38.77 | A |
| atom | 858 | C | VAL | A | 127 | 7.828 | −19.322 | −1.612 | 1.00 | 36.68 | A |
| atom | 859 | O | VAL | A | 127 | 8.921 | −19.806 | −1.821 | 1.00 | 35.98 | A |
| atom | 860 | N | HIS | A | 128 | 6.792 | −20.078 | −1.284 | 1.00 | 39.04 | A |
| atom | 861 | CA | HIS | A | 128 | 6.954 | −21.533 | −1.208 | 1.00 | 41.10 | A |
| atom | 862 | CB | HIS | A | 128 | 5.657 | −22.197 | −0.665 | 1.00 | 48.32 | A |
| atom | 863 | CG | HIS | A | 128 | 5.896 | −23.237 | 0.404 | 1.00 | 53.52 | A |
| atom | 864 | CD2 | HIS | A | 128 | 6.767 | −24.271 | 0.473 | 1.00 | 54.99 | A |
| atom | 865 | ND1 | HIS | A | 128 | 5.136 | −23.301 | 1.555 | 1.00 | 56.78 | A |
| atom | 866 | CE1 | HIS | A | 128 | 5.526 | −24.333 | 2.283 | 1.00 | 58.24 | A |
| atom | 867 | NE2 | HIS | A | 128 | 6.513 | −24.939 | 1.653 | 1.00 | 57.75 | A |
| atom | 868 | C | HIS | A | 128 | 7.348 | −22.068 | −2.596 | 1.00 | 39.17 | A |
| atom | 869 | O | HIS | A | 128 | 8.143 | −22.990 | −2.729 | 1.00 | 42.64 | A |
| atom | 870 | N | THR | A | 129 | 6.804 | −21.450 | −3.630 | 1.00 | 37.95 | A |
| atom | 871 | CA | THR | A | 129 | 7.088 | −21.809 | −5.028 | 1.00 | 38.32 | A |
| atom | 872 | CB | THR | A | 129 | 6.207 | −20.942 | −5.947 | 1.00 | 37.58 | A |
| atom | 873 | OG1 | THR | A | 129 | 4.871 | −21.002 | −5.459 | 1.00 | 40.76 | A |
| atom | 874 | CG2 | THR | A | 129 | 6.214 | −21.420 | −7.380 | 1.00 | 36.21 | A |
| atom | 875 | C | THR | A | 129 | 8.549 | −21.562 | −5.354 | 1.00 | 36.95 | A |
| atom | 876 | O | THR | A | 129 | 9.306 | −22.477 | −5.695 | 1.00 | 39.92 | A |
| atom | 877 | N | TYR | A | 130 | 8.927 | −20.306 | −5.187 | 1.00 | 34.37 | A |
| atom | 878 | CA | TYR | A | 130 | 10.269 | −19.867 | −5.434 | 1.00 | 30.60 | A |
| atom | 879 | CB | TYR | A | 130 | 10.333 | −18.377 | −5.151 | 1.00 | 31.20 | A |
| atom | 880 | CG | TYR | A | 130 | 11.530 | −17.730 | −5.745 | 1.00 | 33.62 | A |
| atom | 881 | CD1 | TYR | A | 130 | 11.485 | −17.164 | −7.020 | 1.00 | 35.12 | A |
| atom | 882 | CE1 | TYR | A | 130 | 12.629 | −16.671 | −7.620 | 1.00 | 37.12 | A |
| atom | 883 | CD2 | TYR | A | 130 | 12.738 | −17.769 | −5.081 | 1.00 | 34.62 | A |
| atom | 884 | CE2 | TYR | A | 130 | 13.877 | −17.301 | −5.663 | 1.00 | 35.73 | A |
| atom | 885 | CZ | TYR | A | 130 | 13.825 | −16.744 | −6.932 | 1.00 | 35.96 | A |
| atom | 886 | OH | TYR | A | 130 | 14.972 | −16.285 | −7.525 | 1.00 | 33.23 | A |
| atom | 887 | C | TYR | A | 130 | 11.267 | −20.653 | −4.595 | 1.00 | 31.28 | A |
| atom | 888 | O | TYR | A | 130 | 12.294 | −21.071 | −5.094 | 1.00 | 34.85 | A |
| atom | 889 | N | TYR | A | 131 | 10.940 | −20.887 | −3.331 | 1.00 | 31.94 | A |
| atom | 890 | CA | TYR | A | 131 | 11.820 | −21.659 | −2.454 | 1.00 | 31.28 | A |
| atom | 891 | CB | TYR | A | 131 | 11.223 | −21.776 | −1.029 | 1.00 | 30.28 | A |
| atom | 892 | CG | TYR | A | 131 | 12.129 | −22.520 | −0.054 | 1.00 | 30.07 | A |
| atom | 893 | CD1 | TYR | A | 131 | 13.057 | −21.838 | 0.734 | 1.00 | 29.22 | A |
| atom | 894 | CE1 | TYR | A | 131 | 13.949 | −22.516 | 1.546 | 1.00 | 29.21 | A |
| atom | 895 | CD2 | TYR | A | 131 | 12.102 | −23.914 | 0.023 | 1.00 | 30.39 | A |
| atom | 896 | CE2 | TYR | A | 131 | 12.988 | −24.606 | 0.841 | 1.00 | 31.90 | A |
| atom | 897 | CZ | TYR | A | 131 | 13.900 | −23.912 | 1.602 | 1.00 | 35.09 | A |
| atom | 898 | OH | TYR | A | 131 | 14.740 | −24.663 | 2.399 | 1.00 | 30.92 | A |
| atom | 899 | C | TYR | A | 131 | 12.119 | −23.069 | −2.992 | 1.00 | 34.16 | A |
| atom | 900 | O | TYR | A | 131 | 13.269 | −23.533 | −2.957 | 1.00 | 36.26 | A |
| atom | 901 | N | LEU | A | 132 | 11.072 | −23.743 | −3.484 | 1.00 | 33.40 | A |
| atom | 902 | CA | LEU | A | 132 | 11.187 | −25.115 | −4.031 | 1.00 | 34.56 | A |
| atom | 903 | CB | LEU | A | 132 | 9.806 | −25.766 | −4.192 | 1.00 | 33.83 | A |
| atom | 904 | CG | LEU | A | 132 | 8.995 | −25.957 | −2.901 | 1.00 | 35.27 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| atom | 905 | CD1 | LEU | A | 132 | 7.591 | −26.500 | −3.170 | 1.00 | 36.00 | A |
|---|---|---|---|---|---|---|---|---|---|---|---|
| atom | 906 | CD2 | LEU | A | 132 | 9.773 | −26.880 | −2.004 | 1.00 | 34.65 | A |
| atom | 907 | C | LEU | A | 132 | 11.876 | −25.118 | −5.392 | 1.00 | 34.21 | A |
| atom | 908 | O | LEU | A | 132 | 12.743 | −25.953 | −5.671 | 1.00 | 35.75 | A |
| atom | 909 | N | GLU | A | 133 | 11.455 | −24.191 | −6.242 | 1.00 | 35.35 | A |
| atom | 910 | CA | GLU | A | 133 | 12.030 | −24.081 | −7.562 | 1.00 | 36.07 | A |
| atom | 911 | CB | GLU | A | 133 | 11.568 | −22.783 | −8.223 | 1.00 | 37.15 | A |
| atom | 912 | CG | GLU | A | 133 | 10.190 | −22.875 | −8.794 | 1.00 | 45.06 | A |
| atom | 913 | CD | GLU | A | 133 | 9.806 | −21.632 | −9.588 | 1.00 | 47.69 | A |
| atom | 914 | OE1 | GLU | A | 133 | 8.828 | −21.741 | −10.347 | 1.00 | 47.66 | A |
| atom | 915 | OE2 | GLU | A | 133 | 10.465 | −20.564 | −9.474 | 1.00 | 50.69 | A |
| atom | 916 | C | GLU | A | 133 | 13.518 | −24.053 | −7.347 | 1.00 | 34.84 | A |
| atom | 917 | O | GLU | A | 133 | 14.304 | −24.677 | −8.057 | 1.00 | 33.55 | A |
| atom | 918 | N | LYS | A | 134 | 13.897 | −23.281 | −6.342 | 1.00 | 34.95 | A |
| atom | 919 | CA | LYS | A | 134 | 15.296 | −23.128 | −6.000 | 1.00 | 31.11 | A |
| atom | 920 | CB | LYS | A | 134 | 15.490 | −21.914 | −5.081 | 1.00 | 35.38 | A |
| atom | 921 | CG | LYS | A | 134 | 16.923 | −21.663 | −4.697 | 1.00 | 39.02 | A |
| atom | 922 | CD | LYS | A | 134 | 17.735 | −21.209 | −5.897 | 1.00 | 43.95 | A |
| atom | 923 | CE | LYS | A | 134 | 17.143 | −19.959 | −6.530 | 1.00 | 45.28 | A |
| atom | 924 | NZ | LYS | A | 134 | 17.554 | −18.700 | −5.848 | 1.00 | 49.58 | A |
| atom | 925 | C | LYS | A | 134 | 15.855 | −24.384 | −5.342 | 1.00 | 30.23 | A |
| atom | 926 | O | LYS | A | 134 | 16.933 | −24.842 | −5.717 | 1.00 | 29.89 | A |
| atom | 927 | N | ALA | A | 135 | 15.152 | −24.938 | −4.359 | 1.00 | 29.17 | A |
| atom | 928 | CA | ALA | A | 135 | 15.653 | −26.144 | −3.728 | 1.00 | 34.89 | A |
| atom | 929 | CB | ALA | A | 135 | 14.718 | −26.585 | −2.635 | 1.00 | 33.35 | A |
| atom | 930 | C | ALA | A | 135 | 15.811 | −27.249 | −4.788 | 1.00 | 37.09 | A |
| atom | 931 | O | ALA | A | 135 | 16.720 | −28.064 | −4.697 | 1.00 | 40.46 | A |
| atom | 932 | N | ASN | A | 136 | 14.957 | −27.264 | −5.801 | 1.00 | 35.69 | A |
| atom | 933 | CA | ASN | A | 136 | 15.057 | −28.284 | −6.816 | 1.00 | 37.09 | A |
| atom | 934 | CB | ASN | A | 136 | 13.689 | −28.468 | −7.488 | 1.00 | 36.71 | A |
| atom | 935 | CG | ASN | A | 136 | 12.688 | −29.077 | −6.548 | 1.00 | 36.71 | A |
| atom | 936 | OD1 | ASN | A | 136 | 11.656 | −28.483 | −6.252 | 1.00 | 44.58 | A |
| atom | 937 | ND2 | ASN | A | 136 | 13.001 | −30.264 | −6.052 | 1.00 | 32.42 | A |
| atom | 938 | C | ASN | A | 136 | 16.154 | −28.034 | −7.826 | 1.00 | 38.19 | A |
| atom | 939 | O | ASN | A | 136 | 16.685 | −28.972 | −8.429 | 1.00 | 39.68 | A |
| atom | 940 | N | LYS | A | 137 | 16.501 | −26.770 | −8.017 | 1.00 | 37.96 | A |
| atom | 941 | CA | LYS | A | 137 | 17.558 | −26.462 | −8.951 | 1.00 | 35.93 | A |
| atom | 942 | CB | LYS | A | 137 | 17.616 | −24.967 | −9.275 | 1.00 | 37.08 | A |
| atom | 943 | CG | LYS | A | 137 | 18.803 | −24.647 | −10.182 | 1.00 | 37.10 | A |
| atom | 944 | CD | LYS | A | 137 | 18.758 | −23.264 | −10.762 | 1.00 | 42.03 | A |
| atom | 945 | CE | LYS | A | 137 | 19.888 | −22.445 | −10.211 | 1.00 | 43.50 | A |
| atom | 946 | NZ | LYS | A | 137 | 19.408 | −21.776 | −8.995 | 1.00 | 48.74 | A |
| atom | 947 | C | LYS | A | 137 | 18.898 | −26.886 | −8.383 | 1.00 | 37.04 | A |
| atom | 948 | O | LYS | A | 137 | 19.649 | −27.619 | −9.028 | 1.00 | 38.14 | A |
| atom | 949 | N | ILE | A | 138 | 19.188 | −26.434 | −7.167 | 1.00 | 36.36 | A |
| atom | 950 | CA | ILE | A | 138 | 20.470 | −26.724 | −6.539 | 1.00 | 38.55 | A |
| atom | 951 | CB | ILE | A | 138 | 20.780 | −25.645 | −5.460 | 1.00 | 36.80 | A |
| atom | 952 | CG2 | ILE | A | 138 | 20.795 | −24.255 | −6.113 | 1.00 | 35.37 | A |
| atom | 953 | CG1 | ILE | A | 138 | 19.714 | −25.669 | −4.358 | 1.00 | 38.81 | A |
| atom | 954 | CD1 | ILE | A | 138 | 20.181 | −25.052 | −3.056 | 1.00 | 42.15 | A |
| atom | 955 | C | ILE | A | 138 | 20.784 | −28.128 | −5.986 | 1.00 | 39.85 | A |
| atom | 956 | O | ILE | A | 138 | 21.942 | −28.407 | −5.714 | 1.00 | 39.25 | A |
| atom | 957 | N | LYS | A | 139 | 19.794 | −29.005 | −5.822 | 1.00 | 43.92 | A |
| atom | 958 | CA | LYS | A | 139 | 20.048 | −30.372 | −5.332 | 1.00 | 46.91 | A |
| atom | 959 | CB | LYS | A | 139 | 20.527 | −31.259 | −6.468 | 1.00 | 49.26 | A |
| atom | 960 | CG | LYS | A | 139 | 19.444 | −32.124 | −7.030 | 1.00 | 50.15 | A |
| atom | 961 | CD | LYS | A | 139 | 18.661 | −31.420 | −8.093 | 1.00 | 48.99 | A |
| atom | 962 | CE | LYS | A | 139 | 19.265 | −31.698 | −9.438 | 1.00 | 50.64 | A |
| atom | 963 | NZ | LYS | A | 139 | 18.217 | −31.552 | −10.468 | 1.00 | 54.26 | A |
| atom | 964 | C | LYS | A | 139 | 21.041 | −30.481 | −4.190 | 1.00 | 49.33 | A |
| atom | 965 | O | LYS | A | 139 | 22.111 | −31.081 | −4.293 | 1.00 | 50.85 | A |
| atom | 966 | N | SER | A | 140 | 20.606 | −29.875 | −3.104 | 1.00 | 52.79 | A |
| atom | 967 | CA | SER | A | 140 | 21.293 | −29.677 | −1.838 | 1.00 | 55.20 | A |
| atom | 968 | CB | SER | A | 140 | 20.597 | −28.599 | −1.110 | 1.00 | 60.55 | A |
| atom | 969 | OG | SER | A | 140 | 19.530 | −29.261 | −0.414 | 1.00 | 60.32 | A |
| atom | 970 | C | SER | A | 140 | 21.401 | −30.715 | −0.728 | 1.00 | 56.75 | A |
| atom | 971 | O | SER | A | 140 | 20.803 | −31.795 | −0.681 | 1.00 | 60.15 | A |
| atom | 972 | N | GLU | A | 141 | 22.114 | −30.279 | 0.282 | 1.00 | 54.73 | A |
| atom | 973 | CA | GLU | A | 141 | 22.270 | −31.105 | 1.443 | 1.00 | 55.75 | A |
| atom | 974 | CB | GLU | A | 141 | 23.477 | −32.062 | 1.268 | 1.00 | 59.79 | A |
| atom | 975 | CG | GLU | A | 141 | 23.889 | −32.376 | −0.198 | 1.00 | 63.01 | A |
| atom | 976 | CD | GLU | A | 141 | 25.427 | −32.432 | −0.421 | 1.00 | 66.92 | A |
| atom | 977 | OE1 | GLU | A | 141 | 26.129 | −33.236 | 0.239 | 1.00 | 68.56 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| atom | 978 | OE2 | GLU | A | 141 | 25.956 | −31.681 | −1.277 | 1.00 | 67.21 | A |
|---|---|---|---|---|---|---|---|---|---|---|---|
| atom | 979 | C | GLU | A | 141 | 22.590 | −30.068 | 2.471 | 1.00 | 54.83 | A |
| atom | 980 | O | GLU | A | 141 | 21.943 | −29.935 | 3.515 | 1.00 | 51.66 | A |
| atom | 981 | N | LYS | A | 142 | 23.532 | −29.244 | 2.054 | 1.00 | 52.85 | A |
| atom | 982 | CA | LYS | A | 142 | 24.096 | −28.255 | 2.922 | 1.00 | 53.68 | A |
| atom | 983 | CB | LYS | A | 142 | 25.571 | −28.624 | 2.996 | 1.00 | 52.79 | A |
| atom | 984 | CG | LYS | A | 142 | 25.662 | −30.095 | 3.494 | 1.00 | 55.47 | A |
| atom | 985 | CD | LYS | A | 142 | 26.895 | −30.882 | 3.069 | 1.00 | 54.74 | A |
| atom | 986 | CE | LYS | A | 142 | 28.080 | −30.632 | 3.978 | 1.00 | 53.87 | A |
| atom | 987 | NZ | LYS | A | 142 | 28.873 | −29.477 | 3.497 | 1.00 | 54.33 | A |
| atom | 988 | C | LYS | A | 142 | 23.888 | −26.764 | 2.704 | 1.00 | 51.28 | A |
| atom | 989 | O | LYS | A | 142 | 24.042 | −25.967 | 3.641 | 1.00 | 54.13 | A |
| atom | 990 | N | THR | A | 143 | 23.530 | −26.375 | 1.488 | 1.00 | 48.14 | A |
| atom | 991 | CA | THR | A | 143 | 23.320 | −24.958 | 1.187 | 1.00 | 43.32 | A |
| atom | 992 | CB | THR | A | 143 | 23.413 | −24.748 | −0.311 | 1.00 | 43.87 | A |
| atom | 993 | OG1 | THR | A | 143 | 22.397 | −25.528 | −0.941 | 1.00 | 50.19 | A |
| atom | 994 | CG2 | THR | A | 143 | 24.768 | −25.233 | −0.803 | 1.00 | 37.06 | A |
| atom | 995 | C | THR | A | 143 | 21.975 | −24.502 | 1.728 | 1.00 | 37.30 | A |
| atom | 996 | O | THR | A | 143 | 20.967 | −25.149 | 1.495 | 1.00 | 32.21 | A |
| atom | 997 | N | HIS | A | 144 | 21.988 | −23.378 | 2.440 | 1.00 | 32.95 | A |
| atom | 998 | CA | HIS | A | 144 | 20.795 | −22.817 | 3.049 | 1.00 | 29.49 | A |
| atom | 999 | CB | HIS | A | 144 | 21.207 | −21.900 | 4.197 | 1.00 | 31.84 | A |
| atom | 1000 | CG | HIS | A | 144 | 20.315 | −22.004 | 5.389 | 1.00 | 36.42 | A |
| atom | 1001 | CD2 | HIS | A | 144 | 19.538 | −21.080 | 5.999 | 1.00 | 34.47 | A |
| atom | 1002 | ND1 | HIS | A | 144 | 20.098 | −23.193 | 6.051 | 1.00 | 38.07 | A |
| atom | 1003 | CE1 | HIS | A | 144 | 19.213 | −23.000 | 7.014 | 1.00 | 40.13 | A |
| atom | 1004 | NE2 | HIS | A | 144 | 18.856 | −21.729 | 7.002 | 1.00 | 41.00 | A |
| atom | 1005 | C | HIS | A | 144 | 20.007 | −22.032 | 1.994 | 1.00 | 30.28 | A |
| atom | 1006 | O | HIS | A | 144 | 20.553 | −21.598 | 0.978 | 1.00 | 29.35 | A |
| atom | 1007 | N | ILE | A | 145 | 18.716 | −21.865 | 2.200 | 1.00 | 28.99 | A |
| atom | 1008 | CA | ILE | A | 145 | 17.964 | −21.103 | 1.227 | 1.00 | 31.65 | A |
| atom | 1009 | CB | ILE | A | 145 | 17.007 | −21.979 | 0.374 | 1.00 | 32.45 | A |
| atom | 1010 | CG2 | ILE | A | 145 | 16.054 | −21.064 | −0.344 | 1.00 | 32.11 | A |
| atom | 1011 | CG1 | ILE | A | 145 | 17.776 | −22.830 | −0.654 | 1.00 | 32.64 | A |
| atom | 1012 | CD1 | ILE | A | 145 | 17.012 | −24.055 | −1.210 | 1.00 | 30.51 | A |
| atom | 1013 | C | ILE | A | 145 | 17.147 | −20.105 | 2.003 | 1.00 | 30.21 | A |
| atom | 1014 | O | ILE | A | 145 | 16.550 | −20.447 | 3.011 | 1.00 | 32.21 | A |
| atom | 1015 | N | HIS | A | 146 | 17.128 | −18.871 | 1.530 | 1.00 | 32.11 | A |
| atom | 1016 | CA | HIS | A | 146 | 16.391 | −17.855 | 2.215 | 1.00 | 32.60 | A |
| atom | 1017 | CB | HIS | A | 146 | 17.329 | −17.142 | 3.184 | 1.00 | 33.23 | A |
| atom | 1018 | CG | HIS | A | 146 | 16.600 | −16.325 | 4.186 | 1.00 | 34.21 | A |
| atom | 1019 | CD2 | HIS | A | 146 | 15.421 | −15.653 | 4.113 | 1.00 | 32.02 | A |
| atom | 1020 | ND1 | HIS | A | 146 | 17.048 | −16.161 | 5.476 | 1.00 | 35.12 | A |
| atom | 1021 | CE1 | HIS | A | 146 | 16.181 | −15.438 | 6.157 | 1.00 | 32.54 | A |
| atom | 1022 | NE2 | HIS | A | 146 | 15.183 | −15.118 | 5.350 | 1.00 | 33.53 | A |
| atom | 1023 | C | HIS | A | 146 | 15.745 | −16.890 | 1.199 | 1.00 | 30.33 | A |
| atom | 1024 | O | HIS | A | 146 | 16.430 | −16.174 | 0.476 | 1.00 | 30.09 | A |
| atom | 1025 | N | ILE | A | 147 | 14.416 | −16.886 | 1.145 | 1.00 | 31.29 | A |
| atom | 1026 | CA | ILE | A | 147 | 13.697 | −16.045 | 0.207 | 1.00 | 31.65 | A |
| atom | 1027 | CB | ILE | A | 147 | 12.805 | −16.933 | −0.753 | 1.00 | 33.25 | A |
| atom | 1028 | CG2 | ILE | A | 147 | 11.833 | −16.092 | −1.608 | 1.00 | 32.35 | A |
| atom | 1029 | CG1 | ILE | A | 147 | 13.746 | −17.774 | −1.652 | 1.00 | 32.01 | A |
| atom | 1030 | CD1 | ILE | A | 147 | 13.564 | −19.300 | −1.437 | 1.00 | 37.64 | A |
| atom | 1031 | C | ILE | A | 147 | 12.911 | −14.977 | 0.936 | 1.00 | 32.33 | A |
| atom | 1032 | O | ILE | A | 147 | 12.326 | −15.192 | 2.012 | 1.00 | 34.92 | A |
| atom | 1033 | N | PHE | A | 148 | 12.971 | −13.796 | 0.344 | 1.00 | 32.27 | A |
| atom | 1034 | CA | PHE | A | 148 | 12.293 | −12.612 | 0.842 | 1.00 | 34.34 | A |
| atom | 1035 | CB | PHE | A | 148 | 13.275 | −11.454 | 0.955 | 1.00 | 31.26 | A |
| atom | 1036 | CG | PHE | A | 148 | 14.182 | −11.564 | 2.113 | 1.00 | 31.50 | A |
| atom | 1037 | CD1 | PHE | A | 148 | 15.494 | −12.028 | 1.973 | 1.00 | 31.86 | A |
| atom | 1038 | CD2 | PHE | A | 148 | 13.711 | −11.248 | 3.367 | 1.00 | 31.72 | A |
| atom | 1039 | CE1 | PHE | A | 148 | 16.322 | −12.178 | 3.098 | 1.00 | 33.44 | A |
| atom | 1040 | CE2 | PHE | A | 148 | 14.509 | −11.394 | 4.491 | 1.00 | 33.54 | A |
| atom | 1041 | CZ | PHE | A | 148 | 15.813 | −11.855 | 4.355 | 1.00 | 32.39 | A |
| atom | 1042 | C | PHE | A | 148 | 11.322 | −12.255 | −0.249 | 1.00 | 35.27 | A |
| atom | 1043 | O | PHE | A | 148 | 11.538 | −12.587 | −1.412 | 1.00 | 36.54 | A |
| atom | 1044 | N | SER | A | 149 | 10.251 | −11.574 | 0.098 | 1.00 | 37.34 | A |
| atom | 1045 | CA | SER | A | 149 | 9.374 | −11.155 | −0.964 | 1.00 | 39.57 | A |
| atom | 1046 | CB | SER | A | 149 | 8.029 | −11.915 | −0.927 | 1.00 | 37.31 | A |
| atom | 1047 | OG | SER | A | 149 | 7.225 | −11.569 | 0.184 | 1.00 | 40.03 | A |
| atom | 1048 | C | SER | A | 149 | 9.203 | −9.661 | −0.831 | 1.00 | 40.29 | A |
| atom | 1049 | O | SER | A | 149 | 9.898 | −9.013 | −0.056 | 1.00 | 40.76 | A |
| atom | 1050 | N | PHE | A | 150 | 8.290 | −9.113 | −1.611 | 1.00 | 39.73 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| atom | 1051 | CA | PHE | A | 150 | 8.039 | −7.700 | −1.536 | 1.00 | 39.89 | A |
|---|---|---|---|---|---|---|---|---|---|---|---|
| atom | 1052 | CB | PHE | A | 150 | 7.684 | −7.121 | −2.916 | 1.00 | 38.54 | A |
| atom | 1053 | CG | PHE | A | 150 | 8.884 | −6.726 | −3.720 | 1.00 | 38.70 | A |
| atom | 1054 | CD1 | PHE | A | 150 | 9.452 | −7.615 | −4.612 | 1.00 | 36.91 | A |
| atom | 1055 | CD2 | PHE | A | 150 | 9.486 | −5.490 | −3.540 | 1.00 | 39.59 | A |
| atom | 1056 | CE1 | PHE | A | 150 | 10.599 | −7.290 | −5.317 | 1.00 | 31.97 | A |
| atom | 1057 | CE2 | PHE | A | 150 | 10.629 | −5.153 | −4.229 | 1.00 | 39.19 | A |
| atom | 1058 | CZ | PHE | A | 150 | 11.193 | −6.048 | −5.118 | 1.00 | 40.87 | A |
| atom | 1059 | C | PHE | A | 150 | 6.898 | −7.503 | −0.561 | 1.00 | 42.11 | A |
| atom | 1060 | O | PHE | A | 150 | 6.594 | −6.368 | −0.185 | 1.00 | 44.70 | A |
| atom | 1061 | N | THR | A | 151 | 6.260 | −8.605 | −0.162 | 1.00 | 42.86 | A |
| atom | 1062 | CA | THR | A | 151 | 5.125 | −8.539 | 0.760 | 1.00 | 44.07 | A |
| atom | 1063 | CB | THR | A | 151 | 4.074 | −9.632 | 0.488 | 1.00 | 46.05 | A |
| atom | 1064 | OG1 | THR | A | 151 | 4.525 | −10.860 | 1.077 | 1.00 | 44.09 | A |
| atom | 1065 | CG2 | THR | A | 151 | 3.847 | −9.849 | −0.994 | 1.00 | 41.69 | A |
| atom | 1066 | C | THR | A | 151 | 5.446 | −8.722 | 2.256 | 1.00 | 44.86 | A |
| atom | 1067 | O | THR | A | 151 | 4.556 | −8.545 | 3.095 | 1.00 | 46.27 | A |
| atom | 1068 | N | GLY | A | 152 | 6.677 | −9.117 | 2.589 | 1.00 | 43.05 | A |
| atom | 1069 | CA | GLY | A | 152 | 7.044 | −9.337 | 3.989 | 1.00 | 40.46 | A |
| atom | 1070 | C | GLY | A | 152 | 7.266 | −10.801 | 4.377 | 1.00 | 40.98 | A |
| atom | 1071 | O | GLY | A | 152 | 7.975 | −11.110 | 5.329 | 1.00 | 40.02 | A |
| atom | 1072 | N | GLU | A | 153 | 6.634 | −11.702 | 3.628 | 1.00 | 41.20 | A |
| atom | 1073 | CA | GLU | A | 153 | 6.733 | −13.152 | 3.819 | 1.00 | 41.06 | A |
| atom | 1074 | CB | GLU | A | 153 | 5.662 | −13.851 | 2.916 | 1.00 | 42.73 | A |
| atom | 1075 | CG | GLU | A | 153 | 5.596 | −15.398 | 2.897 | 1.00 | 49.73 | A |
| atom | 1076 | CD | GLU | A | 153 | 4.321 | −15.947 | 2.199 | 1.00 | 53.42 | A |
| atom | 1077 | OE1 | GLU | A | 153 | 3.235 | −15.928 | 2.822 | 1.00 | 53.34 | A |
| atom | 1078 | OE2 | GLU | A | 153 | 4.396 | −16.381 | 1.024 | 1.00 | 53.84 | A |
| atom | 1079 | C | GLU | A | 153 | 8.162 | −13.615 | 3.464 | 1.00 | 40.34 | A |
| atom | 1080 | O | GLU | A | 153 | 8.727 | −13.183 | 2.454 | 1.00 | 40.91 | A |
| atom | 1081 | N | GLU | A | 154 | 8.754 | −14.454 | 4.316 | 1.00 | 38.52 | A |
| atom | 1082 | CA | GLU | A | 154 | 10.087 | −15.021 | 4.056 | 1.00 | 38.65 | A |
| atom | 1083 | CB | GLU | A | 154 | 11.161 | −14.414 | 4.997 | 1.00 | 38.03 | A |
| atom | 1084 | CG | GLU | A | 154 | 10.812 | −14.493 | 6.483 | 1.00 | 40.42 | A |
| atom | 1085 | CD | GLU | A | 154 | 11.724 | −13.639 | 7.399 | 1.00 | 46.82 | A |
| atom | 1086 | OE1 | GLU | A | 154 | 11.247 | −13.272 | 8.498 | 1.00 | 49.40 | A |
| atom | 1087 | OE2 | GLU | A | 154 | 12.895 | −13.349 | 7.036 | 1.00 | 41.06 | A |
| atom | 1088 | C | GLU | A | 154 | 9.951 | −16.515 | 4.317 | 1.00 | 38.83 | A |
| atom | 1089 | O | GLU | A | 154 | 8.947 | −16.936 | 4.878 | 1.00 | 40.73 | A |
| atom | 1090 | N | MET | A | 155 | 10.965 | −17.284 | 3.921 | 1.00 | 37.18 | A |
| atom | 1091 | CA | MET | A | 155 | 11.032 | −18.726 | 4.113 | 1.00 | 36.04 | A |
| atom | 1092 | CB | MET | A | 155 | 10.267 | −19.483 | 3.025 | 1.00 | 39.30 | A |
| atom | 1093 | CG | MET | A | 155 | 10.196 | −20.994 | 3.256 | 1.00 | 38.48 | A |
| atom | 1094 | SD | MET | A | 155 | 9.133 | −21.658 | 1.959 | 1.00 | 46.96 | A |
| atom | 1095 | CE | MET | A | 155 | 7.927 | −22.561 | 2.850 | 1.00 | 45.52 | A |
| atom | 1096 | C | MET | A | 155 | 12.506 | −19.039 | 4.006 | 1.00 | 34.02 | A |
| atom | 1097 | O | MET | A | 155 | 13.144 | −18.708 | 3.023 | 1.00 | 33.65 | A |
| atom | 1098 | N | ALA | A | 156 | 13.035 | −19.673 | 5.038 | 1.00 | 35.17 | A |
| atom | 1099 | CA | ALA | A | 156 | 14.428 | −20.063 | 5.098 | 1.00 | 33.80 | A |
| atom | 1100 | CB | ALA | A | 156 | 15.163 | −19.173 | 6.088 | 1.00 | 30.33 | A |
| atom | 1101 | C | ALA | A | 156 | 14.520 | −21.515 | 5.536 | 1.00 | 33.74 | A |
| atom | 1102 | O | ALA | A | 156 | 13.726 | −21.968 | 6.334 | 1.00 | 34.63 | A |
| atom | 1103 | N | THR | A | 157 | 15.490 | −22.231 | 4.996 | 1.00 | 35.03 | A |
| atom | 1104 | CA | THR | A | 157 | 15.696 | −23.631 | 5.318 | 1.00 | 38.19 | A |
| atom | 1105 | CB | THR | A | 157 | 17.050 | −24.124 | 4.722 | 1.00 | 38.78 | A |
| atom | 1106 | OG1 | THR | A | 157 | 17.081 | −23.841 | 3.311 | 1.00 | 37.14 | A |
| atom | 1107 | CG2 | THR | A | 157 | 17.245 | −25.620 | 5.002 | 1.00 | 37.68 | A |
| atom | 1108 | C | THR | A | 157 | 15.667 | −23.958 | 6.819 | 1.00 | 39.97 | A |
| atom | 1109 | O | THR | A | 157 | 16.353 | −23.307 | 7.618 | 1.00 | 42.20 | A |
| atom | 1110 | N | LYS | A | 158 | 14.851 | −24.969 | 7.162 | 1.00 | 40.33 | A |
| atom | 1111 | CA | LYS | A | 158 | 14.640 | −25.518 | 8.524 | 1.00 | 39.35 | A |
| atom | 1112 | CB | LYS | A | 158 | 15.925 | −26.236 | 9.007 | 1.00 | 38.81 | A |
| atom | 1113 | CG | LYS | A | 158 | 16.525 | −27.227 | 7.985 | 1.00 | 40.96 | A |
| atom | 1114 | CD | LYS | A | 158 | 17.319 | −28.414 | 8.631 | 1.00 | 44.46 | A |
| atom | 1115 | CE | LYS | A | 158 | 18.852 | −28.325 | 8.494 | 1.00 | 46.71 | A |
| atom | 1116 | NZ | LYS | A | 158 | 19.488 | −29.675 | 8.357 | 1.00 | 52.72 | A |
| atom | 1117 | C | LYS | A | 158 | 14.157 | −24.539 | 9.598 | 1.00 | 41.30 | A |
| atom | 1118 | O | LYS | A | 158 | 14.186 | −24.843 | 10.802 | 1.00 | 43.06 | A |
| atom | 1119 | N | ALA | A | 159 | 13.679 | −23.396 | 9.101 | 1.00 | 40.51 | A |
| atom | 1120 | CA | ALA | A | 159 | 13.191 | −22.227 | 9.837 | 1.00 | 39.68 | A |
| atom | 1121 | CB | ALA | A | 159 | 12.063 | −22.568 | 10.842 | 1.00 | 39.56 | A |
| atom | 1122 | C | ALA | A | 159 | 14.373 | −21.576 | 10.534 | 1.00 | 42.06 | A |
| atom | 1123 | O | ALA | A | 159 | 14.208 | −20.808 | 11.476 | 1.00 | 41.19 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| atom | 1124 | N   | ASP | A | 160 | 15.579 | −21.906 | 10.079 | 1.00 | 40.07 | A |
|------|------|-----|-----|---|-----|--------|---------|--------|------|-------|---|
| atom | 1125 | CA  | ASP | A | 160 | 16.759 | −21.289 | 10.652 | 1.00 | 37.14 | A |
| atom | 1126 | CB  | ASP | A | 160 | 17.979 | −22.216 | 10.507 | 1.00 | 37.65 | A |
| atom | 1127 | CG  | ASP | A | 160 | 19.289 | −21.576 | 10.984 | 1.00 | 37.80 | A |
| atom | 1128 | OD1 | ASP | A | 160 | 20.315 | −22.285 | 10.990 | 1.00 | 36.92 | A |
| atom | 1129 | OD2 | ASP | A | 160 | 19.302 | −20.383 | 11.361 | 1.00 | 36.44 | A |
| atom | 1130 | C   | ASP | A | 160 | 16.898 | −20.031 | 9.809  | 1.00 | 34.50 | A |
| atom | 1131 | O   | ASP | A | 160 | 17.428 | −20.039 | 8.709  | 1.00 | 35.45 | A |
| atom | 1132 | N   | TYR | A | 161 | 16.381 | −18.941 | 10.343 | 1.00 | 35.75 | A |
| atom | 1133 | CA  | TYR | A | 161 | 16.399 | −17.672 | 9.645  | 1.00 | 35.81 | A |
| atom | 1134 | CB  | TYR | A | 161 | 15.222 | −16.829 | 10.138 | 1.00 | 36.43 | A |
| atom | 1135 | CG  | TYR | A | 161 | 13.912 | −17.387 | 9.582  | 1.00 | 38.98 | A |
| atom | 1136 | CD1 | TYR | A | 161 | 13.272 | −18.467 | 10.189 | 1.00 | 39.18 | A |
| atom | 1137 | CE1 | TYR | A | 161 | 12.199 | −19.112 | 9.573  | 1.00 | 40.53 | A |
| atom | 1138 | CD2 | TYR | A | 161 | 13.422 | −16.950 | 8.349  | 1.00 | 38.32 | A |
| atom | 1139 | CE2 | TYR | A | 161 | 12.348 | −17.580 | 7.725  | 1.00 | 43.06 | A |
| atom | 1140 | CZ  | TYR | A | 161 | 11.746 | −18.669 | 8.345  | 1.00 | 41.69 | A |
| atom | 1141 | OH  | TYR | A | 161 | 10.719 | −19.330 | 7.719  | 1.00 | 43.09 | A |
| atom | 1142 | C   | TYR | A | 161 | 17.718 | −16.911 | 9.656  | 1.00 | 35.75 | A |
| atom | 1143 | O   | TYR | A | 161 | 17.812 | −15.795 | 9.135  | 1.00 | 36.99 | A |
| atom | 1144 | N   | THR | A | 162 | 18.737 | −17.513 | 10.259 | 1.00 | 34.74 | A |
| atom | 1145 | CA  | THR | A | 162 | 20.084 | −16.942 | 10.242 | 1.00 | 36.95 | A |
| atom | 1146 | CB  | THR | A | 162 | 20.648 | −16.977 | 8.794  | 1.00 | 38.13 | A |
| atom | 1147 | OG1 | THR | A | 162 | 20.577 | −18.320 | 8.290  | 1.00 | 38.14 | A |
| atom | 1148 | CG2 | THR | A | 162 | 22.079 | −16.506 | 8.770  | 1.00 | 35.32 | A |
| atom | 1149 | C   | THR | A | 162 | 20.377 | −15.553 | 10.806 | 1.00 | 37.26 | A |
| atom | 1150 | O   | THR | A | 162 | 21.253 | −15.407 | 11.651 | 1.00 | 39.21 | A |
| atom | 1151 | N   | LEU | A | 163 | 19.681 | −14.534 | 10.322 | 1.00 | 36.85 | A |
| atom | 1152 | CA  | LEU | A | 163 | 19.887 | −13.159 | 10.783 | 1.00 | 38.57 | A |
| atom | 1153 | CB  | LEU | A | 163 | 19.614 | −12.191 | 9.630  | 1.00 | 37.58 | A |
| atom | 1154 | CG  | LEU | A | 163 | 20.561 | −12.306 | 8.435  | 1.00 | 38.70 | A |
| atom | 1155 | CD1 | LEU | A | 163 | 20.251 | −11.180 | 7.469  | 1.00 | 34.90 | A |
| atom | 1156 | CD2 | LEU | A | 163 | 22.010 | −12.225 | 8.918  | 1.00 | 28.99 | A |
| atom | 1157 | C   | LEU | A | 163 | 18.947 | −12.835 | 11.923 | 1.00 | 40.92 | A |
| atom | 1158 | O   | LEU | A | 163 | 17.986 | −13.576 | 12.139 | 1.00 | 38.21 | A |
| atom | 1159 | N   | ASP | A | 164 | 19.142 | −11.740 | 12.651 | 1.00 | 42.96 | A |
| atom | 1160 | CA  | ASP | A | 164 | 18.149 | −11.600 | 13.693 | 1.00 | 46.57 | A |
| atom | 1161 | CB  | ASP | A | 164 | 18.766 | −11.125 | 15.028 | 1.00 | 49.46 | A |
| atom | 1162 | CG  | ASP | A | 164 | 18.961 | −9.623  | 15.122 | 1.00 | 54.46 | A |
| atom | 1163 | OD1 | ASP | A | 164 | 19.617 | −9.008  | 14.239 | 1.00 | 50.17 | A |
| atom | 1164 | OD2 | ASP | A | 164 | 18.444 | −9.051  | 16.111 | 1.00 | 55.96 | A |
| atom | 1165 | C   | ASP | A | 164 | 16.919 | −10.842 | 13.234 | 1.00 | 47.50 | A |
| atom | 1166 | O   | ASP | A | 164 | 16.843 | −10.436 | 12.072 | 1.00 | 49.49 | A |
| atom | 1167 | N   | GLU | A | 165 | 15.924 | −10.691 | 14.094 | 1.00 | 47.07 | A |
| atom | 1168 | CA  | GLU | A | 165 | 14.710 | −10.044 | 13.625 | 1.00 | 48.29 | A |
| atom | 1169 | CB  | GLU | A | 165 | 13.667 | −9.989  | 14.755 | 1.00 | 48.51 | A |
| atom | 1170 | CG  | GLU | A | 165 | 13.298 | −11.398 | 15.296 | 1.00 | 48.39 | A |
| atom | 1171 | CD  | GLU | A | 165 | 12.493 | −12.279 | 14.331 | 1.00 | 44.35 | A |
| atom | 1172 | OE1 | GLU | A | 165 | 12.658 | −13.520 | 14.392 | 1.00 | 47.15 | A |
| atom | 1173 | OE2 | GLU | A | 165 | 11.699 | −11.733 | 13.543 | 1.00 | 45.32 | A |
| atom | 1174 | C   | GLU | A | 165 | 14.975 | −8.678  | 13.005 | 1.00 | 49.83 | A |
| atom | 1175 | O   | GLU | A | 165 | 14.554 | −8.422  | 11.880 | 1.00 | 52.91 | A |
| atom | 1176 | N   | GLU | A | 166 | 15.712 | −7.833  | 13.719 | 1.00 | 51.49 | A |
| atom | 1177 | CA  | GLU | A | 166 | 16.056 | −6.481  | 13.264 | 1.00 | 52.53 | A |
| atom | 1178 | CB  | GLU | A | 166 | 16.910 | −5.776  | 14.332 | 1.00 | 58.32 | A |
| atom | 1179 | CG  | GLU | A | 166 | 17.552 | −6.766  | 15.329 | 1.00 | 68.45 | A |
| atom | 1180 | CD  | GLU | A | 166 | 18.695 | −6.182  | 16.171 | 1.00 | 72.20 | A |
| atom | 1181 | OE1 | GLU | A | 166 | 19.324 | −6.961  | 16.920 | 1.00 | 75.71 | A |
| atom | 1182 | OE2 | GLU | A | 166 | 18.974 | −4.959  | 16.109 | 1.00 | 75.05 | A |
| atom | 1183 | C   | GLU | A | 166 | 16.775 | −6.418  | 11.918 | 1.00 | 50.96 | A |
| atom | 1184 | O   | GLU | A | 166 | 16.453 | −5.598  | 11.062 | 1.00 | 52.34 | A |
| atom | 1185 | N   | SER | A | 167 | 17.745 | −7.287  | 11.704 | 1.00 | 48.84 | A |
| atom | 1186 | CA  | SER | A | 167 | 18.456 | −7.222  | 10.441 | 1.00 | 45.30 | A |
| atom | 1187 | CB  | SER | A | 167 | 19.671 | −8.169  | 10.461 | 1.00 | 45.62 | A |
| atom | 1188 | OG  | SER | A | 167 | 20.102 | −8.407  | 11.805 | 1.00 | 44.09 | A |
| atom | 1189 | C   | SER | A | 167 | 17.529 | −7.538  | 9.269  | 1.00 | 45.26 | A |
| atom | 1190 | O   | SER | A | 167 | 17.585 | −6.837  | 8.246  | 1.00 | 45.82 | A |
| atom | 1191 | N   | ARG | A | 168 | 16.667 | −8.553  | 9.422  | 1.00 | 42.96 | A |
| atom | 1192 | CA  | ARG | A | 168 | 15.723 | −8.969  | 8.359  | 1.00 | 42.75 | A |
| atom | 1193 | CB  | ARG | A | 168 | 15.112 | −10.335 | 8.667  | 1.00 | 40.44 | A |
| atom | 1194 | CG  | ARG | A | 168 | 16.095 | −11.495 | 8.686  | 1.00 | 41.40 | A |
| atom | 1195 | CD  | ARG | A | 168 | 15.332 | −12.799 | 8.886  | 1.00 | 39.12 | A |
| atom | 1196 | NE  | ARG | A | 168 | 14.595 | −12.707 | 10.137 | 1.00 | 42.95 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor; atom

| atom | 1197 | CZ | ARG | A | 168 | 13.813 | −13.639 | 10.658 | 1.00 | 43.70 | A |
|---|---|---|---|---|---|---|---|---|---|---|---|
| atom | 1198 | NH1 | ARG | A | 168 | 13.618 | −14.794 | 10.059 | 1.00 | 51.29 | A |
| atom | 1199 | NH2 | ARG | A | 168 | 13.221 | −13.395 | 11.806 | 1.00 | 44.89 | A |
| atom | 1200 | C | ARG | A | 168 | 14.556 | −8.004 | 8.140 | 1.00 | 42.76 | A |
| atom | 1201 | O | ARG | A | 168 | 13.972 | −7.946 | 7.054 | 1.00 | 41.68 | A |
| atom | 1202 | N | ALA | A | 169 | 14.199 | −7.271 | 9.186 | 1.00 | 41.68 | A |
| atom | 1203 | CA | ALA | A | 169 | 13.107 | −6.329 | 9.076 | 1.00 | 40.10 | A |
| atom | 1204 | CB | ALA | A | 169 | 12.705 | −5.857 | 10.456 | 1.00 | 38.29 | A |
| atom | 1205 | C | ALA | A | 169 | 13.583 | −5.169 | 8.186 | 1.00 | 40.34 | A |
| atom | 1206 | O | ALA | A | 169 | 12.786 | −4.571 | 7.456 | 1.00 | 43.06 | A |
| atom | 1207 | N | ARG | A | 170 | 14.890 | −4.883 | 8.248 | 1.00 | 39.23 | A |
| atom | 1208 | CA | ARG | A | 170 | 15.555 | −3.832 | 7.449 | 1.00 | 37.75 | A |
| atom | 1209 | CB | ARG | A | 170 | 17.045 | −3.708 | 7.796 | 1.00 | 43.50 | A |
| atom | 1210 | CG | ARG | A | 170 | 17.458 | −2.529 | 8.679 | 1.00 | 45.63 | A |
| atom | 1211 | CD | ARG | A | 170 | 18.068 | −3.021 | 9.977 | 1.00 | 52.14 | A |
| atom | 1212 | NE | ARG | A | 170 | 19.411 | −3.586 | 9.839 | 1.00 | 54.49 | A |
| atom | 1213 | CZ | ARG | A | 170 | 20.109 | −4.083 | 10.861 | 1.00 | 55.83 | A |
| atom | 1214 | NH1 | ARG | A | 170 | 19.591 | −4.086 | 12.091 | 1.00 | 54.07 | A |
| atom | 1215 | NH2 | ARG | A | 170 | 21.331 | −4.567 | 10.666 | 1.00 | 53.98 | A |
| atom | 1216 | C | ARG | A | 170 | 15.503 | −4.226 | 5.985 | 1.00 | 36.96 | A |
| atom | 1217 | O | ARG | A | 170 | 15.237 | −3.407 | 5.091 | 1.00 | 35.36 | A |
| atom | 1218 | N | ILE | A | 171 | 15.801 | −5.494 | 5.733 | 1.00 | 35.75 | A |
| atom | 1219 | CA | ILE | A | 171 | 15.778 | −5.987 | 4.356 | 1.00 | 36.28 | A |
| atom | 1220 | CB | ILE | A | 171 | 16.164 | −7.514 | 4.266 | 1.00 | 33.74 | A |
| atom | 1221 | CG2 | ILE | A | 171 | 15.671 | −8.072 | 2.918 | 1.00 | 31.00 | A |
| atom | 1222 | CG1 | ILE | A | 171 | 17.696 | −7.708 | 4.421 | 1.00 | 31.27 | A |
| atom | 1223 | CD1 | ILE | A | 171 | 18.159 | −9.075 | 4.983 | 1.00 | 28.02 | A |
| atom | 1224 | C | ILE | A | 171 | 14.357 | −5.792 | 3.827 | 1.00 | 37.91 | A |
| atom | 1225 | O | ILE | A | 171 | 14.154 | −5.266 | 2.744 | 1.00 | 39.81 | A |
| atom | 1226 | N | LYS | A | 172 | 13.366 | −6.164 | 4.629 | 1.00 | 41.11 | A |
| atom | 1227 | CA | LYS | A | 172 | 11.956 | −6.054 | 4.207 | 1.00 | 41.82 | A |
| atom | 1228 | CB | LYS | A | 172 | 11.054 | −6.714 | 5.232 | 1.00 | 40.00 | A |
| atom | 1229 | CG | LYS | A | 172 | 11.229 | −8.181 | 5.261 | 1.00 | 40.92 | A |
| atom | 1230 | CD | LYS | A | 172 | 10.422 | −8.741 | 6.387 | 1.00 | 37.55 | A |
| atom | 1231 | CE | LYS | A | 172 | 10.533 | −10.239 | 6.371 | 1.00 | 37.65 | A |
| atom | 1232 | NZ | LYS | A | 172 | 9.777 | −10.875 | 7.484 | 1.00 | 39.09 | A |
| atom | 1233 | C | LYS | A | 172 | 11.382 | −4.672 | 3.956 | 1.00 | 43.47 | A |
| atom | 1234 | O | LYS | A | 172 | 10.349 | −4.516 | 3.285 | 1.00 | 43.21 | A |
| atom | 1235 | N | THR | A | 173 | 12.069 | −3.708 | 4.558 | 1.00 | 43.02 | A |
| atom | 1236 | CA | THR | A | 173 | 11.802 | −2.274 | 4.564 | 1.00 | 42.68 | A |
| atom | 1237 | CB | THR | A | 173 | 12.612 | −1.689 | 5.732 | 1.00 | 43.55 | A |
| atom | 1238 | OG1 | THR | A | 173 | 11.748 | −1.524 | 6.850 | 1.00 | 45.32 | A |
| atom | 1239 | CG2 | THR | A | 173 | 13.314 | −0.386 | 5.365 | 1.00 | 44.51 | A |
| atom | 1240 | C | THR | A | 173 | 12.252 | −1.635 | 3.257 | 1.00 | 41.04 | A |
| atom | 1241 | O | THR | A | 173 | 11.614 | −0.734 | 2.670 | 1.00 | 41.45 | A |
| atom | 1242 | N | ARG | A | 174 | 13.397 | −2.114 | 2.828 | 1.00 | 36.80 | A |
| atom | 1243 | CA | ARG | A | 174 | 13.981 | −1.632 | 1.632 | 1.00 | 36.51 | A |
| atom | 1244 | CB | ARG | A | 174 | 15.457 | −1.916 | 1.704 | 1.00 | 32.48 | A |
| atom | 1245 | CG | ARG | A | 174 | 16.180 | −1.698 | 0.424 | 1.00 | 30.15 | A |
| atom | 1246 | CD | ARG | A | 174 | 15.897 | −0.342 | −0.151 | 1.00 | 28.41 | A |
| atom | 1247 | NE | ARG | A | 174 | 16.480 | −0.276 | −1.482 | 1.00 | 31.49 | A |
| atom | 1248 | CZ | ARG | A | 174 | 16.432 | 0.791 | −2.272 | 1.00 | 33.25 | A |
| atom | 1249 | NH1 | ARG | A | 174 | 15.824 | 1.900 | −1.868 | 1.00 | 34.92 | A |
| atom | 1250 | NH2 | ARG | A | 174 | 16.990 | 0.746 | −3.473 | 1.00 | 35.00 | A |
| atom | 1251 | C | ARG | A | 174 | 13.275 | −2.280 | 0.435 | 1.00 | 38.19 | A |
| atom | 1252 | O | ARG | A | 174 | 13.325 | −1.731 | −0.657 | 1.00 | 40.56 | A |
| atom | 1253 | N | LEU | A | 175 | 12.582 | −3.407 | 0.617 | 1.00 | 35.85 | A |
| atom | 1254 | CA | LEU | A | 175 | 11.853 | −3.975 | −0.517 | 1.00 | 36.58 | A |
| atom | 1255 | CB | LEU | A | 175 | 11.576 | −5.462 | −0.317 | 1.00 | 38.36 | A |
| atom | 1256 | CG | LEU | A | 175 | 12.915 | −6.146 | −0.352 | 1.00 | 39.31 | A |
| atom | 1257 | CD1 | LEU | A | 175 | 12.784 | −7.475 | 0.334 | 1.00 | 41.82 | A |
| atom | 1258 | CD2 | LEU | A | 175 | 13.424 | −6.249 | −1.788 | 1.00 | 37.56 | A |
| atom | 1259 | C | LEU | A | 175 | 10.569 | −3.190 | −0.692 | 1.00 | 35.84 | A |
| atom | 1260 | O | LEU | A | 175 | 10.157 | −2.944 | −1.810 | 1.00 | 35.67 | A |
| atom | 1261 | N | PHE | A | 176 | 9.959 | −2.753 | 0.412 | 1.00 | 39.94 | A |
| atom | 1262 | CA | PHE | A | 176 | 8.728 | −1.956 | 0.293 | 1.00 | 40.95 | A |
| atom | 1263 | CB | PHE | A | 176 | 8.043 | −1.659 | 1.649 | 1.00 | 44.71 | A |
| atom | 1264 | CG | PHE | A | 176 | 7.575 | −2.872 | 2.401 | 1.00 | 48.93 | A |
| atom | 1265 | CD1 | PHE | A | 176 | 8.031 | −3.100 | 3.694 | 1.00 | 51.16 | A |
| atom | 1266 | CD2 | PHE | A | 176 | 6.714 | −3.797 | 1.822 | 1.00 | 52.76 | A |
| atom | 1267 | CE1 | PHE | A | 176 | 7.642 | −4.238 | 4.405 | 1.00 | 51.40 | A |
| atom | 1268 | CE2 | PHE | A | 176 | 6.322 | −4.941 | 2.526 | 1.00 | 50.53 | A |
| atom | 1269 | CZ | PHE | A | 176 | 6.792 | −5.156 | 3.820 | 1.00 | 49.67 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor;
atom

| | | | | | | | | | | |
|---|---|---|---|---|---|---|---|---|---|---|
| atom | 1270 | C | PHE | A | 176 | 9.078 | −0.610 | −0.333 | 1.00 | 41.73 | A |
| atom | 1271 | O | PHE | A | 176 | 8.349 | −0.092 | −1.179 | 1.00 | 42.21 | A |
| atom | 1272 | N | THR | A | 177 | 10.207 | −0.049 | 0.085 | 1.00 | 41.28 | A |
| atom | 1273 | CA | THR | A | 177 | 10.647 | 1.246 | −0.422 | 1.00 | 40.40 | A |
| atom | 1274 | CB | THR | A | 177 | 11.960 | 1.650 | 0.288 | 1.00 | 40.67 | A |
| atom | 1275 | OG1 | THR | A | 177 | 11.698 | 1.711 | 1.692 | 1.00 | 41.64 | A |
| atom | 1276 | CG2 | THR | A | 177 | 12.489 | 3.010 | −0.189 | 1.00 | 40.44 | A |
| atom | 1277 | C | THR | A | 177 | 10.815 | 1.117 | −1.939 | 1.00 | 39.16 | A |
| atom | 1278 | O | THR | A | 177 | 10.282 | 1.917 | −2.704 | 1.00 | 41.59 | A |
| atom | 1279 | N | ILE | A | 178 | 11.525 | 0.083 | −2.370 | 1.00 | 38.59 | A |
| atom | 1280 | CA | ILE | A | 178 | 11.718 | −0.144 | −3.791 | 1.00 | 35.84 | A |
| atom | 1281 | CB | ILE | A | 178 | 12.508 | −1.444 | −4.021 | 1.00 | 33.29 | A |
| atom | 1282 | CG2 | ILE | A | 178 | 12.799 | −1.617 | −5.492 | 1.00 | 35.02 | A |
| atom | 1283 | CG1 | ILE | A | 178 | 13.829 | −1.367 | −3.281 | 1.00 | 31.61 | A |
| atom | 1284 | CD1 | ILE | A | 178 | 14.772 | −2.564 | −3.518 | 1.00 | 26.17 | A |
| atom | 1285 | C | ILE | A | 178 | 10.335 | −0.216 | −4.498 | 1.00 | 35.91 | A |
| atom | 1286 | O | ILE | A | 178 | 10.149 | 0.345 | −5.574 | 1.00 | 34.03 | A |
| atom | 1287 | N | ARG | A | 179 | 9.377 | −0.903 | −3.880 | 1.00 | 35.48 | A |
| atom | 1288 | CA | ARG | A | 179 | 8.035 | −1.072 | −4.429 | 1.00 | 38.94 | A |
| atom | 1289 | CB | ARG | A | 179 | 7.250 | −2.061 | −3.563 | 1.00 | 39.57 | A |
| atom | 1290 | CG | ARG | A | 179 | 5.834 | −2.235 | −4.018 | 1.00 | 44.04 | A |
| atom | 1291 | CD | ARG | A | 179 | 4.938 | −2.360 | −2.811 | 1.00 | 44.75 | A |
| atom | 1292 | NE | ARG | A | 179 | 4.823 | −3.724 | −2.331 | 1.00 | 48.81 | A |
| atom | 1293 | CZ | ARG | A | 179 | 4.209 | −4.087 | −1.197 | 1.00 | 50.19 | A |
| atom | 1294 | NH1 | ARG | A | 179 | 3.630 | −3.200 | −0.367 | 1.00 | 43.50 | A |
| atom | 1295 | NH2 | ARG | A | 179 | 4.152 | −5.376 | −0.890 | 1.00 | 43.74 | A |
| atom | 1296 | C | ARG | A | 179 | 7.207 | 0.207 | −4.609 | 1.00 | 36.86 | A |
| atom | 1297 | O | ARG | A | 179 | 6.714 | 0.467 | −5.693 | 1.00 | 36.37 | A |
| atom | 1298 | N | GLN | A | 180 | 7.037 | 1.016 | −3.572 | 1.00 | 39.38 | A |
| atom | 1299 | CA | GLN | A | 180 | 6.228 | 2.205 | −3.769 | 1.00 | 42.17 | A |
| atom | 1300 | CB | GLN | A | 180 | 5.671 | 2.715 | −2.430 | 1.00 | 44.33 | A |
| atom | 1301 | CG | GLN | A | 180 | 6.438 | 2.274 | −1.222 | 1.00 | 46.62 | A |
| atom | 1302 | CD | GLN | A | 180 | 7.251 | 3.400 | −0.687 | 1.00 | 51.32 | A |
| atom | 1303 | OE1 | GLN | A | 180 | 7.562 | 4.335 | −1.421 | 1.00 | 51.48 | A |
| atom | 1304 | NE2 | GLN | A | 180 | 7.589 | 3.345 | 0.597 | 1.00 | 49.06 | A |
| atom | 1305 | C | GLN | A | 180 | 6.937 | 3.283 | −4.584 | 1.00 | 41.42 | A |
| atom | 1306 | O | GLN | A | 180 | 6.285 | 4.181 | −5.103 | 1.00 | 40.99 | A |
| atom | 1307 | N | GLU | A | 181 | 8.259 | 3.197 | −4.734 | 1.00 | 40.46 | A |
| atom | 1308 | CA | GLU | A | 181 | 8.923 | 4.189 | −5.587 | 1.00 | 39.31 | A |
| atom | 1309 | CB | GLU | A | 181 | 10.402 | 4.416 | −5.258 | 1.00 | 39.74 | A |
| atom | 1310 | CG | GLU | A | 181 | 11.123 | 5.312 | −6.292 | 1.00 | 48.32 | A |
| atom | 1311 | CD | GLU | A | 181 | 10.506 | 6.702 | −6.418 | 1.00 | 55.12 | A |
| atom | 1312 | OE1 | GLU | A | 181 | 10.419 | 7.222 | −7.553 | 1.00 | 55.57 | A |
| atom | 1313 | OE2 | GLU | A | 181 | 10.114 | 7.287 | −5.384 | 1.00 | 60.29 | A |
| atom | 1314 | C | GLU | A | 181 | 8.799 | 3.613 | −6.981 | 1.00 | 38.08 | A |
| atom | 1315 | O | GLU | A | 181 | 8.983 | 4.311 | −7.968 | 1.00 | 38.22 | A |
| atom | 1316 | N | MET | A | 182 | 8.506 | 2.324 | −7.085 | 1.00 | 34.65 | A |
| atom | 1317 | CA | MET | A | 182 | 8.316 | 1.825 | −8.426 | 1.00 | 35.64 | A |
| atom | 1318 | CB | MET | A | 182 | 8.424 | 0.302 | −8.511 | 1.00 | 38.04 | A |
| atom | 1319 | CG | MET | A | 182 | 9.709 | −0.195 | −9.101 | 1.00 | 34.28 | A |
| atom | 1320 | SD | MET | A | 182 | 9.540 | −1.927 | −8.944 | 1.00 | 37.19 | A |
| atom | 1321 | CE | MET | A | 182 | 11.071 | −2.505 | −9.329 | 1.00 | 15.46 | A |
| atom | 1322 | C | MET | A | 182 | 6.921 | 2.260 | −8.777 | 1.00 | 36.85 | A |
| atom | 1323 | O | MET | A | 182 | 6.656 | 2.685 | −9.896 | 1.00 | 39.65 | A |
| atom | 1324 | N | ALA | A | 183 | 6.042 | 2.169 | −7.783 | 1.00 | 36.57 | A |
| atom | 1325 | CA | ALA | A | 183 | 4.629 | 2.532 | −7.929 | 1.00 | 37.16 | A |
| atom | 1326 | CB | ALA | A | 183 | 3.890 | 2.241 | −6.635 | 1.00 | 36.36 | A |
| atom | 1327 | C | ALA | A | 183 | 4.402 | 4.002 | −8.307 | 1.00 | 38.95 | A |
| atom | 1328 | O | ALA | A | 183 | 3.592 | 4.310 | −9.186 | 1.00 | 36.70 | A |
| atom | 1329 | N | SER | A | 184 | 5.104 | 4.904 | −7.628 | 1.00 | 39.45 | A |
| atom | 1330 | CA | SER | A | 184 | 4.940 | 6.310 | −7.894 | 1.00 | 39.46 | A |
| atom | 1331 | CB | SER | A | 184 | 5.861 | 7.128 | −6.968 | 1.00 | 42.13 | A |
| atom | 1332 | OG | SER | A | 184 | 7.245 | 7.022 | −7.298 | 1.00 | 48.29 | A |
| atom | 1333 | C | SER | A | 184 | 5.186 | 6.627 | −9.376 | 1.00 | 39.78 | A |
| atom | 1334 | O | SER | A | 184 | 4.575 | 7.561 | −9.927 | 1.00 | 40.91 | A |
| atom | 1335 | N | ARG | A | 185 | 6.030 | 5.816 | −10.024 | 1.00 | 38.10 | A |
| atom | 1336 | CA | ARG | A | 185 | 6.421 | 5.972 | −11.441 | 1.00 | 38.54 | A |
| atom | 1337 | CB | ARG | A | 185 | 7.836 | 5.500 | −11.615 | 1.00 | 39.60 | A |
| atom | 1338 | CG | ARG | A | 185 | 8.731 | 5.856 | −10.482 | 1.00 | 43.85 | A |
| atom | 1339 | CD | ARG | A | 185 | 9.582 | 7.003 | −10.872 | 1.00 | 43.92 | A |
| atom | 1340 | NE | ARG | A | 185 | 10.579 | 7.214 | −9.845 | 1.00 | 43.92 | A |
| atom | 1341 | CZ | ARG | A | 185 | 11.846 | 7.508 | −10.096 | 1.00 | 47.56 | A |
| atom | 1342 | NH1 | ARG | A | 185 | 12.275 | 7.629 | −11.352 | 1.00 | 47.14 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor;
atom

| | | | | | | | | | | |
|---|---|---|---|---|---|---|---|---|---|---|
| atom | 1343 | NH2 | ARG | A | 185 | 12.687 | 7.676 | −9.088 | 1.00 | 49.32 | A |
| atom | 1344 | C | ARG | A | 185 | 5.566 | 5.135 | −12.384 | 1.00 | 38.55 | A |
| atom | 1345 | O | ARG | A | 185 | 5.744 | 5.186 | −13.599 | 1.00 | 36.63 | A |
| atom | 1346 | N | GLY | A | 186 | 4.634 | 4.382 | −11.792 | 1.00 | 38.35 | A |
| atom | 1347 | CA | GLY | A | 186 | 3.734 | 3.494 | −12.522 | 1.00 | 34.39 | A |
| atom | 1348 | C | GLY | A | 186 | 4.432 | 2.251 | −13.066 | 1.00 | 35.47 | A |
| atom | 1349 | O | GLY | A | 186 | 4.024 | 1.662 | −14.078 | 1.00 | 36.52 | A |
| atom | 1350 | N | LEU | A | 187 | 5.492 | 1.824 | −12.388 | 1.00 | 35.09 | A |
| atom | 1351 | CA | LEU | A | 187 | 6.306 | 0.688 | −12.866 | 1.00 | 32.71 | A |
| atom | 1352 | CB | LEU | A | 187 | 7.783 | 1.027 | −12.652 | 1.00 | 31.96 | A |
| atom | 1353 | CG | LEU | A | 187 | 8.565 | 1.941 | −13.597 | 1.00 | 32.36 | A |
| atom | 1354 | CD1 | LEU | A | 187 | 7.682 | 2.592 | −14.629 | 1.00 | 31.78 | A |
| atom | 1355 | CD2 | LEU | A | 187 | 9.283 | 2.993 | −12.769 | 1.00 | 30.26 | A |
| atom | 1356 | C | LEU | A | 187 | 6.061 | −0.685 | −12.234 | 1.00 | 31.58 | A |
| atom | 1357 | O | LEU | A | 187 | 6.466 | −1.714 | −12.767 | 1.00 | 31.78 | A |
| atom | 1358 | N | TRP | A | 188 | 5.412 | −0.673 | −11.084 | 1.00 | 36.15 | A |
| atom | 1359 | CA | TRP | A | 188 | 5.106 | −1.850 | −10.311 | 1.00 | 37.72 | A |
| atom | 1360 | CB | TRP | A | 188 | 4.373 | −1.402 | −9.053 | 1.00 | 37.80 | A |
| atom | 1361 | CG | TRP | A | 188 | 4.114 | −2.500 | −8.138 | 1.00 | 36.87 | A |
| atom | 1362 | CD2 | TRP | A | 188 | 5.103 | −3.321 | −7.522 | 1.00 | 37.71 | A |
| atom | 1363 | CE2 | TRP | A | 188 | 4.417 | −4.281 | −6.735 | 1.00 | 33.19 | A |
| atom | 1364 | CE3 | TRP | A | 188 | 6.509 | −3.311 | −7.518 | 1.00 | 36.97 | A |
| atom | 1365 | CD1 | TRP | A | 188 | 2.901 | −2.994 | −7.751 | 1.00 | 37.59 | A |
| atom | 1366 | NE1 | TRP | A | 188 | 3.075 | −4.073 | −6.912 | 1.00 | 32.23 | A |
| atom | 1367 | CZ2 | TRP | A | 188 | 5.106 | −5.266 | −6.000 | 1.00 | 33.55 | A |
| atom | 1368 | CZ3 | TRP | A | 188 | 7.180 | −4.280 | −6.794 | 1.00 | 34.26 | A |
| atom | 1369 | CH2 | TRP | A | 188 | 6.484 | −5.225 | −6.022 | 1.00 | 33.13 | A |
| atom | 1370 | C | TRP | A | 188 | 4.249 | −2.882 | −11.023 | 1.00 | 39.20 | A |
| atom | 1371 | O | TRP | A | 188 | 4.586 | −4.058 | −11.075 | 1.00 | 39.44 | A |
| atom | 1372 | N | ASP | A | 189 | 3.118 | −2.425 | −11.534 | 1.00 | 38.97 | A |
| atom | 1373 | CA | ASP | A | 189 | 2.177 | −3.327 | −12.160 | 1.00 | 41.46 | A |
| atom | 1374 | CB | ASP | A | 189 | 1.049 | −2.526 | −12.801 | 1.00 | 46.52 | A |
| atom | 1375 | CG | ASP | A | 189 | −0.320 | −3.012 | −12.338 | 1.00 | 52.18 | A |
| atom | 1376 | OD1 | ASP | A | 189 | −0.956 | −3.753 | −13.112 | 1.00 | 55.99 | A |
| atom | 1377 | OD2 | ASP | A | 189 | −0.760 | −2.700 | −11.198 | 1.00 | 58.95 | A |
| atom | 1378 | C | ASP | A | 189 | 2.808 | −4.329 | −13.119 | 1.00 | 38.34 | A |
| atom | 1379 | O | ASP | A | 189 | 2.495 | −5.508 | −13.064 | 1.00 | 36.45 | A |
| atom | 1380 | N | SER | A | 190 | 3.727 | −3.867 | −13.955 | 1.00 | 36.70 | A |
| atom | 1381 | CA | SER | A | 190 | 4.426 | −4.704 | −14.914 | 1.00 | 34.73 | A |
| atom | 1382 | CB | SER | A | 190 | 4.870 | −3.787 | −16.073 | 1.00 | 33.57 | A |
| atom | 1383 | OG | SER | A | 190 | 5.732 | −4.428 | −17.013 | 1.00 | 38.08 | A |
| atom | 1384 | C | SER | A | 190 | 5.593 | −5.430 | −14.185 | 1.00 | 32.59 | A |
| atom | 1385 | O | SER | A | 190 | 5.790 | −6.625 | −14.377 | 1.00 | 34.63 | A |
| atom | 1386 | N | PHE | A | 191 | 6.323 | −4.736 | −13.309 | 1.00 | 33.95 | A |
| atom | 1387 | CA | PHE | A | 191 | 7.405 | −5.388 | −12.571 | 1.00 | 28.50 | A |
| atom | 1388 | CB | PHE | A | 191 | 8.073 | −4.406 | −11.567 | 1.00 | 27.70 | A |
| atom | 1389 | CG | PHE | A | 191 | 9.249 | −4.993 | −10.836 | 1.00 | 23.40 | A |
| atom | 1390 | CD1 | PHE | A | 191 | 10.401 | −5.349 | −11.527 | 1.00 | 25.35 | A |
| atom | 1391 | CD2 | PHE | A | 191 | 9.185 | −5.247 | −9.468 | 1.00 | 24.51 | A |
| atom | 1392 | CE1 | PHE | A | 191 | 11.480 | −5.952 | −10.862 | 1.00 | 20.84 | A |
| atom | 1393 | CE2 | PHE | A | 191 | 10.280 | −5.859 | −8.799 | 1.00 | 25.42 | A |
| atom | 1394 | CZ | PHE | A | 191 | 11.416 | −6.204 | −9.517 | 1.00 | 20.19 | A |
| atom | 1395 | C | PHE | A | 191 | 6.876 | −6.612 | −11.810 | 1.00 | 31.16 | A |
| atom | 1396 | O | PHE | A | 191 | 7.412 | −7.710 | −11.937 | 1.00 | 34.37 | A |
| atom | 1397 | N | ARG | A | 192 | 5.830 | −6.408 | −11.013 | 1.00 | 34.99 | A |
| atom | 1398 | CA | ARG | A | 192 | 5.228 | −7.460 | −10.166 | 1.00 | 37.91 | A |
| atom | 1399 | CB | ARG | A | 192 | 4.086 | −6.895 | −9.305 | 1.00 | 40.34 | A |
| atom | 1400 | CG | ARG | A | 192 | 3.368 | −8.059 | −8.558 | 1.00 | 44.54 | A |
| atom | 1401 | CD | ARG | A | 192 | 1.914 | −7.822 | −8.135 | 1.00 | 51.54 | A |
| atom | 1402 | NE | ARG | A | 192 | 0.899 | −7.580 | −9.176 | 1.00 | 56.19 | A |
| atom | 1403 | CZ | ARG | A | 192 | 0.617 | −6.373 | −9.656 | 1.00 | 56.73 | A |
| atom | 1404 | NH1 | ARG | A | 192 | 1.285 | −5.317 | −9.212 | 1.00 | 57.21 | A |
| atom | 1405 | NH2 | ARG | A | 192 | −0.391 | −6.198 | −10.496 | 1.00 | 57.91 | A |
| atom | 1406 | C | ARG | A | 192 | 4.634 | −8.712 | −10.808 | 1.00 | 37.29 | A |
| atom | 1407 | O | ARG | A | 192 | 4.408 | −9.729 | −10.147 | 1.00 | 40.15 | A |
| atom | 1408 | N | GLN | A | 193 | 4.346 | −8.632 | −12.087 | 1.00 | 35.81 | A |
| atom | 1409 | CA | GLN | A | 193 | 3.698 | −9.742 | −12.738 | 1.00 | 38.48 | A |
| atom | 1410 | CB | GLN | A | 193 | 2.308 | −9.281 | −13.182 | 1.00 | 38.50 | A |
| atom | 1411 | CG | GLN | A | 193 | 2.315 | −7.988 | −14.036 | 1.00 | 45.90 | A |
| atom | 1412 | CD | GLN | A | 193 | 0.912 | −7.541 | −14.446 | 1.00 | 50.22 | A |
| atom | 1413 | OE1 | GLN | A | 193 | 0.678 | −6.373 | −14.786 | 1.00 | 52.52 | A |
| atom | 1414 | NE2 | GLN | A | 193 | −0.029 | −8.477 | −14.418 | 1.00 | 54.59 | A |
| atom | 1415 | C | GLN | A | 193 | 4.477 | −10.298 | −13.916 | 1.00 | 38.28 | A |

TABLE 1-continued

Atom coordinate for single molecule was shown as below:
Notes: Coordinate was established on May 08, 2008, and edited on Feb. 01, 2009.
Notes: 3 Maximum resolution (angstrom): 2.2
Notes: 3 Minimum resolution (angstrom): 30
X-coordinate; Y-coordinate; Z-coordinate; occupancy; temperature factor;
atom

| | | | | | | | | | | |
|---|---|---|---|---|---|---|---|---|---|---|
| atom | 1416 | O | GLN | A | 193 | 3.931 | −11.008 | −14.775 | 1.00 | 37.58 | A |
| atom | 1417 | N | SER | A | 194 | 5.768 | −10.004 | −13.935 | 1.00 | 38.41 | A |
| atom | 1418 | CA | SER | A | 194 | 6.643 | −10.447 | −15.004 | 1.00 | 38.20 | A |
| atom | 1419 | CB | SER | A | 194 | 7.221 | −9.227 | −15.719 | 1.00 | 39.28 | A |
| atom | 1420 | OG | SER | A | 194 | 7.771 | −8.306 | −14.784 | 1.00 | 47.74 | A |
| atom | 1421 | C | SER | A | 194 | 7.762 | −11.358 | −14.526 | 1.00 | 38.11 | A |
| atom | 1422 | O | SER | A | 194 | 8.751 | −11.549 | −15.248 | 1.00 | 35.39 | A |
| atom | 1423 | N | GLU | A | 195 | 7.612 | −11.922 | −13.327 | 1.00 | 35.72 | A |
| atom | 1424 | CA | GLU | A | 195 | 8.631 | −12.827 | −12.850 | 1.00 | 36.50 | A |
| atom | 1425 | CB | GLU | A | 195 | 8.720 | −12.875 | −11.351 | 1.00 | 36.67 | A |
| atom | 1426 | CG | GLU | A | 195 | 9.600 | −14.015 | −10.888 | 1.00 | 35.54 | A |
| atom | 1427 | CD | GLU | A | 195 | 9.744 | −13.962 | −9.413 | 1.00 | 37.06 | A |
| atom | 1428 | OE1 | GLU | A | 195 | 9.984 | −12.849 | −8.907 | 1.00 | 40.23 | A |
| atom | 1429 | OE2 | GLU | A | 195 | 9.622 | −15.003 | −8.749 | 1.00 | 33.08 | A |
| atom | 1430 | C | GLU | A | 195 | 8.287 | −14.210 | −13.335 | 1.00 | 37.87 | A |
| atom | 1431 | O | GLU | A | 195 | 7.201 | −14.718 | −13.097 | 1.00 | 38.80 | A |
| atom | 1432 | N | ARG | A | 196 | 9.270 | −14.818 | −13.962 | 1.00 | 36.44 | A |
| atom | 1433 | CA | ARG | A | 196 | 9.146 | −16.103 | −14.561 | 1.00 | 37.25 | A |
| atom | 1434 | CB | ARG | A | 196 | 9.495 | −15.865 | −16.017 | 1.00 | 35.97 | A |
| atom | 1435 | CG | ARG | A | 196 | 10.220 | −16.869 | −16.774 | 1.00 | 35.63 | A |
| atom | 1436 | CD | ARG | A | 196 | 10.115 | −16.310 | −18.145 | 1.00 | 42.73 | A |
| atom | 1437 | NE | ARG | A | 196 | 9.641 | −17.309 | −19.071 | 1.00 | 48.88 | A |
| atom | 1438 | CZ | ARG | A | 196 | 9.164 | −17.028 | −20.272 | 1.00 | 51.24 | A |
| atom | 1439 | NH1 | ARG | A | 196 | 8.759 | −18.012 | −21.064 | 1.00 | 52.08 | A |
| atom | 1440 | NH2 | ARG | A | 196 | 9.068 | −15.764 | −20.667 | 1.00 | 51.19 | A |
| atom | 1441 | C | ARG | A | 196 | 10.057 | −17.072 | −13.842 | 1.00 | 40.12 | A |
| atom | 1442 | O | ARG | A | 196 | 10.944 | −16.620 | −13.107 | 1.00 | 39.42 | A |
| atom | 1443 | N | GLY | A | 197 | 9.856 | −18.380 | −14.001 | 1.00 | 38.00 | A |
| atom | 1444 | CA | GLY | A | 197 | 10.760 | −19.285 | −13.313 | 1.00 | 36.72 | A |
| atom | 1445 | C | GLY | A | 197 | 11.962 | −19.318 | −14.228 | 1.00 | 35.38 | A |
| atom | 1446 | O | GLY | A | 197 | 13.088 | −19.505 | −13.801 | 1.00 | 38.62 | A |
| atom | 1447 | MG | MG | A | 999 | 23.785 | −15.925 | −7.227 | 1.00 | 40.31 | A |
| atom | 1448 | OH2 | TIP | A | 1001 | 25.989 | −16.102 | −7.182 | 1.00 | 38.07 | A |
| atom | 1449 | OH2 | TIP | A | 1002 | 21.329 | −15.908 | −6.882 | 1.00 | 48.60 | A |
| atom | 1450 | OH2 | TIP | A | 1003 | 23.416 | −18.109 | −6.644 | 1.00 | 29.11 | A |
| end | | | | | | | | | | | |

Present invention compared the sequence of PA_N of SEQ ID NO: 1 from influenza viruses. H5N1 A/goose/Guangdong/1/96 of SEQ ID NO:1; A/Brevig Mission/1/1918 of SEQ ID NO:8, which was a widely-circulating outbreak that caused the death of millions of people in Europe in 1918; B/Ann Arbor/1/1966 of SEQ ID NO:3 and C strain C/JJ/1950 of SEQ ID NO:4. Results were shown in FIGS. 1 & 4.

Present invention cloned two parts of P_N of SEQ ID NO: 1 gene, N-terminal (residues 1-256 of SEQ ID NO:1) and C-terminal (residues 257-716 of SEQ ID NO:1), from influenza virus RNA polymerase respectively, expressed and purified GST-fusion proteins, and obtained the well-diffractive parental crystals of purified PA_N of SEQ ID NO: 7.

Experiment in vitro demonstrated that PA expressing *E. coli* and PB1 of SEQ ID NO: 2 expressing *E. coli* were mixed at certain ratio; two proteins PA (SEQ ID NO: 1) and PB1 (SEQ ID NO: 2) were co-purified and obtained using Glutathione-Sepharose affinity column and gel filtration chromatography. The results of co-purification showed residues 460 of PA_N of SEQ ID NO: 1 and GST-PB1 peptide formed a stable complex.

Moreover, experiment in vitro demonstrated that PA_N of SEQ ID NO: 1 expressing *E. coli* was obtained, and PA_N of SEQ ID NO: 1 peptide was purified and used for crystal experiment. A well-diffractive crystal of PA_N of SEQ ID NO: 7 peptide was obtained at various conditions.

The invention claimed is:
1. A method comprising the steps of:
i. obtaining an N-terminal protein crystal of influenza virus subunit PA_N consisting of SEQ ID NO: 7, said crystal is selected from the group consisting of triclinic crystal in space group P1 and cell unit dimensions of a=51.1 Å; b=151.0 Å; c=59.8 Å; α=96.6°; β=96.8°; and γ=109.5°, and a hexagonal crystal in space group P6$_4$22 and cell unit dimensions of a=b=73.8 Å; c=123.4 Å; α=β=90°; γ=120°;
ii. determining the three-dimensional structure of the crystal of (i) using an X-ray diffraction method to obtain atomic coordinates of the structure;
iii. constructing a three dimensional model;
iv. using said three-dimensional model for computationally identifying a compound that binds to a binding site of PA-N of SEQ ID NO: 7, wherein said compound is selected from the group consisting of peptides, proteins, antibodies or immune conjugates;
v. synthesizing said compound; and
vi. combining said compound with at least a second influenza virus polymerase subunit to determine if said compound modulates the activity of said influenza virus polymerase subunit.

2. The method of claim 1 wherein said binding site comprises amino acid residues of PA-N of SEQ ID NO: 7 including: Glu80; Asp108; His41; Glu119; Leu106; and Pro107.

3. The method of claim 1 wherein said binding site comprises amino acid residues of PA-N of SEQ ID NO: 7 including: Glu2; Asp3; Arg6; Gln10; Glu15; Glu18; Lys19; Lys22; Asp27; and Lys29.

4. The method of claim 1 wherein said binding site comprises amino acid residues of PA-N of SEQ ID NO: 7 including: Arg179; Asp189; Arg192; Gln193; and Glu126.

5. The method of claim 1 wherein said binding site comprises amino acid residues of PA-N of SEQ ID NO: 7 including: T157; E153; E154; K158; D160; E165; E166; R168; R170; and Lys172.

6. The method of claim 1 wherein said second influenza virus polymerase subunit comprises an N-terminus sequence having at least 50% sequence homology to PA-N of SEQ ID NO: 7.

7. The method of claim 1 wherein said second influenza virus polymerase subunit is derived from influenza virus type A strain.

8. The method of claim 7 wherein said influenza virus type A strain is derived from the group consisting of: A/goose/Guangdong/1/96 or A/Brevig Mission/1/1918.

9. The method of claim 1 wherein said second influenza virus polymerase subunit is derived from influenza virus type B.

10. The method of claim 9 wherein said influenza virus type B strain is derived from B/Ann Arbor/1/1966.

11. The method of claim 1 wherein said second influenza virus polymerase subunit is derived from influenza virus type C.

12. The method of claim 11 wherein said influenza virus type C strain is derived from C/JJ/1950.

* * * * *